(12) United States Patent
Kai et al.

(10) Patent No.: US 6,916,806 B2
(45) Date of Patent: Jul. 12, 2005

(54) MEDICINAL COMPOSITION CONTAINING 1,3-THIAZINE DERIVATIVE

(75) Inventors: Hiroyuki Kai, Koka-gun (JP); Takami Murashi, Osaka (JP); Minoru Tomida, Koka-gun (JP)

(73) Assignee: Shionogi & Co., Ltd., Osaka (JP)

( * ) Notice: Subject to any disclaimer, the term of this patent is extended or adjusted under 35 U.S.C. 154(b) by 41 days.

(21) Appl. No.: 10/470,388

(22) PCT Filed: Feb. 14, 2002

(86) PCT No.: PCT/JP02/01229

§ 371 (c)(1),
(2), (4) Date: Jul. 28, 2003

(87) PCT Pub. No.: WO02/072562

PCT Pub. Date: Sep. 19, 2002

(65) Prior Publication Data

US 2004/0116326 A1 Jun. 17, 2004

(30) Foreign Application Priority Data

Mar. 8, 2001 (JP) ..................... 2001-065386

(51) Int. Cl.[7] .................. C07D 417/04; C07D 417/12; C07D 417/14; A61K 31/541; A61P 29/00

(52) U.S. Cl. ................. 514/227.2; 514/226.8; 544/6; 544/55

(58) Field of Search ........................ 514/227.2, 226.8; 544/6, 55

(56) References Cited

U.S. PATENT DOCUMENTS

| | | | |
|---|---|---|---|
| 4,681,874 A | 7/1987 | Hayase et al. | 514/90 |
| 4,931,444 A | 6/1990 | Van Wauwe et al. | 514/252 |
| 5,194,434 A | 3/1993 | Chiou | 514/227.2 |
| 5,433,829 A | 7/1995 | Pool et al. | 204/130 |
| 6,017,919 A | 1/2000 | Inaba et al. | 514/251 |
| 6,545,050 B1 | 4/2003 | Mittendorf et al. | 514/570 |

FOREIGN PATENT DOCUMENTS

| | | |
|---|---|---|
| EP | 1 219 612 | 7/2002 |
| JP | 62-29594 | 2/1987 |
| JP | 62-120374 | 6/1987 |
| WO | 98/41519 | 9/1998 |
| WO | 99/02499 | 1/1999 |
| WO | 00/42031 | 7/2000 |
| WO | 01/19807 | 3/2001 |

OTHER PUBLICATIONS

T. Zawisza et al., "Synthesis and Pharmacological Analysis of New Derivatives of Tetrahydro–[1,3]–Thiazine and 2–Thiobarbituric Acid", Arch. Immunol. Ther. Exp., vol. 29, No. 2, pp. 235–248, 1981.

J. Gieldanowski et al., "Pharmacological Activity in the Group of New Substituted Thiazoloacetic and Thiazinocarboxyl Acid Derivatives", Arch. Immunol. Ther. Exp., vol. 26, No. 1–6, pp. 921–929, 1978.

K. Soderstrom et al., "Behavioral, Pharmacological, and Molecular Characterization of an Amphibian Cannabinoid Receptor", Journal of Neurochemistry, vol. 75, No. 1, pp. 413–423, 2000.

K. Lake et al., "Cardiovascular Effects of Anadamide in Anesthetized and Conscious Normotensive and Hypertensive Rats", Hypertension, vol. 29, pp. 1204–1210, 1997.

S. Munro et al., "Molecular Characterization of a Peripheral Receptor for Cannabinoids", Letters to Nature, vol. 365, pp. 61–65, Sep. 2, 1993.

H. Iwamura et al., "In Vitro and in Vivo Pharmacological Characterization of JTE–907, A Novel Selective Ligand for Cannabinoid $CB_2$ Receptor", J. Pharmacol. Exp. Ther., vol. 296, No. 2, pp. 420–425, 2001.

*Primary Examiner*—Mark L Berch
*Assistant Examiner*—Kahsay Habte
(74) *Attorney, Agent, or Firm*—Wenderoth, Lind & Ponack, L.L.P.

(57) ABSTRACT

A compound of the formula (I) having a binding activity to the cannabinoid type 2 receptor:

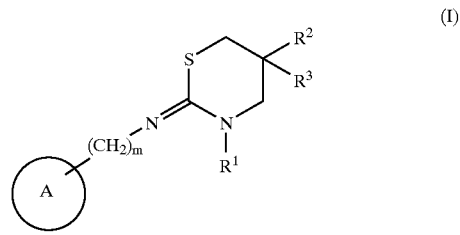

(I)

wherein $R^1$ is optionally substituted heterocyclic group or the like; $R^2$ and $R^2$ each is independently hydrogen or the like; m is an integer of 0 to 2; A is optionally substituted aromatic carbocyclic group or the like.

15 Claims, No Drawings

MEDICINAL COMPOSITION CONTAINING 1,3-THIAZINE DERIVATIVE

This application is a U.S. national stage of international application No. PCT/JP02/01229 filed Feb. 14, 2002.

TECHNICAL FIELD

The present invention relates to 2-imino-1,3-thiazine derivatives, in detail, 2-imino-1,3-thiazine derivatives having a binding activity to a cannabinoid type 2 receptor and pharmaceutical use of thereof.

BACKGROUND ART

Cannabinoid was discovered as the main active substance contained in marijuana in 1960 and found to exhibit an activity in the central nervous system (illusion, euphoria, sensory confusion of time and space) and in the peripheral cell system (immunosuppressive activity, anti-inflammatory activity, analgesic activity).

After that, anandamide and 2-arachidonoylglycerol produced from arachidonic acid-containing phospholipids were discovered as endogenous agonists to the cannabinoid receptor. These endogenous agonists are known to exhibit an activity to the central nervous system and an activity to the peripheral cell system. It is disclosed in Hypertension (1997) 29, 1204–1210 that anandamide exhibits an activity to the cardiovascular system.

A cannabinoid type 1 receptor discovered in 1990 was found to distribute in the central nervous system such as the brain. Agonists to this receptor were found to suppress the release of neurotransmitters to cause central actions such as illusion. A cannabinoid type 2 receptor discovered in 1993 was found to distribute in immune tissues such as the spleen. Agonists to this receptor were found to suppress an activation of immunocyte or inflammatory cells to exhibit an immunosuppressive activity, an anti-inflammatory activity and an analgesic activity (Nature, 1993, 365, 61–65).

Therefore, agonists to the cannabinoid type 2 receptor are expected as immunosuppressive agents, anti-inflammatory agents, and analgesic agents (Nature, 1998, 349, 277–281).

Known as compounds having an agonistic activity to the cannabinoid type 2 receptor are isoindolynone derivatives (WO97/29079 and WO99/02499), pyrazole derivatives (WO98/41519) and the like.

Furthermore, J. Pharmacol. Exp. Ther., 2001, 296, 420–425 discloses that compounds having a binding activity (an agonistic activity and/or an antagonistic activity) to the cannabinoid type 2 receptor exhibit anti-inflammatory effect.

On the other hand, Japanese Patent Publications (Kokai 1986-65894, Kokai 1987-29594) disclose that organophosphorus compounds having a 2-imino-1,3-thiazine skelton are useful as insecticides.

Furthermore, WO00/42031 discloses that compounds resembling the compound of the present invention have a binding activity to the progesterone receptor.

However, it is not known that 2-imino-1,3-thiazine derivatives have a binding activity (an antagonistic activity and/or agonistic activity) to the cannabinoid type 2 receptor.

DISCLOSURE OF INVENTION

The present invention is to find compounds having a binding activity (an antagonistic activity and/or agonistic activity) to the cannabinoid type 2 receptor.

The present invention provides 2-imino-1,3-thiazine derivatives as novel compounds having a binding activity to the cannabinoid type 2 receptor.

The present invention comprises,
(1) a compound of the formula (I):

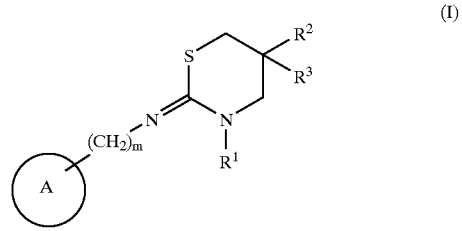

(I)

wherein $R^1$ is optionally substituted heterocyclic group or a group represented the formula: —C(=Z)W—$R^4$ wherein Z is oxygen atom or sulfur atom: W is oxygen atom or sulfur atom; $R^4$ is optionally substituted alkyl, optionally substituted alkenyl or optionally substituted alkynyl;

$R^2$ and $R^3$ each is independently hydrogen, optionally substituted alkyl, optionally substituted alkoxyalkyl, optionally substituted aminoalkyl, or optionally substituted cycloalkyl; or $R^2$ and $R^3$ taken together form optionally substituted alkylene which may contain a heteroatom(s);

m is an integer of 1 to 2;

A is optionally substituted aromatic carbocyclic group or optionally substituted aromatic heterocyclic group;

provided that when $R^1$ is a group represented by the formula: —C(=Z)W—$R^4$ wherein Z is oxygen atom or sulfur atom; W is oxygen atom or sulfur atom; and $R^4$ is unsubstituted alkyl, $R^2$ and $R^3$ taken together form optionally substituted alkylene which contains a heteroatom(s);

a prodrug, a pharmaceutically acceptable salt or a solvate thereof, (2) the compound according to (1) wherein the following formula

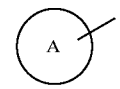

is the formula represented below:

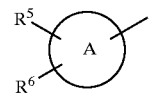

wherein $R^5$ and $R^6$ each is independently hydrogen, alkyl, alkoxy, alkylthio, optionally substituted amino, optionally substituted aryl, optionally substituted aryloxy, cycloalkyl, halogen, hydroxy, nitro, haloalkyl, haloalkoxy, optionally substituted carbamoyl, carboxy, alkoxycarbonyl, alkylsulfinyl, alkylsulfonyl, alkoxyalkyl, alkylthioalkyl, optionally substituted aminoalkyl, alkoxyalkoxy, alkylthioalkoxy, optionally substituted heteroaryl, optionally substituted non-aromatic heterocyclic group, alkoxyiminoalkyl, or a group of the formula: —C(=O)—$R^H$ wherein $R^H$ is hydrogen, alkyl, optionally substituted aryl or optionally substituted non-aromatic heterocyclic group; or $R^5$ and $R^6$ taken together form alkylenedioxy; A is aromatic carbocyclic group or aromatic heterocyclic group;

a prodrug, a pharmaceutically acceptable salt or a solvate thereof, (3) the compound according to (2) wherein $R^5$ is hydrogen, methyl, ethyl, n-propyl, isopropyl, n-butyl, isobutyl, sec-butyl, t-butyl, methoxy, ethoxy, n-propoxy, isopropoxy, n-butoxy, methylthio, ethylthio, n-propylthio, isopropylthio, dimethylamino, acetylamino, N-acetylmethylamino, diethylamino, ethylmethylamino, propylmethylamino, phenyl, phenoxy, fluoro, chloro, bromo, nitro, trifluoromethyl, difluoromethoxy, trifluoromethoxy, N-methylcarbamoyl, methoxycarbonyl, methanesulfinyl, ethanesulfinyl, methanesulfonyl, ethanesulfonyl, acetyl, methoxymethyl, 1-methoxyethyl, 3-pyridyl, morpholino, pyrrolidino, piperidino, 2-oxopyrrolidino, 1-methoxyiminoethyl or morpholinocarbonyl;

$R^6$ is hydrogen, methyl, ethyl, fluoro, chloro, nitro, methoxy or ethoxy; or $R^5$ and $R^6$ taken together form —O—CH$_2$—O—;

A is phenyl, naphthyl, pyridyl or quinolyl;

a prodrug, a pharmaceutically acceptable salt or a solvate thereof, (4) the compound according to (2) wherein $R^5$ and $R^6$ each is independently hydrogen, alkyl, alkoxy, or alkylthio; A is aromatic carbocyclic group;

a prodrug, a pharmaceutically acceptable salt or a solvate thereof, (5) the compound according to any one of (1) to (4) wherein m is 0;

a prodrug, a pharmaceutically acceptable salt or a solvate thereof, (6) the compound according to (5) wherein $R^1$ is optionally substituted heterocyclic group;

a prodrug, a pharmaceutically acceptable salt or a solvate thereof, (7) the compound according to (6) wherein $R^1$ is optionally substituted pyridyl, optionally substituted benzothiazolyl, optionally substituted benzoxazolyl or optionally substituted thiadiazolyl;

a prodrug, a pharmaceutically acceptable salt or a solvate thereof, (8) the compound according to (5) wherein a group represented by the formula: —C(=Z)W—R$^4$ wherein Z is oxygen atom or sulfur atom; W is oxygen atom or sulfur atom; $R^4$ is optionally substituted alkyl, optionally substituted alkenyl or optionally substituted alkynyl;

a prodrug, a pharmaceutically acceptable salt or a solvate thereof, (9) the compound according to (8) wherein Z and W are sulfur atom;

a prodrug, a pharmaceutically acceptable salt or a solvate thereof,

(10) the compound according to any one of (1) to (9) wherein $R^2$ and $R^3$ each is independently methyl, ethyl, propyl or methoxymethyl; or $R^2$ and $R^3$ taken together form ethylene, trimethylene, tetramethylene, pentamethylene or ethyleneoxyethylene;

a prodrug, a pharmaceutically acceptable salt or a solvate thereof,

(11) the compound according to (1) represented by the formula:

<chemical structure> wherein $R^2$ and $R^3$ each is independently optionally substituted alkyl; $R^2$ and $R^3$ taken together form optionally substituted alkylene which may contain heteroatom;

$R^4$ is optionally substituted alkyl, optionally substituted alkenyl or optionally substituted alkynyl;

$R^5$ is alkyl, alkoxy, or optionally substituted amino;

$R^6$ is hydrogen, alkyl, alkoxy, optionally substituted amino or haloalkoxy;

a prodrug, a pharmaceutically acceptable salt or a solvate thereof,

(12) the compound according to (11) wherein $R^4$ is optionally substituted alkyl (substituent is cyano, alkoxy, alkylcarbonyl, carboxy, alkoxycarbonyl, alkenyloxycarbonyl, alkoxyalkoxycarbonyl, optionally substituted carbamoyl (substituent is alkyl or alkoxy), halogen, alkylcarbonyloxy, aryloxy, optionally substituted non-aromatic heterocyclic group (substituent is alkyl), optionally substituted aromatic heterocyclic group (substituent is alkyl or aryl), or a group represented by the formula: —O—R$^1$ wherein $R^1$ is non-aromatic heterocyclic group), alkenyl or alkynyl;

a prodrug of itself, a pharmaceutically acceptable salt thereof or a solvate thereof,

(13) the compound according to (1) wherein A is optionally substituted phenyl, optionally substituted naphthyl, or optionally substituted quinolyl;

a prodrug, a pharmaceutically acceptable salt or a solvate thereof,

(14) a pharmaceutical composition which comprises the compound according to any one of (1) to (13), a prodrug, a pharmaceutically acceptable salt or a solvate thereof,

(15) the pharmaceutical composition according to (14) which has a binding activity to the cannabinoid type 2 receptor,

(16) the pharmaceutical composition according to (15) which has an agonistic activity to the cannabinoid type 2 receptor,

(17) the pharmaceutical composition according to any one of (14) to (16) which is useful as an anti-inflammatory agent,

(18) a method for treating inflammation which comprises administering the pharmaceutical composition according to (1),

(19) use of the compound according to (1) for manufacturing an anti-inflammatory agent,

(20) the pharmaceutical composition according to any one of (14) to (16) which is useful as an immunosuppressive agent,

(21) the pharmaceutical composition according to any one of (14) to (16) which is useful as a nephritis treating agent,

(22) the pharmaceutical composition according to any one of (14) to (16) which is useful as an analgesic agent,

(23) a method for treating immunosuppression which comprises administering the pharmaceutical composition according to (1),

(24) a method for treating nephritis which comprises administering the pharmaceutical composition according to (1),

(25) a method for treating pain which comprises administering the pharmaceutical composition according to (1),

(26) use of the compound according to (1) for manufacturing an immunosuppressive agent,
(27) use of the compound according to (1) for manufacturing a nephritis treating agent,
(28) use of the compound according to (1) for manufacturing an analgesic agent.

The compound represented by the formula (I) comprises,
1) 1,3-thiazine ring is substituted at 3-position with optionally substituted heterocyclic group or a group represented by the formula —C(=Z)W—R$^4$ wherein Z is oxygen atom or sulfur atom; W is oxygen atom or sulfur atom; R$^4$ is optionally substituted alkyl, optionally substituted alkenyl, or optionally substituted alkynyl,
2) 1,3-thiazine ring is substituted at 2-position with a group represented by the formula =N—(CH$_2$)$_m$-A wherein m is an integer of 0 to 2; A is optionally substituted aromatic carbocyclic group or optionally substituted aromatic heterocyclic group, As the compound represented by the formula (I) preferred are the following cases:
1) the substituent on A ring is selected from a group consisting of hydrogen, alkyl, alkoxy, alkylthio, optionally substituted amino, optionally substituted aryl, optionally substituted aryloxy, cycloalkyl, halogen, hydroxy, nitro, haloalkyl, haloalkoxy, optionally substituted carbamoyl, carboxy, alkoxycarbonyl, alkylsulfinyl, alkylsulfonyl, alkoxyalkyl, alkylthioalkyl, optionally substituted aminoalkyl, alkoxyalkoxy, alkylthioalkoxy, optionally substituted heteroaryl, optionally substituted non-aromatic heterocyclic group, or a group represented by the formula: —C(=O)—R$^H$ wherein R$^H$ is hydrogen, alkyl, optionally substituted aryl or optionally substituted non-aromatic heterocyclic group,
2) A ring is substituted with alkylenedioxy at the neighboring positions,
3) m is 0,
4) R$^1$ is optionally substituted pyridyl, optionally substituted benzothiazolyl, optionally substituted benzoxazolyl, or optionally substituted thiazolyl,
5) R$^1$ is a group represented by the formula —C(=Z)W—R$^4$ wherein Z is oxygen atom or sulfur atom; W is oxygen atom or sulfur atom: R$^4$ is optionally substituted alkyl, optionally substituted alkenyl, or optionally substituted alkynyl,
6) R$^1$ is a group represented by the formula —C(=Z)W—R$^4$ wherein Z is oxygen atom or sulfur atom; W is oxygen atom or sulfur atom; R$^4$ is substituted alkyl, optionally substituted alkenyl, or optionally substituted alkynyl,
7) R$^1$ and R$^2$ each is independently methyl, ethyl, propyl, or methoxymethyl; or R$^1$ and R$^2$ taken together form ethylene, trimethylene, tetramethylene, pentamethylene, or ethyleneoxyethylene,
8) A ring is monocyclic aromatic wherein an atom neighboring to the bonding position is substituted with branched alkyl,
9) R$^2$ and R$^3$ taken together form optionally substituted alkylene which may contain a heteroatom(s).

The meanings of each term used in compound of the formula (I) are explained below. Each term employed alone or in the combination with other terms is used to express the same meaning.

The term "alkyl" includes a C1–C10 straight or branched alkyl, for example, methyl, ethyl, n-propyl, isopropyl, n-butyl, isobutyl, sec-butyl, tert-butyl, n-pentyl, isopentyl, neopentyl, n-hexyl, n-heptyl, n-octyl, n-noyl, n-decyl or the like. Preferred is a C1–C4 straight or branched alkyl, for example, methyl, ethyl, n-propyl, isopropyl, n-butyl, isobutyl, sec-butyl and tert-butyl.

The term "alkenyl" includes a C2–C8 straight or branched alkenyl which is the above "alkyl" having one or more double bond, for example, vinyl, 1-propenyl, allyl, isopropenyl, 1-butenyl, 2-butenyl, 3-butenyl, 2-pentenyl, 1,3-butadienyl, 3-methyl-2-butenyl or the like.

The term "alkynyl" includes a C2–C8 straight or branched alkynyl which is the above "alkyl" having one or more triple bond, for example, etynyl or the like.

The term "alkoxy" includes an oxygen atom substituted with the above "alkyl", for example, methoxy, ethoxy, n-propoxy, isopropoxy, n-butoxy, isobutoxy, sec-butoxy, tert-butoxy, n-pentyloxy, n-hexyloxy, n-heptyloxy, n-octyloxy or the like. Preferred is a C1–C4 straight or branched alkoxy, for example, methoxy, ethoxy, n-propoxy, isopropoxy, n-butoxy, isobutoxy, sec-butoxy and tert-butoxy.

The term "alkoxyalkyl" includes the above "alkyl" substituted with the above "alkoxy", for example, methoxymethyl, ethoxymethyl, n-propoxymethyl, 1-methoxyethyl, 2-methoxyethyl, 1-ethoxyethyl, 2-ethoxyethyl, 1-n-propoxyethyl, 2-n-propoxyethyl, 1-methoxy-n-propyl, 2-methoxy-n-propyl, 3-methoxy-n-propyl, 1-ethoxy-n-propyl, 2-ethoxy-n-propyl, 3-ethoxy-n-propyl, 1-n-propoxy-n-propyl, 2-n-propoxy-n-propyl, 3-n-propoxy-n-propyl or the like.

Examples of substituents of "optionally substituted amino" include alkyl (e.g., methyl, ethyl, n-propyl, isopropyl or the like), acyl (e.g., formyl, acetyl, propionyl, benzoyl or the like) or the like. A nitrogen atom of an amino group may be mono- or di-substituted with these substituents.

Examples of "optionally substituted amino" include amino, methylamino, ethylamino, n-propylamino, isopropylamino, dimethylamino, diethylamino, ethylmethylamino, acetylamino, N-acetylmethylamino, propylmethylamino or the like.

The term "optionally substituted aminoalkyl" includes the above "alkyl" substituted with the above "optionally substituted amino", for example, aminomethyl, methylaminomethyl, ethylaminomethyl, n-propylaminomethyl, isopropylaminomethyl, N,N-dimethylaminomethyl, N,N-diethylaminomethyl, N-ethyl-N-methylaminomethyl, acetylaminomethyl, N-acetylmethylaminomethyl, N-propyl-N-methylaminomethyl or the like.

The term "cycloalkyl" includes C3–C10 saturated carbocyclic group, for example, cyclopropyl, cyclobutyl, cyclopentyl, cyclohexyl, cycloheptyl, cyclooctyl or the like. Preferred is C3–C6 cycloalkyl, for example, cyclopropyl, cyclobutyl, cyclopentyl, cyclohexyl.

The term "alkylene which may contain heteroatom" includes a C2–C10 straight or branched alkylene which may contain one to three heteroatom(s), for example, ethylene, trimethylene, tetramethylene, pentamethylene, methylenedioxy, ethylenedioxy, ethyleneoxyethylene or the like. Especially preferred is C3–C5 straight alkylene which may contain one heteroatom, for example, tetramethylene, pentamethylene, ethyleneoxyethylene, ethyleneaminoethylene, ethylenethioethylene.

The term "aromatic carbocyclic group" includes a C6–C14 aromatic carbocyclic group, for example, phenyl, naphthyl (1-naphthyl, 2-naphthyl) anthryl, phenanthryl or the like. Preferred is phenyl or naphthyl (1-naphthyl, 2-naphthyl).

The term "aromatic heterocyclic group" includes a C1–C14 monocyclic aromatic heterocyclic group or a C1–C14 aromatic heterocyclic group containing two or three fused rings, each containing one to four nitrogen atom(s), oxygen atom(s) and/or sulfur atom(s), for example, furyl (e.g., 2-furyl, 3-furyl), thienyl (e.g., 2-thienyl, 3-thienyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), triazolyl (e.g., 1,2,4-triazol-1-yl, 1,2,4-triazol-3-yl, 1,2,4-triazol-4-yl), tetrazolyl (e.g., 1-tetrazolyl, 2-tetrazolyl, 5-tetrazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), thiazolyl (e.g., 2-thiazolyl, 4-thiazolyl, 5-thiazolyl), thiadiazolyl, isothiazolyl (e.g., 3-isothiazolyl, 4-isothiazolyl, 5-isothiazolyl), pyridyl (e.g., 2-pyridyl, 3-pyridyl, 4-pyridyl), pyridazinyl (e.g., 3-pyridazinyl, 4-pyridazinyl), pyrimidinyl (e.g., 2-pyrimidinyl, 4-pyrimidinyl, 5-pyrimidinyl), furazanyl (e.g., 3-furazanyl), pyrazinyl (e.g., 2-pyrazinyl), oxadiazolyl (e.g., 1,3,4-oxadiazol-2-yl), benzofuryl (e.g., 2-benzo[b]furyl, 3-benzo[b]furyl, 4-benzo[b]furyl, 5-benzo[b]furyl, 6-benzo[b]furyl, 7-benzo[b]furyl), benzothienyl (e.g., 2-benzo[b]thienyl, 3-benzo[b]thienyl, 4-benzo[b]thienyl, 5-benzo[b]thienyl, 6-benzo[b]thienyl, 7-benzo[b]thienyl), benzimidazolyl (e.g., 1-benzimidazolyl, 2-benzimidazolyl, 4-benzimidazolyl, 5-benzimidazolyl), dibenzofuryl, benzoxazolyl, quinoxalinyl (e.g., 2-quinoxalinyl, 5-quinoxalinyl, 6-quinoxalinyl), cinnolinyl (e.g., 3-cinnolinyl, 4-cinnolinyl, 5-cinnolinyl, 6-cinnolinyl, 7-cinnolinyl, 8-cinnolinyl), quinazolinyl (e.g., 2-quinazolinyl, 4-quinazolinyl, 5-quinazolinyl, 6-quinazolinyl, 7-quinazolinyl, 8-quinazolinyl), quinolyl (e.g., 2-quinolyl, 3-quinolyl, 4-quinolyl, 5-quinolyl, 6-quinolyl, 7-quinolyl, 8-quinolyl), phthalazinyl (e.g., 1-phthalazinyl, 5-phthalazinyl, 6-phthalazinyl), isoquinolyl (e.g., 1-isoquinolyl, 3-isoquinolyl, 4-isoquinolyl, 5-isoquinolyl, 6-isoquinolyl, 7-isoquinolyl, 8-isoquinolyl), puryl, pteridinyl (e.g., 2-pteridinyl, 4-pteridinyl, 6-pteridinyl, 7-pteridinyl), carbazolyl, phenanthridinyl, acridinyl (e.g., 1-acridinyl, 2-acridinyl, 3-acridinyl, 4-acridinyl, 9-acridinyl), indolyl (e.g., 1-indolyl, 2-indolyl, 3-indolyl, 4-indolyl, 5-indolyl, 6-indolyl, 7-indolyl), isoindolyl, phenazinyl (e.g., 1-phenazinyl, 2-phenazinyl) or phenothiadinyl (e.g., 1-phenothiadinyl, 2-phenothiadinyl, 3-phenothiadinyl, 4-phenothiadinyl) or the like.

Especially preferred is pyridyl, quinolyl (especially 5-quinolyl) or isoqunolyl as "aromatic heterocyclic group" of A.

The term "heterocyclic group" includes a C1–C14 monocyclic heterocyclic group or a C1–C14 heterocyclic group containing two or three fused rings, each containing one to four nitrogen atom(s), oxygen atom(s) and/or sulfur atom(s), for example, above "aromatic heterocyclic group" or non-aromatic heterocyclic group.

The term "non-aromatic heterocyclic group" includes a C1–C14 monocyclic non-aromatic heterocyclic group or C1–C14 non-aromatic heterocyclic group containing two or three fused rings, each containing one to four nitrogen atom(s), oxygen atom(s) and/or sulfur atom(s), for example, 1-pyrrolinyl, 2-pyrrolinyl, 3-pyrrolinyl, pyrrolidino, 2-pyrrolidinyl, 3-pyrrolidinyl, 1-imidazolinyl, 2-imidazolinyl, 4-imidazolinyl, 1-imidazolidinyl, 2-imidazolidinyl, 4-imidazolidinyl, 1-pyrazolinyl, 3-pyrazolinyl, 4-pyrazolinyl, 1-pyrazolidinyl, 3-pyrazolidinyl, 4-pyrazolidinyl, piperidino, 2-piperidyl, 3-piperidyl, 4-piperidyl, piperazino, 2-piperazinyl, 2-morpholinyl, 3-morpholinyl, morpholino, tetrahydropyranyl or the like. Preferred is morpholino, pyrrolidino, piperidino or piperazino.

When $R^1$ is heterocyclic group, preferred is aromatic heterocyclic group, especially monocyclic or dicyclic aromatic heterocyclic group. Especially preferred is pyridyl (e.g., pyridin-2-yl or the like), thiazolyl (e.g., thiazol-2-yl or the like), benzothiazolyl (e.g., benzothiazol-2-yl or the like), benzoxazolyl (e.g., benzoxazol-2-yl or the like).

Examples of the substituents of "optionally substituted heterocyclic group", "optionally substituted alkyl", "optionally substituted alkenyl", "optionally substituted alkynyl", "optionally substituted alkoxyalkyl", "optionally substituted cycloalkyl", "optionally substituted alkylene which may contain heteroatom", "optionally substituted aromatic carbocyclic group" and "optionally substituted aromatic heterocyclic group" include alkyl, alkoxy, alkenyloxy, alkylthio, optionally substituted amino, optionally substituted aryl, optionally substituted heteroaryl, optionally substituted non-aromatic heterocyclic group, optionally substituted aryloxy, cycloalkyl, halogen, hydroxy, nitro, haloalkyl, haloalkoxy, optionally substituted carbamoyl, carboxy, alkoxycarbonyl, alkenyloxycarbonyl, alkylsulfinyl, alkylsulfonyl, alkoxyalkyl, alkylthioalkyl, optionally substituted aminoalkyl, alkoxyalkoxy, alkoxyalkoxycarbonyl, alkylthioalkoxy, optionally substituted heteroaryl, optionally substituted non-aromatic heterocyclic group, alkoxyiminoalkyl, a group of the formula: —C(=O)—$R^H$ wherein $R^H$ is hydrogen, alkyl, optionally substituted aryl or optionally substituted non-aromatic heterocyclic group), arylsulfonyl (e.g., benzenesulfonyl or the like), cyano, hydroxy amino, aralkyl (e.g., benzyl or the like), mercapto, hydrazino, amidino, guanidino, isocyano, isocyanato, thiocyanato, isothiocyanato, sulfamoyl, formyloxy, haloformyl, oxalo, thioformyl, thiocarboxy, dithiocarboxy, thiocarbamoyl, sulfino, sulfo, sulfoamino, azido, ureido, amidino, guanidino, oxo, thioxo, alkylcarbonyloxy, alkylenedioxy, a group represented by the formula: —O—$R^I$ (wherein $R^I$ is non-aromatic heterocyclic group), aralkyloxy, aralkylthio, aralkylamino or the like.

These substituents may substitute at any substitutable positions. A divalent group described above may substitute at the same or different positions on the ring.

As the substituent of "optionally substituted heterocyclic group" of $R^1$, among the substituents examplified above, especially preferred is alkyl (e.g., methyl or the like), alkoxy (e.g., methoxy or the like), alkylthio (e.g., methylthio or the like), optionally substituted amino, cycloalkyl, halogen, hydroxy, nitro, haloalkyl, haloalkoxy, optionally substituted carbamoyl, carboxy, alkoxycarbonyl, optionally substituted aminoalkyl, a group represented by the formula: —C(=O)—$R^H$ wherein $R^H$ is hydrogen or alkyl, cyano, hydroxyamino, mercapto or the like.

As the substituents of "optionally substituted alkyl", "optionally substituted alkenyl", "optionally substituted alkynyl", "optionally substituted alkoxyalkyl" and "optionally substituted cycloalkyl" of $R^4$, among the substituents examplified above, especially preferred is alkoxy (e.g., methoxy or the like), alkenyloxy (e.g., vinyloxy or the like), optionally substituted heteroaryl (e.g., heteroaryl (e.g. isoxazolyl, oxazolyl or the like) optionally substituted with alkyl (e.g., methyl, isopropyl, isobutyl, tert-butyl or the like) or aryl (e.g., phenyl)), non-aromatic heterocyclic group (e.g., morpholino, 4,5-dihydroisoxazole-3-yl, 1,3-dioxolane or the like) optionally substituted with alkyl (e.g., methyl), aryloxy (e.g., phenoxy or the like), halogen (e.g., fluoro), hydroxy, haloalkyl (e.g., trifluoromethyl or the like), optionally substituted carbamoyl (e.g., unsubstituted carbamoyl, N,N-dimethylcarbamoyl, N-methyl-N-methoxycarbamoyl or the like), carboxy, alkoxycarbonyl (e.g., methoxycarbonyl, ethoxycarbonyl, n-propoxycarbonyl, isopropoxycarbonyl, tert-butoxycarbonyl or the like), alkenyloxycarbonyl (e.g., vinyloxycarbonyl, allyloxycarbonyl or the like), alkoxyalkoxycarbonyl (e.g., 2-methoxyethyloxycarbonyl or the like), a group represented by the formula: —C(=O)—R$^H$ wherein R$^H$ is hydrogen or alkyl (e.g., formyl, acetyl or the like), cyano, oxo, alkylcarbonyloxy (e.g., acetyloxy or the like), alkylenedioxy (e.g., ethylenedioxy or the like), a group represented by the formula: —O—R$^I$ wherein R$^I$ is non-aromatic heterocyclic group (e.g., tetrahydropyran-2-yloxy or the like), or the like.

As the substituents of "optionally substituted alkylene which may contain heteroatom", "optionally substituted aromatic carbocyclic group", and "optionally substituted aromatic heterocyclic group" of A, among the substituents exemplified above, especially preferred is alkyl (e.g., methyl, ethyl, isopropyl, sec-butyl or the like), alkoxy (e.g., methoxy, ethoxy, isopropoxy or the like), optionally substituted amino (e.g., dimethylamino, diethylamino, ethylmethylamino or the like), haloalkyl (e.g., trifluoromethyl or the like), haloalkoxy (e.g., trifluoromethoxy or the like), aralkyl (e.g., benzyl or the like). The substituent of "alkylene which may contain heteroatom" and "aromatic heterocyclic group" may substituted on heteroatom (nitrogen atom).

Especially when A is monocyclic aromatic (e.g., phenyl, furyl, thienyl, pyrrolyl, imidazolyl, oxazolyl, isooxazolyl, thiazolyl, pyridyl, pyridazinyl, pyrimidinyl, pyrazinyl or the like), preferred is that an atom neighboring to the bonding position is substituted with branched alkyl. The branched alkyl include C1–C10 branched alkyl, for example, isopropyl, isobutyl, sec-butyl, tert-butyl, isopentyl, neopentyl, tert-pentyl, isohexyl or the like. Especially preferred is C3 or C4 branched alkyl, for example, isopropyl, isobutyl, sec-butyl, or tert-butyl.

The term "halogen" includes fluoro, chloro, bromo and iodo. Preferred is fluoro, chloro or bromo.

The term "alkenyloxy" includes an oxygen atom substituted with the above "alkenyl", for example, vinyloxy, 1-propenyloxy, allyloxy, isopropenyloxy, 1-butenyloxy, 2-butenyloxy, 3-butenyloxy, 2-pentenyloxy, 1,3-butadienyloxy, 3-methyl-2-butenyoxy or the like.

The term "alkylthio" includes a sulfur atom substituted with the above "alkyl", for example, methylthio, ethylthio, n-propylthio, isopropylthio, n-butylthio, isobutylthio, sec-butylthio, t-butylthio, n-pentylthio, n-hexylthio or the like. Preferred is a C1–C4 straight or branched alkylthio, for example, methylthio, ethylthio, n-propylthio, isopropylthio, n-butylthio, isobutylthio, sec-butylthio and t-butylthio.

The term "aryl" includes above "aromatic carbocyclic group", for example, phenyl, naphthyl (1-naphthyl or 2-naphthyl), anthryl, phenanthryl or the like. Especially preferred is phenyl or naphthyl (1-naphthyl or 2-naphthyl).

The term "heteroaryl" includes above "aromatic hetercyclic group" for example, furyl, thienyl, pyrrolyl, imidazolyl, pyrazolyl, triazolyl, tetrazolyl, oxazolyl, isoxazolyl, thiazolyl, thiadiazolyl, isothiazolyl, pyridyl, pyridazinyl, pyrimidinyl, furazanyl, pyrazinyl, benzofuryl, benzothienyl, benzimidazolyl, dibenzofuryl, benzoxazolyl, quinoxalinyl, cinnolinyl, quinazolinyl, quinolinyl, phthalazinyl, isoquinolinyl, puryl, pteridinyl, carbazolyl, phenanthridinyl, acridinyl, indolyl, isoindolyl, phenazinyl, phenothiadinyl or the like. Preferred is pyridine, quinoline or isoquinoline.

The term "aryloxy" includes an oxygen atom substituted with the above "aryl", for example, phenoxy, naphthoxy (e.g., 1-naphthoxy, 2-naphthoxy or the like), anthryloxy (e.g., 1-anthryloxy, 2-anthryloxy or the like), phenanthryl (e.g., 1-phenanthryl, 2-phenanthryl or the like) or the like.

The term "haloalkyl" includes the above "alkyl" substituted with one or more halogen, especially preferred is C1–C3 haloalkyl, for example, trifluoromethyl, chloromethyl, dichloromethyl, difluoromethyl, 1-chloroethyl, 2-chloroethyl, 1,1-dichloroethyl. 1.2-dichloroethyl, 2.2-dichloroethyl, 2.2.2-trichloroethyl or the like.

The term "haloalkoxy" includes oxygen atom substituted with the above "haloalkyl", for example, dichloromethoxy, difluoromethoxy, trifluoromethoxy, trifluoroethoxy (2,2.2-trifluoroethoxy or the like) or the like.

Examples of the substituents of "optionally substituted carbamoyl" include alkyl (e.g., methyl, ethyl, n-propyl, isopropyl or the like), acyl (e.g., formyl, acetyl, propionyl, benzoyl or the like) or the like. The nitrogen atom of carbamoyl group may be mono- or di-substituted with these substituents. Preferred as "optionally substituted carbamoyl" is carbamoyl, N-methylcarbamoyl or N-ethylcarbamoyl.

The term "alkoxycarbonyl" include carbonyl substituted with the above "alkoxy", for example, methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl, n-pentyloxycarbonyl, n-hexyloxycarbonyl, n-heptylcarbonyl, n-octyloxycarbonyl or the like.

The term "alkenyloxycarbonyl" includes carbonyl substituted with the above "alkenyloxy", for example, vinyloxycarbonyl, 1-propenyloxycarbonyl, allyloxycarbonyl, isopropenyloxycarbonyl, 1-butenyloxycarbonyl, 2-butenyloxycarbonyl, 3-butenyloxycarbonyl, 2-pentenyloxycarbonyl, 1,3-butadienyloxycarbonyl, 3-methyl-2-butenyloxycarbonyl or the like.

The term "alkylsulfinyl" includes sulfinyl substituted with the above "alkyl". Preferred is methanesulfinyl, ethanesulfinyl or the like.

The term "alkylsulfonyl" includes sulfonyl substituted with the above "alkyl". Preferred is methanesulfonyl, ethanesulfonyl or the like.

The term "alkylthioalkyl" includes the above "alkyl" substituted with the above "alkylthio", for example, methylthiomethyl, ethylthiomethyl, n-propylthiomethyl, 1-methylthioethyl, 2-methylthioethyl, 1-ethylthioethyl, 2-ethylthioethyl, 1-n-propylthioethyl, 2-n-propylthioethyl, 3-n-propylthioethyl, 1-methylthio-n-propyl, 2-methylthio-n-propyl, 3-methylthio-n-propyl, 1-ethylthio-n-propyl, 2-ethylthio-n-propyl, 3-ethylthio-n-propyl, 1-n-propylthio-n-propyl, 2-n-propylthio-n-propyl, 3-n-propylthio-n-propyl or the like.

The term "alkoxyalkoxy" includes the above "alkoxy" substituted with the above "alkoxy", for example, methoxymethoxy, ethoxymethoxy, n-propoxymethoxy, isopropoxymethoxy, 1-methoxyethoxy, 2-methoxyethoxy or the like.

The term "alkoxyalkoxycarbonyl" includes carbonyl substituted with the above "alkoxyalkoxy", for example, methoxymethoxycarbonyl, ethoxymethoxycarbonyl, n-propoxymethoxycarbonyl, isopropoxymethoxycarbonyl, 1-methoxyethoxycarbonyl, 2-methoxyethoxycarbonyl or the like.

The term "alkylthioalkoxy" includes the above "alkoxy" substituted with the above "alkylthio", for example, methylthiomethoxy, ethylthiomethoxy, n-propylthiomethoxy, isopropylthiomethoxy, 1-methylthioethoxy, 2-methoxyethoxy or the like.

The term "alkoxyiminoalkyl" include the above "alkyl" substituted with alkoxyimino, for example, methoxyiminomethyl, ethoxyiminomethyl, 1-methoxyiminoethyl or the like.

Examples of a group of the formula: —C(=O)—R$^H$ wherein R$^H$ is hydrogen, alkyl, optionally substituted aryl or optionally substituted non-aromatic heterocyclic group include formyl, acetyl, benzoyl, toluoyl, morpholinocarbonyl or the like.

The term "arylsulfonyl" includes sulfonyl substituted with the above "aryl", especially preferred is benzenesulfonyl.

The term "aralkyl" includes the above "alkyl" substituted with the above "aryl", for example, benzyl, phenylethyl (e.g., 1-phenylethyl, 2-phenylethyl), phenylpropyl (e.g., 1-phenylpropyl, 2-phenylpropyl, 3-phenylpropyl or the like), naphthylmethyl (e.g., 1-naphthylmethyl, 2-naphthylmethyl or the like) or the like.

The term of "alkylcarbonyloxy" includes carbonyloxy substituted with the above "alkyl", for example methylcarbonyloxy, ethylcarbonyloxy, n-propylcarbonyloxy, isopropylcarbonyloxy, n-butylcarbonyloxy, isobutylcarbonyloxy, sec-butylcarbonyloxy, tert-butylcarbonyloxy, n-pentylcarbonyloxy, isopentylcarbonyloxy, neopentylcarbonyloxy, tert-pentylcarbonyloxy, n-hexylcarbonyloxy, isohexylcarbonyloxy, n-heptylcarbonyloxy, n-octylcarbonyloxy, n-nonylcarbonyloxy, n-dodecylcarbonyloxy or the like.

The term of "alkylenedioxy" includes dioxy substituted with C1–C6 straight or branched alkylene, and can substitute on the same or different atom. For example, preferred is methylenedioxy (—O—CH$_2$—O—), ethylenedioxy (—O—CH$_2$—CH$_2$—O—), propylenedioxy (—O—CH$_2$—CH$_2$—CH$_2$—O—) or the like.

Examples of a group represented by the formula: —O—R$^I$ wherein R$^I$ is non-aromatic heterocyclic group include, 1-pyrrolynyloxy, 2-pyrrolynyloxy, 3-pyrrolynyloxy, pyrrolidinoxy, 2-pyrrolidinoxy, 3-pyrrolidinoxy, 1-imidazolynyloxy, 2-imidazolynyloxy, 4-imidazolynyloxy, 1-pyrazolynyloxy, 3-pyrazolynyloxy, 4-pyrazolynyloxy, 1-pyrazolydinyloxy, 3-pyrazolydinyloxy, 4-pyrazolydinyloxy, piperidinoxy, 2-piperidinoxy, 3-piperidinoxy, 4-piperidinoxy, piperadinoxy, 2-piperadinoxy, 2-morpholinyloxy, 3-morpholinyloxy, morpholinoxy, teterahydropyran-2-yloxy or the like.

The term "aralkyloxy" includes an oxygen atom substituted with the above "aralkyl", for example, benzyloxy, phenylethyloxy (e.g., 1-phenylethyloxy, 2-phenylethyloxy), phenylpropoxy (e.g., 1-phenylpropyloxy, 2-phenylpropyloxy, 3-phenylpropyloxy or the like), naphthylmethoxy (e.g., 1-naphthylmethoxy, 2-naphthylmethoxy or the like) or the like.

The term "aralkylthio" includes a sulfur atom substituted with the above "aralkyl", for example, benzylthio, phenylethylthio (e.g., 1-phenylethylthio, 2-phenylethylthio), phenylpropylthio (e.g., 1-phenylpropylthio, 2-phenylpropylthio, 3-phenylpropylthio or the like), naphthylmethylthio (e.g., 1-naphthylmethylthio, 2-naphthylmethylthio or the like) or the like.

The term "aralkylamino" includes a nitrogen atom substituted with one or two of the above "aralkyl", for example, benzylamino, phenylethylamino (e.g., 1-phenylethylamino, 2-phenylethylamino), phenylpropylamino (e.g., 1-phenylpropylamino, 2-phenylpropylamino, 3-phenylpropylamino), naphthylmethylamino (e.g., 1-naphthylmethylamino, 2-naphthylmethylamino or the like), dibenzylamino or the like.

The tem "m" is an integer of 0 to 2. Preferred as "m" is 0.

The term "an agonistic activity to a cannabinoid type 2 receptor" includes agonizing a cannabinoid type 2 receptor.

BEST MODE FOR CARRYING OUT THE INVENTION

The compounds of the present invention can be prepared in accordance with the following processes.

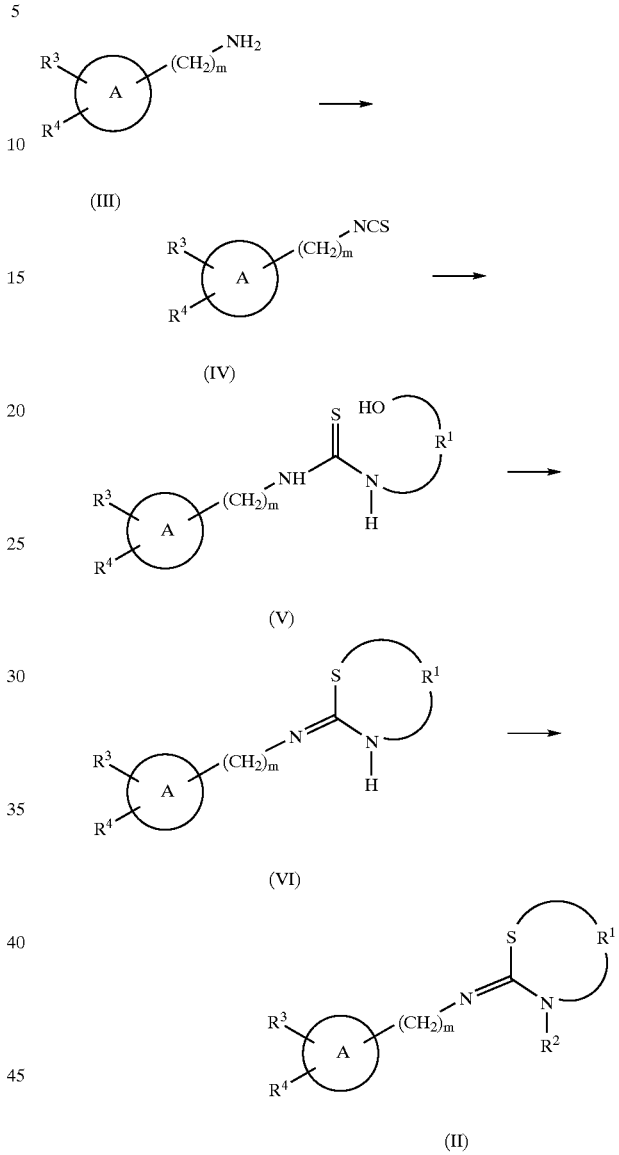

wherein each symbol as defined above.

Process 1

This is a process for producing a compound of the formula (IV) which comprises converting amino group of a compound of the formula (III) to isothiocyanic acid ester (isothiocyanate).

A method for converting amino group to isothio cyanic acid ester (isothiocyanate) includes the following methods; 1) a method which comprises reacting the starting compound with carbon disulfide in the presence of a base such as ammonia (NH$_3$, NH$_4$OH), triethylamine (Et$_3$N) and reacting the obtained dithiocarbamate with ethyl chlorocarboxylate (ClCO$_2$Et) and triethylamine (Et$_3$N), 2) a method which comprises reacting the above dithiocarbamate with acid metalate such as lead nitrate or the like, 3) a method of reacting thiophosgene (CSCl$_2$) and 4) a method of reacting thiocarbonyldiimidazole or the like.

In the above 1), a base (1.0 to 1.5 mole equivalent) and carbon disulfide (1.0 to 1.5 mole equivalent) are added to a solution of a compound of the formula (III) in an aprotic solvent (e.g., diethylether, tetrahydrofuran, dimethylformamide, benzene, toluene, dichloromethane, chloroform or the like) and the mixture is stirred for 0.5 to 10 hours. After that, ethyl chlorocarboxylate (1.0 to 1.5 mole equivalent) and triethylamine (1.0 to 1.5 mole equivalent) are added thereto and the mixture is stirred in the same solvent for 0.5 to 10 h. The reaction temperature is preferably 0 to 100° C., especially 0° C. to room temperature.

In the above 3), thiophosgene (1.0 to 1.5 mole equivalent) is added to a solution of the compound of the formula (III) in an aprotic solvent (e.g., diethylether, tetrahydrofuran, dimethylformamide, benzene, toluene, dichloromethane, chloroform or the like) and stirred for 0.5 to 10 h. The reaction temperature is preferably 0 to 100° C., especially 0° C. to room temperature.

In the above 4), thiocarbonyldiimidazole (1.0 to 1.5 mole equivalent) is added to a solution of the compound of the formula (III) in an aprotic solvent (e.g., diethylether, tetrahydrofuran, dimethylformamide, benzene, toluene, dichloromethane, chloroform or the like) and stirred for 0.5 to 10 h. The reaction temperature is preferably 0 to 100° C., especially 0° C. to room temperature.

Examples of the compound of the formula (III) wherein m is 0 include aniline, 2-methylaniline, 2-ethylaniline, 2-n-propylaniline, 2-isopropylaniline, 2-n-butylaniline, 2-sec-butylaniline, 2-t-butylaniline, 3-methylaniline, 3-isopropylaniline, 3-isopropyl-4-methylaniline, 3-t-butylaniline, 4-methylaniline, 4-i-propylaniline, 2,6-dimethylaniline, 2,3-dimethylaniline, 2,4-dimethylaniline, 3,4-diethylaniline, 2,5-dimethylaniline, 3,4-dimethylaniline, 3,5-dimethylaniline, 2,6-diethylaniline, 2,6-di-isopropylaniline, 2-methoxyaniline, 2-ethoxyaniline, 2-isopropoxyaniline, 3-methoxyaniline, 3,5-dimethoxyaniline, 3-n-butoxyaniline, 4-n-butoxyaniline, 4-ethoxyaniline, 3,4-dimethoxyaniline, 2-methylthioaniline, 2-ethylthioaniline, 2-isopropylthioaniline, 2-N,N-dimethylaminoaniline, 2-phenylaniline, 3-phenylaniline, 4-phenoxyaniline, 2-cyclohexylaniline, 2-cyclopentylaniline, 2-nitroaniline, 2,4-dinitroaniline, 2-fluoroaniline, 2-chloroaniline, 4-chloroaniline, 2,3-dichloroaniline, 3,4-dichloroaniline, 2-isopropyl-4-nitroaniline, 2-isopropyl-6-nitroaniline, 2-hydroxyaniline, 2-N,N-dimethylaminocarbonylaniline, 2-N-acetylaniline, 2-(1-ethylpropyl)aniline, 2-isopropyl4-methylaniline, 2-isopropyl-4-hydroxyaniline, 2-isopropyl-4-chloroaniline, 2-isopropyl-4-aminoaniline, 2-isopropyl-5-methylaniline, 2-isopropyl-5-hydroxy aniline, 2-isopropyl-5-chloroaniline, 4-chloro-3-methylaniline. 3,4-methylenedioxyaniline or the like.

Examples of the compound of the formula (III) wherein m is 1 include benzylamine, 2-methylbenzylamine, 2-ethylbenzylamine, 2-n-propylbenzylamine, 2-isopropylbenzylamine, 2-n-butylbenzylamine, 2-sec-butylbenzylamine, 2-t-butylbenzylamine, 3-methylbenzylamine, 3-isopropylbenzylamine, 3-isopropyl-4-methylbenzylamine, 3-t-butylbenzylamine, 4-methylbenzylamine, 4-i-propylbenzylamine, 2,6-dimethylbenzylamine, 2,3-dimethylbenzylamine, 2,4-dimethylbenzylamine, 3,4-diethylbenzylamine, 2,5-dimethylbenzylamine, 3,4-dimethylbenzylamine, 3,5-dimethylbenzylamine, 2,6-diethylbenzylamine, 2,6-di-isopropylbenzylamine, 2-methoxybenzylamine, 2-ethoxybenzylamine, 2-isopropoxybenzylamine, 3-methoxybenzylamine, 3,5-dimethoxybenzylamine, 3-n-butoxybenzylamine, 4-n-butoxybenzylamine, 4-ethoxybenzylamine, 3,4-dimethoxybenzylamine, 2-methylthiobenzylamine, 2-ethylthiobenzylamine, 2-isopropylthiobenzylamine, 2-N,N-dimethylaminobenzylamine, 2-phenylbenzylamine, 3-phenylbenzylamine, 4-phenoxybenzylamine, 2-cyclohexylbenzylamine, 2-cyclopentylbenzylamine, 2-nitrobenzylamine, 2,4-dinitrobenzylamine, 2-fluorobenzylamine, 2-chlorobenzylamine, 4-chlorobenzylamine, 2,3-dichlorobenzylamine, 3,4-dichlorobenzylamine, 2-i-propyl-4-nitrobenzylamine, 2-i-propyl-6-nitrobenzylamine, 2-hydroxybenzylamine, 2-N,N-dimethylaminocarbonylbenzylamine, 2-N-acetylbenzylamine, 2-(1-ethylpropyl)benzylamine, 2-isopropyl4-methylbenzylamine, 2-isopropyl-4-hydroxybenzylamine, 2-isopropyl-4-chlorobenzylamine, 2-isopropyl-4-aminobenzylamine, 2-isopropyl-5-methylbenzylamine, 2-isopropyl-5-hydroxybenzylamine, 2-isopropyl-5-chlorobenzylamine, 4-chloro-3-methylbenzylamine, 3,4-methylenedioxybenzylamine or the like.

Examples of the compound of the formula (III) wherein m is 2 include phenethylamine, 2-methylphenethylamine, 2-ethylphenethylamine, 2-n-propylphenethylamine, 2-isopropylphenethylamine, 2-n-butylphenethylamine, 2-sec-butylphenethylamine, 2-t-butylphenethylamine, 3-methylphenethylamine, 3-isopropylphenethylamine, 3-isopropyl-4-methylphenethylamine, 3-t-butylphenethylamine, 4-methylphenethylamine, 4-isopropylphenethylamine, 2,6-dimethylphenethylamine, 2,3-dimethylphenethylamine, 2,4-dimethylphenethylamine, 3,4-diethylphenethylamine, 2,5-dimethylphenethylamine, 3,4-dimethylphenethylamine, 3,5-dimethylphenethylamine, 2,6-diethylphenethylamine, 2,6-di-isopropylphenethylamine, 2-methoxyphenethylamine, 2-ethoxyphenethylamine, 2-i-propoxyphenethylamine, 3-methoxyphenethylamine, 3,5-dimethoxyphenethylamine, 3-n-butoxyphenethylamine, 4-n-butoxyphenethylamine, 4-ethoxyphenethylamine, 3,4-dimethoxyphenethylamine, 2-methylthiophenethylamine, 2-ethylthiophenethylamine, 2-isopropylthiophenethylamine, 2-N,N-dimethylaminophenethylamine, 2-phenylphenethylamine, 3-phenylphenethylamine, 4-phenoxyphenethylamine, 2-cyclohexylphenethylamine, 2-cyclopentylphenethylamine, 2-nitrophenethylamine, 2,4-dinitrophenethylamine, 2-fluorophenethylamine, 2-chlorophenethylamine, 4-chlorophenethylamine, 2,3-dichlorophenethylamine, 3,4-dichlorophenethylamine, 2-i-propyl-4-nitrophenethylamine, 2-isopropyl-6-nitrophenethylamine, 2-hydroxyphenethylamine, 2-N,N-dimethylaminocarbonylphenethylamine, 2-N-acetylphenethylamine, 2-(1-ethylpropyl)phenethylamine, 2-isopropyl4-methylphenethylamine, 2-isopropyl-4-hydroxyphenethylamine, 2-isopropyl-4-chlorophenethylamine, 2-isopropyl-4-aminophenethylamine, 2-isopropyl-5-methylphenethylamine, 2-isopropyl-5-hydroxyphenethylamine, 2-isopropyl-5-chlorophenethylamine, 4-chloro-3-methylphenethylamine, 3,4-methylenedioxyphenethylamine or the like.

Process 2

This is a process for producing a compound of the formula (V) which comprises reacting an isothiocyanate of the compound of the formula (IV) with $NH_2$—$CH_2C(R^2)R^3CH_2$—OH.

This process can be carried out in an aprotic solvent (e.g., diethylether, tetrahydrofuran, dimethylformamide, benzene, toluene, dichloromethane, chloroform or the like).

The reaction temperature is preferably 0 to 100° C., especially 0° C. to room temperature. The reaction time is 0.5 to 10 h.

The amount of $NH_2—CH_2C(R^2)R^3CH_2—OH$ is 1.0 to 1.5 mole equivalent to that of the compound of the formula (IV).

Examples of $NH_2—CH_2C(R^2)R^3CH_2—OH$ include 3-aminopropanol, 3-amino-2,2-dimethylethanol, 3-amino-1-methylproanol, 3-amino-2-methylpropanol, 3-amino-3-methylpropanol, 3-amino-2,2-diethylpropanol, 1-aminomethyl-1-hydroxymethylcyclopropane, 1-aminomethyl-1-hydroxymethylcyclopentane, 1-aminomethyl-1-hydroxymethylcyclohexane, 1-aminomethyl-1-hydroxymethyl4-oxacyclohexane or the like.

Process 3

This is a process for producing a compound of the formula (VI) which comprises the cyclization of the compound of the formula (V).

A method of the cyclization includes 1) a method which comprises reacting with diethylazodicarboxylate (DEAD) and triphenylphosphine ($Ph_3P$), 2) a method which comprises reacting with hydrochloric acid or the like.

In the above 1), the reaction can be carried out in an aprotic solvent (e.g., diethylether, tetrahydrofuran, dimethylformamide, benzene, toluene, dichloromethane, chloroform or the like) with stirring for 0.5 to 5 h at 0° C. to room temperature. The amount of diethylazodicarboxylate (DEAD) and triphenylphosphine ($Ph_3P$) are 1.0 to 1.5 mole equivalent to that of the compound (V).

In the above 2), the reaction can be carried out in concentrated hydrochloric acid with refluxing for 0.5 to 10 h.

Process 4

This is a process for producing a compound of the formula (II) which comprises introducing $R^2$ (a group of the formula: $—C(=R^5)—R^6$ or a group of the formula: $—SO_2R^7$ wherein $R^5$ is O or S, $R^6$ is alkyl, alkoxy, alkylthio, optionally substituted amino, optionally substituted aralkyloxy, optionally substituted aralkylthio, optionally substituted aralkylamino, alkoxyalkyl, alkylthioalkyl or optionally substituted aminoalkyl, $R^7$ is alkyl, optionally substituted amino, optionally substituted aryl or optionally substituted heteroaryl, to the compound of the formula (VI).

This process can be carried out by reacting with a compound of the formula: $X—C(=R^5)—R^6$ wherein $R^5$ and $R^6$ are as defined above and X is halogen in the presence of a base (e.g., triethylamine, pyridine, N,N-dimethylaminopyridine or the like). This process can be carried out under generally known conditions of N-acylation. For example, the reaction can be carried out in an aprotic solvent (e.g., diethylether, tetrahydrofuran, dimethylformamide, benzene, toluene, dichloromethane, chloroform or the like) with stirring at 0 to 100° C. for 0.5 to 10 h.

A thioic acid ester, a compound wherein $R^5$ is S, $R^6$ is alkylthio or optionally substituted aralkylthio can be prepared by reacting with carbon dioxide ($CS_2$) in the presence of a base (e.g., sodium hydride or the like), and reacting with halogenated alkyl (e.g., methyl iodide, ethyl iodide or the like) or halogenated aralkyl (e.g., benzylbromide or the like). The reaction can be carried out in an aprotic solvent (e.g., diethylether, tetrahydrofuran, dimethylformamide, benzene, toluene, dichloromethane, chloroform or the like) with stirring at 0° C. to room temperature.

When $R^2$ to be introduced is a group of the formula: $—SO_2R^7$ wherein $R^7$ is alkyl, optionally substituted amino, optionally substituted aryl or optionally substituted heteroaryl, the compound of the formula (VI) can be reacted with a compound of the formula: $R^7SO_2X$ wherein X is halogen or the like in the presence of a base.

A prodrug is a derivative which is converted to a pharmaceutically active compound of the present invention under a physiological condition. Method for the selection and process of an appropriate prodrug derivative are described in the literature such as Design of Prodrugs, Elsevier, Amsterdam 1985.

A prodrug of the present invention can be prepared by introducing a leaving group to substituents on ring A which are substitutable (e.g., amino, hydroxy or the like). Examples of a prodrug derived form a compound having an amino group includes carbamate derivatives (e.g., methylcarbamate, cyclopropylmethylcarbamate, t-butylcarbamate, benzylcarbamate or the like), amide derivatives (e.g., formamide, acetamide or the like), N-alkyl derivative (e.g., N-allylamine, N-methoxymethylamine or the like) or the like. Examples of a prodrug derived form a compound having hydroxy group include ether derivatives (methoxymethylether, methoxyethoxymethylether or the like), ester derivatives (e.g., acetate, pivaloate, benzoate or the like) or the like.

Examples of a pharmaceutically acceptable salt include basic salts (e.g., alkali metal salts such as sodium or potassium salts; alkaline-earth metal salts such as calcium or magnesium salts; ammonium salts; aliphatic amine salts such as trimethylamine, triethylamine, dicyclohexylamine, ethanolamine, diethanolamine, triethanolamine or procaine salts; aralkyl amine salts such as N,N-dibenzylethylenediamine salts; heterocyclic aromatic amine salts such as pyridine salts, picoline salts, quinoline salts or isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts or tetrabutylammonium salts; and basic amino acid salts such as arginine salts or lysine salts). Acid addition salts include, for example, mineral acid salts such as hydrochlorides salts, sulfates salts, nitrate salts, phosphates salts, carbonates salts, hydrogen carbonates salts or perchlorates salts; organic acid salts such as acetates, propionates, lactates, maleates, fumarates, tartrates, malates, succinates, or ascorbates; sulfonates such as methanesulfonates, isethionates, benzenesulfonates, or p-toluenesulfonates; and acidic amino acid salts such as aspartates or glutamates.

A solvate includes a solvate of the compound of the formula (I), a prodrug of itself or a pharmaceutically acceptable salt thereof, for example, monosolvate, disolvate, monohydrate, dihydrate or the like.

The compound of the present invention has a binding activity to the cannabinoid type 2 receptor (CB2R), and binds to the cannabinoid type 2 receptor (CB2R) to exhibit an antagonistic activity or agonistic activity to CB2R, especially an agonistic activity to CB2R.

Therefore, the compound of the present invention can be used for treating or preventing diseases associated with the cannabinoid type 2 receptor (CB2R). For example, Proc. Natl. Acad. Sci. USA 96, 14228–14233, discloses that CB2R agonists have an anti-inflammatory activity and analgesic activity. Nature, 1998, 349, 277–281 discloses that CB2R agonists have an analgesic activity. European Journal of Pharmacology 396 (2000) 85–92 discloses that CB2R antagonists have an analgesic activity. Furthermore, in Cancer Research 61(2001)5784–5789 is described an agonist to the cannabinoid type 2 receptor having a degeneracy effect to brain tumor, and in European Journal of Pharmacology 396 (2000) 85–92 is described an antagonist to the cannabinoid type 2 receptor having an analgesic effect. Furthermore, in J Pharmacol Exp Ther, 2001, 296, 420–425 is described that the compound having a binding activity to the cannabinoid type 2 receptor (an agonistic activity and/or antagonistic activity) exhibits an anti-inflammatory effect. In Pain, 2001, 93, 239–245 is described that the compound having an agonistic activity to the cannabinoid type 2 receptor exhibits analgesic effect.

The compound of the present invention is thought to suppress the activation of immunocyte, inflammatory cells and peripheral neurons to exhibit an activity to the peripheral cell system (e.g., an immunosuppressive activity, an anti-inflammatory activity and an analgesic activity). Thus, the present compounds can be used as anti-inflammatory agents, antiallergenic agents, analgesic agents, immunodeficiency treating agents, immunosuppressive agents, immunomodulating agents, autoimmune disease treating agents, chronic rheumatoid arthritis treating agents, multiple sclerosis treating agents or the like.

Agonists to the cannabinoid type 2 receptor are known to suppress nephritis caused by rat Thy-1 antibody in WO97/29079. Therefore, the present compounds are useful as nephritis treating agents.

When using a compound of the present invention in treatment, it can be formulated into ordinary formulations for oral and parenteral administration. A pharmaceutical composition containing a compound of the present invention can be in the form for oral and parenteral administration. Specifically, it can be formulated into formulations for oral administration such as tablets, capsules, granules, powders, syrup, and the like; those for parenteral administration such as injectable solution or suspension for intravenous, intramuscular or subcutaneous injection, inhalant, eye drops, nasal drops, suppositories, or percutaneous formulations such as ointment.

In preparing the formulations, carriers, excipients, solvents and bases known to one ordinary skilled in the art may be used. Tablets are prepared by compressing or formulating an active ingredient together with auxiliary components. Examples of usable auxiliary components include pharmaceutically acceptable excipients such as binders (e.g., cornstarch), fillers (e.g., lactose, microcrystalline cellulose), disintegrates (e.g., starch sodium glycolate) or lubricants (e.g., magnesium stearate). Tablets may be coated appropriately. In the case of liquid formulations such as syrups, solutions or suspensions, they may contain suspending agents (e.g., methyl cellulose), emulsifiers (e.g., lecithin), preservatives and the like. In the case of injectable formulations, it may be in the form of solution or suspension, or oily or aqueous emulsion, which may contain suspension-stabilizing agent or dispensing agent, and the like. In the case of an inhalant, it is formulated into a liquid formulation applicable to an inhaler. In the case of eye drops, it is formulated into a solution or a suspension.

Although an appropriate dosage of the present compound varies depending on the administration route, age, body weight, sex, or conditions of the patient, and the kind of drug(s) used together, if any, and should be determined by the physician in the end, in the case of oral administration, the daily dosage can generally be between about 0.01–100 mg, preferably about 0.01–10 mg, more preferably about 0.01–1 mg, per kg body weight. In the case of parenteral administration, the daily dosage can generally be between about 0.001–100 mg, preferably about 0.001–1 mg, more preferably about 0.001–0.1 mg, per kg body weight. The daily dosage can be administered in 1–4 divisions.

EXAMPLE

The following Examples are provided to further illustrate the present invention and are not to be construed as limiting the scope.

The meaning of each abbreviation are shown as follows.
Me: methyl, Et: ethyl, Pr: propyl, $Pr^i$: isopropyl,
Bu: butyl, $Bu^i$: isobutyl, $Bu^s$: sec-butyl,
$Bu^t$: t-butyl,
Ph: phenyl,
DMF: N,N-dimethylformamide, THF: tetrahydrofuran,

Reference Example 1-1

Preparation of (2-isopropylphenyl)isothiocyanate (Compound 2)

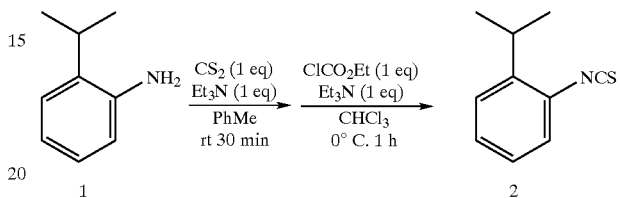

To a mixture of 2-isopropylaniline (5.00 g), triethylamine (3.74 g) and toluene (10 ml) was added dropwise for 10 min carbon dioxide (2.81 g). The reaction mixture was stirred at room temperature for 1 h and kept stationary for 12 h. The reaction mixture was concentrated under reduced pressure. Dichloromethane (20 ml) and triethylamine (3.74 g) were added thereto. To the reaction mixture was added ethyl chlorocarbonate (4.01 g) under ice-cooling for 10 min. The reaction mixture was stirred at room temperature for 1 h. To the reaction mixture was added 10% hydrochloric acid (20 ml). The reaction mixture was extracted with dichloromethane (60 ml), dried over anhydrous magnesium sulfate, and concentrated under reduced pressure to give (2-isopropylphenyl)isothiocyanate (6.55 g, yield: 99%) as a yellow oil.

$^1$H-NMR (δ ppm TMS/CDCl$_3$) 1.25 (6H, d, J=6.7), 3.25 (1H, q, J=6.7), 7.14–7.30 (4H, m).

Reference Example 1-2

Preparation of (2-isopropylphenyl)isothiocyanate (Compound 2)

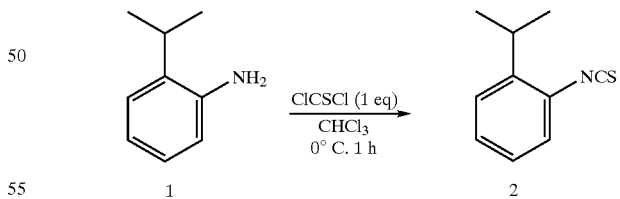

To a solution of 2-isopropylaniline (1.81 g) in diethylether (20 ml) was added dropwise thiophosgene (1.54 g) under ice-cooling for 10 min. The reaction mixture was stirred at room temperature for 1 h.

To the reaction mixture was added water (30 ml). The reaction mixture was extracted with diethylether (60 ml), dried over anhydrous magnesium sulfate, and concentrated under reduced pressure to give (2-isopropylphenyl)isothiocyanate (2.35 g, yield: 99%) as a brown oil.

Reference Example 2

Preparation of N-(2-isopropylphenyl)-N'-(1-hydroxy-2,2-dimethyl)propylthiourea (Compound 3)

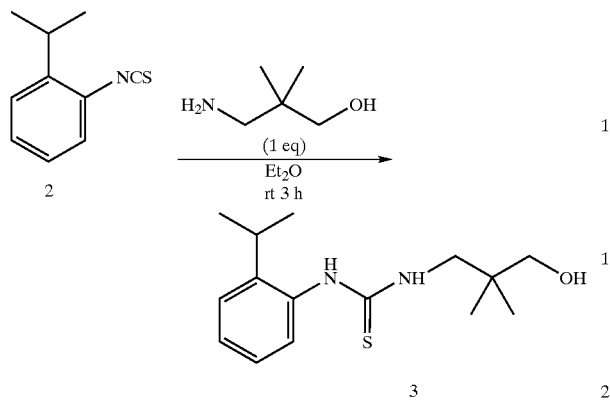

To a solution of (2-isopropylphenyl)isothiocyanate (3.30 g) in diethylether (20 ml) was added 3-amino-2,2-dimethylpropanol (1.92 g). The reaction mixture was stirred at room temperature for 1 h and concentrated under reduced pressure. The obtained residue was purified by silica gel column chromatography (n-hexane/ethyl acetate) to give N-(2-isopropylphenyl)-N'-(1-hydroxy-2,2-dimethyl)propylthiourea (4.60 g, yield: 88%) as a yellow oil.

$^1$H-NMR (δ ppm TMS/CDCl$_3$) 0.82 (6H, s ), 1.25 (6H, d, J=6.7), 3.11 (1H, q, J=6.7), 3.25 (2H, s), 3.55 (2H, d, J=6.3), 6.05 (1H, m ), 7.17–7.40 (4H, m ).

Reference Example 3

Preparation of 2-(2-isopropylphenyl)imino-5,5-dimethyl-1,3-thiazine (Compound 4)

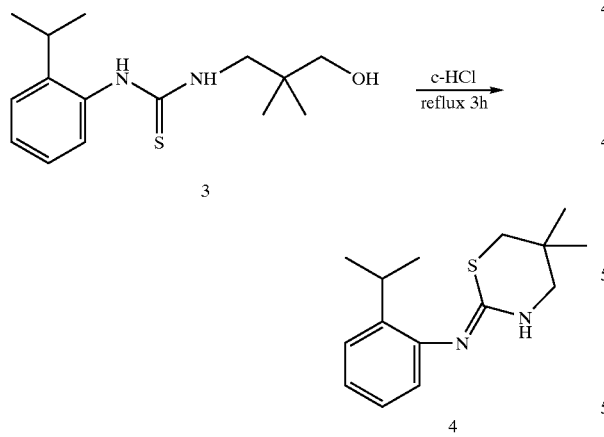

To N-(2-isopropylphenyl)-N'-(1-hydroxy-2,2-dimethyl)propylthiourea (10.37 g) was added conc. hydrochloric acid (5 ml). The reaction mixture was refluxed for 3 h. The reaction mixture was cooled to room temperature and poured into an aqueous solution of 20% sodium hydroxide (25 ml). The precipitated crystal was filtered and recrystallized with ethyl acetate to give 2-(2-isopropylphenyl)imino-5,5-dimethyl-1,3-thiazine (4.80 g, yield: 50%) as a white crystal.

M.p. 155–157° C.

$^1$H-NMR (δ ppm TMS/CDCl$_3$) 1.15 (6H, s), 1.20 (6H, d, J=6.7), 2.67 (2H, s), 3.09 (2H, s), 3.15. (1H, q, J=6.7), 6.88 (1H, m ), 7.05–7.11 (2H, m ), 7.20 (1H, m).

Reference Example 4

Preparation of 2-(2-isopropylphenyl)imino-5,5-dimethyl-1,3-thiazine (Compound 4)

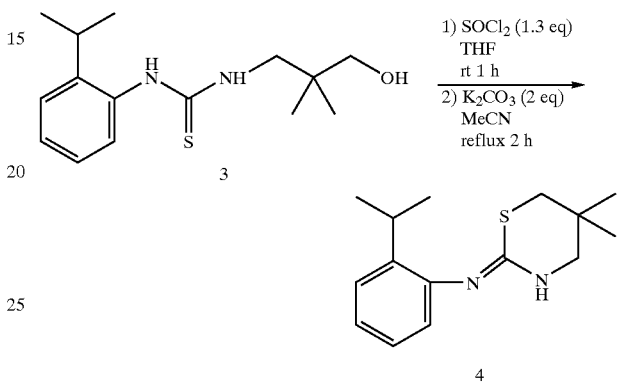

To a solution of N-(2-isopropylphenyl)-N'-(1-hydroxy-2,2-dimethyl)propylthiourea (1.00 g) in tetrahydrofuran (6 ml) was added dropwise thionylchloride (0.60 g). The reaction mixture was stirred at room temperature for 1 h and concentrated under reduced pressure. To the reaction mixture were added acetonitrile (20 ml) and potassium carbonate (0.93 g). The reaction mixture was refluxed for 2 h. To the reaction mixture was added water (40 ml). The reaction mixture was extracted with dichloromethane (60 ml), dried over anhydrous magnesuim sulfate, and concentrated under reduced pressure. The obtained residue was purified by silica gel column chromatography (n-hexane/ethyl acetate) to give 2-(2-isopropylphenyl)imino-5,5-dimethyl-1,3-thiazine (0.45 g, yield: 48%) as a white crystal.

The following Examples were carried out by using 2-(2-isopropylphenyl)imino-5,5-dimethyl-1,3-thiazine prepared in Reference Example 3 and 4.

Example 1

Preparation of 2-(2-isopropylphenyl)imino-3-(allylthio)thiocarbonyl-5,5-dimethyl-1,3-thiazine (Compound I-1)

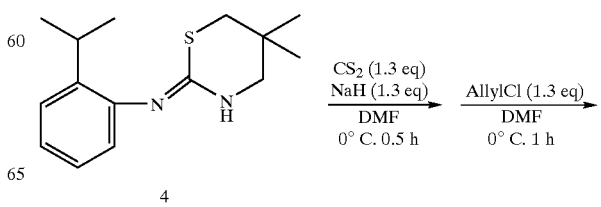

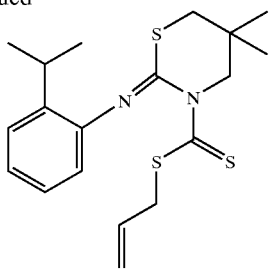

I-1

To a solution of 2-(2-isopropylphenyl)imino-5,5-dimethyl-1,3-thiazine (0.26 g), carbondisulfide (0.10 g) in N,N-dimethylformamide (3 ml) was added 60% sodium hydride (0.05 g) under ice-cooling. The reaction mixture was stirred for 30 minutes. Allylchloride (0.10 g) was added thereto. The reaction mixture was stirred at 0° C. for 1 h. To a reaction mixture was added water (80 ml), extracted with diethylether (100 ml), dried over anhydrous magnesium sulfate, and concentrated under reduced pressure. The obtained residue was purified by silica gel column chromatography (n-hexane/ethyl acetate) to give 2-(2-isopropylphenyl)imino-3-(allylthio)thiocarbonyl-5,5-dimethyl-1,3-thiazine (0.26 g, yield: 69%) as a pale yellow oil.

Example 2

Preparation of 2-(2-isopropylphenyl)imino-3-(5-trifluoromethyl-2-pyridyl)-5,5-dimethyl-1,3-thiazine (Compound I-106)

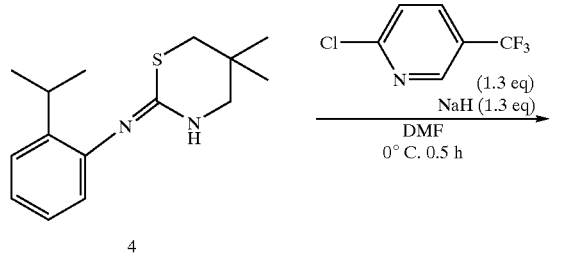

I-106

To a solution of 2-(2-isopropylphenyl)imino-5,5-dimethyl-1,3-thiazine (0.26 g), 5-trifluoromethyl-2-chloropyridine (0.24 g) in N,N-dimethylformamide (3 ml) was added 60% sodium hydride (0.05 g) under ice-cooling. The mixture was stirred at room temperature for 2 h. To a reaction mixture was added water (80 ml), extracted with diethylether (100 ml), dried over anhydrous magnesium sulfate, and concentrated under reduced pressure. The obtained residue was purified by silica gel column chromatography (n-hexane/ethyl acetate) to give 2-(2-isopropylphenyl)imino-3-(5-trifluoromethyl-2-pyridyl)-5,5-dimethyl-1,3-thiazine (0.13 g, yield: 32%) as colorless oil.

The compounds shown in the following tables were prepared in accordance with the above Example. The numbers of left column in Tables represent Compound No. and the compounds obtained in the above Examples are described together.

TABLE 1

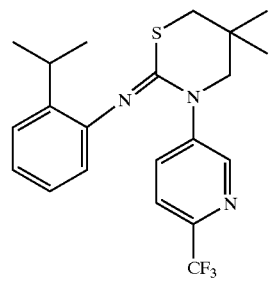

| No | $R^1$ | $R^2$ | $R^3$ | $R^4$ | $R^5$ | $R^6$ | $R^7$ | $R^8$ |
|---|---|---|---|---|---|---|---|---|
| I-1 | $Pr^i$ | H | H | H | H | Allyl | Me | Me |
| I-2 | $Pr^i$ | H | H | H | H | Propargyl | Me | Me |
| I-3 | $Pr^i$ | H | H | H | H | $CH_2CN$ | Me | Me |
| I-4 | $Pr^i$ | H | H | H | H | $CH_2OMe$ | Me | Me |
| I-5 | $Pr^i$ | H | H | H | H | $CH_2CH=CHMe$ | Me | Me |
| I-6 | $Pr^i$ | H | H | H | H | $CH_2CH=CMe_2$ | Me | Me |
| I-7 | $Pr^i$ | H | H | H | H | $CH_2CH_2CH=CH_2$ | Me | Me |
| I-8 | $Pr^i$ | H | H | H | H | $CH_2COMe$ | Me | Me |
| I-9 | $Pr^i$ | H | H | H | H | $CH_2CO_2H$ | Me | Me |
| I-10 | $Pr^i$ | H | H | H | H | $CH_2CO_2Me$ | Me | Me |
| I-11 | $Pr^i$ | H | H | H | H | $CH_2CO_2Et$ | Me | Me |
| I-12 | $Pr^i$ | H | H | H | H | $CH_2CO_2Pr$ | Me | Me |
| I-13 | $Pr^i$ | H | H | H | H | $CH_2CO_2Pr^i$ | Me | Me |
| I-14 | $Pr^i$ | H | H | H | H | $CH_2CO_2Bu^t$ | Me | Me |
| I-15 | $Pr^i$ | H | H | H | H | $CH_2CO_2CH=CH_2$ | Me | Me |
| I-16 | $Pr^i$ | H | H | H | H | $CH_2CO_2CH_2CH=CH_2$ | Me | Me |
| I-17 | $Pr^i$ | H | H | H | H | $CH_2CO_2(CH_2)_2OMe$ | Me | Me |
| I-18 | $Pr^i$ | H | H | H | H | $CH(Me)CO_2Me$ | Me | Me |
| I-19 | $Pr^i$ | H | H | H | H | $C(Me)_2CO_2Et$ | Me | Me |
| I-20 | $Pr^i$ | H | H | H | H | $CH_2CONH_2$ | Me | Me |
| I-21 | $Pr^i$ | H | H | H | H | $CH_2CONMe_2$ | Me | Me |
| I-22 | $Pr^i$ | H | H | H | H | $CH_2CON(Me)OMe$ | Me | Me |
| I-23 | $Pr^i$ | H | H | H | H | $CH_2CF_3$ | Me | Me |
| I-24 | $Pr^i$ | H | H | H | H | $CH_2CH_2OCOMe$ | Me | Me |
| I-25 | $Pr^i$ | H | H | H | H | $CH_2CH_2OPh$ | Me | Me |

TABLE 2

| No | $R^1$ | $R^2$ | $R^3$ | $R^4$ | $R^5$ | $R^6$ | $R^7$ | $R^8$ |
|---|---|---|---|---|---|---|---|---|
| I-26 | $Pr^i$ | H | H | H | H | $CH_2CH_2OCH=CH_2$ | Me | Me |
| I-27 | $Pr^i$ | H | H | H | H | —CH$_2$—(1,3-dioxolan-2-yl) | Me | Me |

TABLE 2-continued

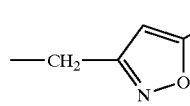

| No | R¹ | R² | R³ | R⁴ | R⁵ | R⁶ | R⁷ | R⁸ |
|---|---|---|---|---|---|---|---|---|
| I-28 | $Pr^i$ | H | H | H | H | -CH₂-(5-Me-isoxazol-3-yl) | Me | Me |
| I-29 | $Pr^i$ | H | H | H | H | -CH₂-(5-$Bu^i$-isoxazol-3-yl) | Me | Me |
| I-30 | $Pr^i$ | H | H | H | H | -CH₂-(5-$Bu^t$-isoxazol-3-yl) | Me | Me |
| I-31 | $Pr^i$ | H | H | H | H | -CH₂-(5-Ph-isoxazol-3-yl) | Me | Me |
| I-32 | $Pr^i$ | H | H | H | H | -CH₂-(3-Me-isoxazol-5-yl) | Me | Me |
| I-33 | $Pr^i$ | H | H | H | H | -CH₂-(3-$Pr^i$-isoxazol-5-yl) | Me | Me |
| I-34 | $Pr^i$ | H | H | H | H | -CH₂-(3-$Bu^i$-isoxazol-5-yl) | Me | Me |

TABLE 2-continued

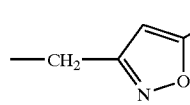

| No | R¹ | R² | R³ | R⁴ | R⁵ | R⁶ | R⁷ | R⁸ |
|---|---|---|---|---|---|---|---|---|
| I-35 | $Pr^i$ | H | H | H | H | -CH₂-(3-$Bu^t$-isoxazol-5-yl) | Me | Me |
| I-36 | $Pr^i$ | H | H | H | H | -CH₂-(4-$Bu^t$-oxazol-2-yl) | Me | Me |
| I-37 | $Pr^i$ | H | H | H | H | -CH₂CH₂-morpholino | Me | Me |
| I-38 | $Pr^i$ | H | H | H | H | -CH₂-(5,5-Me₂-4,5-dihydroisoxazol-3-yl) | Me | Me |
| I-39 | $Pr^i$ | H | H | H | H | Allyl | Et | Et |
| I-40 | $Pr^i$ | H | H | H | H | $CH_2CO_2Et$ | Et | Et |
| I-41 | $Pr^i$ | H | H | H | H | $CH_2CO_2Pr^i$ | Et | Et |
| I-42 | $Pr^i$ | H | H | H | H | $CH_2CO_2Bu^t$ | Et | Et |
| I-43 | $Pr^i$ | H | H | H | H | $CH_2CH_2CO_2Et$ | Et | Et |

TABLE 3

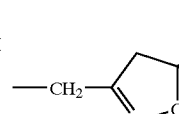

| No | R¹ | R² | R³ | R⁴ | R⁵ | R⁶ | R⁷ | R⁸ |
|---|---|---|---|---|---|---|---|---|
| I-44 | $Pr^i$ | H | H | H | H | $CH_2CH$=CHMe | Et | Et |
| I-45 | $Pr^i$ | H | H | H | H | $CH_2CH$=$CMe_2$ | Et | Et |
| I-46 | $Pr^i$ | H | H | H | H | $CH_2CH_2CH$=$CH_2$ | Et | Et |
| I-47 | $Bu^s$ | H | H | H | H | $CH_2CO_2Et$ | Me | Me |
| I-48 | $Bu^s$ | H | H | H | H | $CH_2CO_2Bu^t$ | Me | Me |
| I-49 | $Bu^s$ | H | H | H | H | Allyl | Et | Et |
| I-50 | $Bu^s$ | H | H | H | H | $CH_2CH_2OCOMe$ | Et | Et |

TABLE 3-continued

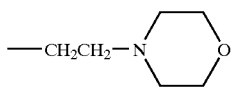

| No | R¹ | R² | R³ | R⁴ | R⁵ | R⁶ | R⁷ | R⁸ |
|---|---|---|---|---|---|---|---|---|
| I-51 | Bu$^s$ | H | H | H | H | —CH$_2$CH$_2$—N(morpholine) | Et | Et |
| I-52 | H | H | Et | H | H | CH$_2$CO$_2$Et | Me | Me |
| I-53 | H | Pr$^i$ | H | H | H | CH$_2$CO$_2$Et | Me | Me |
| I-54 | NMe$_2$ | H | H | H | H | CH$_2$CO$_2$Et | Me | Me |
| I-55 | H | NMe$_2$ | H | H | H | CH$_2$CO$_2$Et | Me | Me |
| I-56 | H | NEt$_2$ | H | H | H | CH$_2$CO$_2$Et | Me | Me |
| I-57 | H | H | Et | H | H | CH$_2$CO$_2$Bu$^t$ | Me | Me |
| I-58 | H | Pr$^i$ | H | H | H | CH$_2$CO$_2$Bu$^t$ | Me | Me |
| I-59 | NMe$_2$ | H | H | H | H | CH$_2$CO$_2$Bu$^t$ | Me | Me |
| I-60 | H | NMe$_2$ | H | H | H | CH$_2$CO$_2$Bu$^t$ | Me | Me |
| I-61 | H | NEt$_2$ | H | H | H | CH$_2$CO$_2$Bu$^t$ | Me | Me |
| I-62 | H | NEt$_2$ | H | H | H | Allyl | Me | Me |
| I-63 | Me | NEt$_2$ | H | H | H | Allyl | Me | Me |
| I-64 | Me | NMe$_2$ | H | H | H | Allyl | Me | Me |
| I-65 | NMe$_2$ | H | H | H | H | Allyl | Et | Et |
| I-66 | NMe$_2$ | H | H | H | H | CH$_2$CO$_2$Bu$^t$ | Et | Et |
| I-67 | OMe | H | H | H | H | Allyl | Et | Et |
| I-68 | OMe | H | H | H | H | CH$_2$CO$_2$Bu$^t$ | Et | Et |
| I-69 | H | H | Et | H | H | Allyl | Et | Et |
| I-70 | H | H | Et | H | H | CH$_2$CO$_2$Bu$^t$ | Et | Et |

TABLE 4

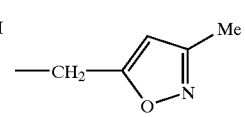

| No | R¹ | R² | R³ | R⁴ | R⁵ | R⁶ | R⁷ | R⁸ |
|---|---|---|---|---|---|---|---|---|
| I-71 | H | H | OCF$_3$ | H | H | Allyl | Et | Et |
| I-72 | H | H | OCF$_3$ | H | H | CH$_2$CO$_2$Bu$^t$ | Et | Et |
| I-73 | NMe$_2$ | H | H | H | H | CH$_2$OMe | Et | Et |
| I-74 | Pr$^i$ | H | H | H | H | Allyl | —(CH$_2$)$_4$— | |
| I-75 | NMe$_2$ | H | H | H | H | Allyl | —(CH$_2$)$_4$— | |
| I-76 | NMe$_2$ | H | H | H | H | CH$_2$CO$_2$Bu$^t$ | —(CH$_2$)$_4$— | |
| I-77 | Pr$^i$ | H | H | H | H | CH$_2$CO$_2$(CH$_2$)$_2$OMe | —(CH$_2$)$_4$— | |
| I-78 | Pr$^i$ | H | H | H | H | —CH$_2$-(3-methylisoxazol-5-yl) | —(CH$_2$)$_4$— | |
| I-79 | OMe | H | H | H | H | Allyl | —(CH$_2$)$_4$— | |
| I-80 | OMe | H | H | H | H | CH$_2$CO$_2$Bu$^t$ | —(CH$_2$)$_4$— | |
| I-81 | NMe$_2$ | H | H | H | H | CH$_2$OMe | —(CH$_2$)$_4$— | |
| I-82 | H | H | Et | H | H | Allyl | —(CH$_2$)$_4$— | |
| I-83 | H | H | OCF$_3$ | H | H | Allyl | —(CH$_2$)$_4$— | |
| I-84 | NMe$_2$ | H | H | H | H | Allyl | —(CH$_2$)$_5$— | |
| I-85 | NMe$_2$ | H | H | H | H | CH$_2$CO$_2$Bu$^t$ | —(CH$_2$)$_5$— | |
| I-86 | OMe | H | H | H | H | Allyl | —(CH$_2$)$_5$— | |

TABLE 4-continued

| No | R¹ | R² | R³ | R⁴ | R⁵ | R⁶ | R⁷ | R⁸ |
|---|---|---|---|---|---|---|---|---|
| I-87 | OMe | H | H | H | H | $CH_2CO_2Bu^t$ | $-(CH_2)_5-$ | |
| I-88 | H | H | Et | H | H | Allyl | $-(CH_2)_5-$ | |
| I-89 | $Pr^i$ | H | H | H | H | $-CH_2CH_2O-$(tetrahydropyran-2-yl) | $-(CH_2)_5-$ | |
| I-90 | $Pr^i$ | H | H | H | H | $CH_2CH_2OH$ | $-(CH_2)_5-$ | |
| I-91 | H | H | $OCF_3$ | H | H | Allyl | $-(CH_2)_5-$ | |
| I-92 | $Pr^i$ | H | H | H | H | Allyl | $-(CH_2)_2O(CH_2)_2-$ | |
| I-93 | $Pr^i$ | H | H | H | H | Me | $-(CH_2)_2O(CH_2)_2-$ | |
| I-94 | $Pr^i$ | H | H | H | H | $CH_2CO_2H$ | Et | Et |

TABLE 5

| No | A | R⁶ | R⁷ | R⁸ |
|---|---|---|---|---|
| I-95 | 1-methylnaphthyl | Allyl | Me | Me |
| I-96 | 1-methylnaphthyl | $CH_2CO_2Bu^t$ | Me | Me |
| I-97 | 1-methylnaphthyl | $CH_2CO_2(CH_2)_2OMe$ | Me | Me |
| I-98 | 1-methylnaphthyl | Allyl | Et | Et |
| I-99 | 1-methylnaphthyl | $CH_2CO_2Bu^t$ | Et | Et |
| I-100 | 5-methylquinolinyl | Allyl | Et | Et |
| I-101 | 1-methylnaphthyl | Allyl | $-(CH_2)_4-$ | |

TABLE 5-continued

[Structure: ring A-N=C(S-CH2-CR7R8-CH2-N(CSSR6))]

| | A | R⁶ | R⁷ R⁸ |
|---|---|---|---|
| I-102 | 1-naphthyl | CH₂CO₂Buᵗ | —(CH₂)₄— |
| I-103 | 5-quinolyl | Allyl | —(CH₂)₄— |
| I-104 | 1-naphthyl | Allyl | —(CH₂)₅— |
| I-105 | 5-quinolyl | Allyl | —(CH₂)₅— |

TABLE 6

[Structure: phenyl(R1-R5)-N=C(S-CH2-CR7R8-CH2-N(R6))]

| | R¹ | R² | R³ | R⁴ | R⁵ | R⁶ | R⁷ | R⁸ |
|---|---|---|---|---|---|---|---|---|
| I-106 | Prⁱ | H | H | H | H | 6-methyl-3-(trifluoromethyl)pyridin-2-yl | Me | Me |
| I-107 | Prⁱ | H | H | H | H | benzothiazol-2-yl | Me | Me |
| I-108 | Prⁱ | H | H | H | H | benzoxazol-2-yl | Me | Me |
| I-109 | Prⁱ | H | H | H | H | 6-methyl-3-nitropyridin-2-yl | Me | Me |
| I-110 | H | H | Pr | H | H | 6-methyl-3-(trifluoromethyl)pyridin-2-yl | Me | Me |

TABLE 6-continued

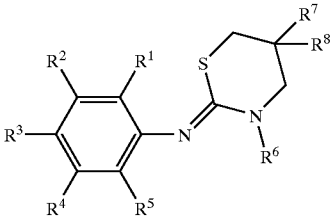

| | R¹ | R² | R³ | R⁴ | R⁵ | R⁶ | R⁷ | R⁸ |
|---|---|---|---|---|---|---|---|---|
| I-111 | Pr$^i$ | H | H | H | H | 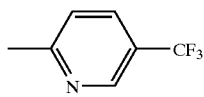 | Et | Et |
| I-112 | Pr$^i$ | H | H | H | H | 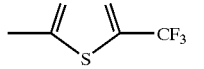 | Me | Me |
| I-113 | Pr$^i$ | H | H | H | H | CSSMe | —(CH$_2$)$_2$N(CH$_2$Ph)(CH$_2$)$_2$— | |

TABLE 7

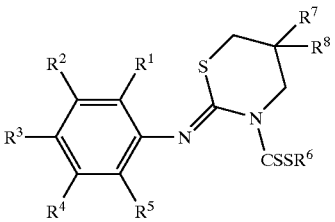

| | R¹ | R² | R³ | R⁴ | R⁵ | R⁶ | R⁷ | R⁸ |
|---|---|---|---|---|---|---|---|---|
| I-114 | H | SMe | H | H | H | Allyl | Et | Et |
| I-115 | H | SMe | H | H | H | Allyl | —(CH$_2$)$_4$— | |
| I-116 | H | SMe | H | H | H | Allyl | —(CH$_2$)$_5$— | |
| I-117 | H | H | SMe | H | H | Allyl | —(CH$_2$)$_4$— | |
| I-118 | H | H | SMe | H | H | Allyl | —(CH$_2$)$_5$— | |
| I-119 | OMe | H | Et | H | H | Allyl | Me | Me |
| I-120 | OMe | H | Pr$^i$ | H | H | Allyl | Me | Me |
| I-121 | Pr$^i$ | H | OMe | H | H | Allyl | Me | Me |
| I-122 | Pr$^i$ | H | OEt | H | H | Allyl | Me | Me |
| I-123 | H | OEt | OEt | H | H | Allyl | Me | Me |
| I-124 | H | OPr | OPr | H | H | Allyl | Me | Me |
| I-125 | H | OMs | OEt | H | H | Allyl | Me | Me |
| I-126 | H | H | (CH$_2$)$_2$OEt | H | H | Allyl | Me | Me |
| I-127 | H | OMe | OEt | H | H | Allyl | Et | Et |
| I-128 | H | OEt | OEt | H | H | Allyl | Et | Et |
| I-129 | H | OEt | OPr | H | H | Allyl | Et | Et |
| I-130 | H | OMs | OPr | H | H | Allyl | Et | Et |
| I-131 | H | OPr | OPr | H | H | Allyl | Et | Et |
| I-132 | H | OPr$^i$ | OPr | H | H | Allyl | Et | Et |
| I-133 | H | H | (CH$_2$)$_2$NMe$_2$ | H | H | Allyl | Me | Me |
| I-134 | Pr$^i$ | H | H | H | H | CH$_2$CO$_2$Bu$^t$ | —(CH$_2$)$_5$— | |
| I-135 | Pr$^i$ | H | H | H | H | Me | —(CH$_2$)$_2$N(Me)(CH$_2$)$_2$— | |
| I-136 | Pr$^i$ | H | H | H | H | Me | —(CH$_2$)$_2$N(Et)(CH$_2$)$_2$— | |
| I-137 | F | H | F | H | H | Allyl | Me | Me |
| I-138 | H | Cl | Cl | H | H | Allyl | Me | Me |
| I-139 | Me | H | Cl | H | H | Allyl | Me | Me |
| I-140 | Cl | H | Me | H | H | Allyl | Me | Me |
| I-141 | H | H | (CH$_2$)$_2$OMe | H | H | Allyl | Me | Me |
| I-142 | H | H | Pr$^i$ | H | H | Allyl | —(CH$_2$)$_4$— | |
| I-143 | H | H | Pr$^i$ | H | H | CH$_2$CO$_2$Bu$^t$ | —(CH$_2$)$_4$— | |

TABLE 8

| | R¹ | R² | R³ | R⁴ | R⁵ | R⁶ | R⁷ | R⁸ |
|---|---|---|---|---|---|---|---|---|
| I-144 | H | H | $Pr^i$ | H | H | Allyl | Et | Et |
| I-145 | H | H | $Pr^i$ | H | H | $CH_2CO_2Bu^t$ | Et | Et |
| I-146 | H | H | $Pr^i$ | H | H | Allyl | —(CH₂)₅— | |
| I-147 | OMe | H | H | H | H | $CH_2CO_2Bu^t$ | Pr | Pr |
| I-148 | OMe | H | H | H | H | $CH_2CO_2Bu^t$ | $Pr^i$ | $Pr^i$ |
| I-149 | OMe | H | H | H | H | Allyl | Pr | Pr |
| I-150 | $Bu^s$ | H | H | H | H | Me | —(CH₂)₂N(Me)(CH₂)₂— | |

TABLE 9

| | A | R⁶ | R⁷ | R⁸ |
|---|---|---|---|---|
| I-151 | 1-naphthyl (substituted at position adjacent) | $CSSCH_2CO_2Bu^t$ | —(CH₂)₅— | |
| I-152 | 1-naphthyl | $CSSCH_2CO_2Bu^t$ | Et | Et |
| I-153 | 2-$Pr^i$-phenyl | COSMe | —(CH₂)₂N(Me)(CH₂)₂— | |
| I-154 | 2-$Bu^s$-phenyl | COSMe | —(CH₂)₂N(Me)(CH₂)₂— | |

Physical data of the compounds described in above Table are shown the following Tables.

TABLE 10

| Compound No | m.p. | NMR(CHCl₃) |
|---|---|---|
| I-1 | | 1.20(6H, d, J=6.9), 1.23(6H, s), 2.66(2H, s), 3.09(1H, sept, J=6.9), 3.93–3.97(2H, m), 4.49(2H, s), 5.15–5.19(1H, m), 5.28–5.39 (1H, m), 5.86–6.01(1H, m), 6.89–6.94(1H, m), 7.11–7.21 (2H, m), 7.29–7.34(1H, m) |
| I-2 | 93.5–94.5 | 1.21(6H, d, J=6.9), 1.23(6H, s), 2.20(1H, t, J=2.6), 2.69(2H, s), 3.09(1H, sept, J=6.9), 3.99(2H, d, J=2.6), 4.49(2H, s), 6.90–6.94 (1H, m), 7.14–7.22(2H, m), 7.32–7.35(1H, m) |
| I-3 | | 1.21(6H, d, J=6.9), 1.25(6H, s), 2.74(2H, s), 3.02(1H, sept, J=6.9), 4.00(2H, s), 4.50(2H, s), 6.87–6.90(1H, m), 7.15–7.22 (2H, m), 7.32–7.36(1H, m) |
| I-4 | 73–74 | 1.21(6H, d, J=6.9), 1.24(6H, s), 2.67(2H, s), 3.10(1H, sept, J=6.9), 3.44(3H, s), 4.48(2H, s), 5.45(2H, s), 6.92–6.96(1H, m), 7.16–7.20(2H, m), 7.32–7.35(1H, m) |
| I-5 | | 1.19(6H, d, J=6.9), 1.22(6H, s), 1.71(3H, d, J=6.6), 2.64(2H, s), 3.15(1H, sept, J=6.9), 3.88(2H, d, J=6.9), 4.49(2H, s), 5.56–5.62 (1H, m), 5.69–5.78(1H, m), 6.89–6.94(1H, m), 7.11–7.21(2H, m), 7.29–7.34(1H, m) |
| I-6 | | 1.19(6H, d, J=6.9), 1.23(6H, s), 1.72(3H, d, J=6.9), 2.65(2H, s), 3.15(1H, sept, J=6.9), 3.89(2H, d, J=6.9), 4.49(2H, s), 5.28–5.35 (1H, m), 6.87–6.92(1H, m), 7.11–7.21(2H, m), 7.29–7.34(1H, m) |
| I-7 | | 1.19(6H, d, J=6.9), 1.23(6H, s), 2.47(2H, q, J=7.4), 2.64(2H, s), 3.15(1H, sept, J=6.9), 3.34(2H, t, J=7.4), 4.48(2H, s), 5.01–5.14 (2H, m), 5.74–5.98(1H, m), 6.82–6.89(1H, m), 7.11–7.21(2H, m), 7.29–7.34(1H, m) |
| I-8 | 92–96 | 1.20(6H, d, J=6.9), 1.22(6H, s), 2.35(3H, s), 2.70(2H, s), 3.08 (1H, sept, J=6.9), 4.12(2H, s), 4.46(2H, s), 6.92–6.97(1H, m), 7.11–7.22(2H, m), 7.30–7.35(1H, m) |

TABLE 10-continued

| Compound No | m.p. | Physical properties NMR(CHCl$_3$) |
|---|---|---|
| I-9 | | 1.20(6H, d, J=6.9), 1.24(6H, s), 2.74(2H, s), 3.05(1H, sept, J=6.9), 4.17(2H, s), 4.39(2H, s), 6.93–6.97(1H, m), 7.18–7.24 (2H, m), 7.33–7.38(1H, m) |
| I-10 | 82–83 | 1.20(6H, d, J=6.9), 1.22(6H, s), 2.70(2H, s), 3.09(1H, sept, J=6.9), 3.75(3H, s), 4.07(2H, s), 4.48(2H, s), 6.92–6.95(1H, m), 7.13–7.21(2H, m), 7.31–7.35(1H, m) |

TABLE 11

| Compound No | m.p. | Physical properties NMR(CHCl$_3$) |
|---|---|---|
| I-11 | 95.5–96.5 | 1.20(6H, d, J=6.9), 1.22(6H, s), 1.29(3H, t, J=7.3), 2.70(2H, s), 3.09(1H, sept, J=6.9), 4.06(2H, s), 4.21(2H, q, J=7.3), 4.48(2H, s), 6.92–6.96(1H, m), 7.15–7.19(2H, m), 7.31–7.34(1H, m) |
| I-12 | 83–86 | 0.96(3H, t, J=7.3), 1.20(6H, d, J=6.9), 1.22(6H, s), 1.68(2H, sext, J=7.3), 2.70(2H, s), 3.09(1H, sept, J=6.9), 4.07(2H, s), 4.11(2H, t, J=7.3), 4.48(2H, s), 6.92–6.95(1H, m), 7.13–7.20 (2H, m), 7.31–7.34(1H, m) |
| I-13 | 95–96 | 1.20(6H, d, J=6.9), 1.22(6H, s), 1.27(6H, d, J=6.3), 2.70(2H, s), 3.09(1H, sept, J=6.9), 4.02(2H, s), 4.47(2H, s), 5.06(1H, sept, J=6.3), 6.92–6.97(1H, m), 7.13–7.21(2H, m), 7.29–7.34(1H, m) |
| I-14 | | 1.20(6H, d, J=6.9), 1.22(6H, s), 1.47(9H, s), 2.69(2H, s), 3.09 (1H, sept, J=6.9), 3.97(2H, s), 4.47(2H, s), 6.92–6.96(1H, m), 7.11–7.20(2H, m), 7.31–7.34(1H, m) |
| I-15 | | 1.21(6H, d, J=6.9), 1.22(6H, s), 2.70(2H, s), 3.08(1H, sept, J=6.9), 4.13(2H, s), 4.48(2H, s), 4.62(1H, dd, J=6.3, 1.7), 4.95 (1H, dd, J=13.9, 1.7), 6.92–6.95(1H, m), 7.13–7.35(4H, m) |
| I-16 | | 1.20(6H, d, J=6.9), 1.22(6H, s), 2.69(2H, s), 3.08(1H, sept, J=6.9), 4.10(2H, s), 4.47(2H, s), 4.63–4.66(2H, m), 5.23–5.39 (2H, m), 5.86–5.98(1H, m), 6.92–6.95(1H, m), 7.15–7.21(2H, m), 7.31–7.34(1H, m) |
| I-17 | | 1.20(6H, d, J=6.9), 1.22(6H, s), 2.70(2H, s), 3.08(1H, sept, J=6.9), 3.40(3H, s), 3.61–3.65(2H, m), 4.11(2H, d, J=2.3), 4.29–4.37 (2H, m), 4.47(2H, s), 6.92–6.95(1H, m), 7.13–7.20(2H, m), 7.31–7.34(1H, m) |
| I-18 | | 1.19–1.23(12H, m), 1.58(3H, d, J=7.3), 2.62(1H, d, J=13.2), 2.74(1H, d, J=13.2), 3.11(1H, sept, J=6.9), 3.74(3H, s), 4.18 (1H, d, J=13.5), 4.66(1H, q, J=7.3), 4.72(1H, d, J=13.5), 6.91–6.94 (1H, m), 7.13–7.21(2H, m), 7.31–7.35(1H, m) |
| I-19 | | 1.21(6H, d, J=6.9), 1.21(6H, s), 1.28(3H, t, J=7.3), 1.71(6H, s), 2.66(2H, s), 3.14(1H, sept, J=6.9), 4.18(2H, q, J=7.3), 4.40(2H, s), 6.88–6.92(1H, m), 7.13–7.21(2H, m), 7.31–7.35(1H, m) |
| I-20 | 117–119 | 1.21(6H, d, J=6.9), 1.24(6H, s), 2.69(2H, s), 3.05(1H, sept, J=6.9), 4.03(2H, s), 4.48(2H, s), 5.35(1H, brs), 6.50(1H, brs), 6.89–6.92(1H, m), 7.14–7.22(2H, m), 7.32–7.35(1H, m) |

TABLE 12

| Compound No | m.p. | Physical properties NMR(CHCl$_3$) |
|---|---|---|
| I-21 | | 1.20(6H, d, J=6.9), 1.22(6H, s), 2.69(2H, s), 2.97(3H, s), 3.10 (1H, sept, J=6.9), 3.15(3H, s), 4.20(2H, s), 4.47(2H, s), 6.94–6.97 (1H, m), 7.12–7.20(2H, m), 7.30–7.33(1H, m) |
| I-22 | | 1.20(6H, d, J=6.9), 1.22(6H, s), 2.71(2H, s), 3.10(1H, sept, J=6.9), 3.23(3H, s), 3.82(3H, s), 4.33(2H, s), 4.47(2H, s), 6.95–7.00 (1H, m), 7.12–7.21(2H, m), 7.30–7.34(1H, m) |
| I-23 | | 1.20(6H, d, J=6.9), 1.23(6H, s), 2.68(2H, s), 3.09(1H, sept, J=6.9), 4.22(2H, q, J=9.9), 4.50(2H, s), 6.89–6.95(1H, m), 7.14–7.23 (2H, m), 7.31–7.36(1H, m) |
| I-24 | | 1.18(6H, d, J=6.9), 1.23(6H, s), 2.07(3H, s), 2.67(2H, s), 3.09 (1H, sept, J=6.9), 3.57(2H, t, J=6.6), 4.35(2H, t, J=6.6), 4.49 (2H, s), 6.88–6.92(1H, m), 7.13–7.22(2H, m), 7.30–7.35(1H, m) |

TABLE 12-continued

| Compound No | m.p. | NMR(CHCl₃) |
|---|---|---|
| I-25 | | 1.20(6H, d, J=6.9), 1.23(6H, s), 2.65(2H, s), 3.10(1H, sept, J=6.9), 3.71(2H, t, J=6.6), 4.29(2H, t, J=6.6), 4.49(2H, s), 6.89–6.97(4H, m), 7.15–7.21(2H, m), 7.25–7.34(3H, m) |
| I-26 | | 1.21(6H, d, J=6.9), 1.23(6h, s), 2.66(2H, s), 3.10(1H, sept, J=6.9), 3.60(2H, t, J=6.6), 3.99–4.05(3H, m), 4.24(1H, dd, 14.2, 1.9), 4.49(2H, s), 6.47(1H, dd, 14.2, 6.9), 6.89–6.94(1H, m), 7.15–7.21(2H, m), 7.31–7.34(1H, m) |
| I-27 | | 1.20(6H, d, J=6.9), 1.23(6H, s), 3.09(1H, sept, J=6.9), 3.64(2H, s, J=4.6), 3.84–4.03(4H, m), 4.49(2H, s), 5.21(1H, t, J=4.6), 6.91–6.96(1H, m), 7.12–7.21(2H, m), 7.30–7.34(1H, m) |
| I-28 | 124–126 | 1.17(6H, d, J=6.9), 1.23(6H, s), 2.38(3H, s), 2.67(2H, s), 3.06 (1H, sept, J=6.9), 4.50(2H, s), 4.55(2H, s), 6.05(1H, s), 6.86–6.90 (1H, m), 7.12–7.19(2H, m), 7.30–7.33(1H, m) |
| I-29 | | 0.94(6H, d, J=6.6), 1.17(6H, d, J=6.9), 1.23(6H, s), 1.93–2.08 (1H, m), 2.58(2H, d, J=6.6), 2.66(2H, s), 3.07(1H, sept, J=6.9), 4.50(2H, s), 4.55(2H, s), 6.05(1H, s), 6.85–6.91(1H, m), 7.12–7.19 (2H, m), 7.28–7.33(1H, m) |
| I-30 | 129–130 | 1.17(6H, d, J=6.9), 1.23(6H, s), 1.31(9H, s), 2.67(2H, s), 3.08 (1H, sept, J=6.9), 4.51(2H, s), 4.59(2H, s), 6.00(1H, s), 6.87–6.91 (1H, m), 7.14–7.19(2H, m), 7.30–7.33(1H, m) |

TABLE 13

| Compound No | m.p. | NMR(CHCl₃) |
|---|---|---|
| I-31 | | 1.18(6H, d, J=6.9), 1.24(6H, s), 2.68(2H, s), 3.07(1H, sept, J=6.9), 4.52(2H, s), 4.64(2H, s), 6.61(1H, s), 6.88–6.91(1H, m), 7.12–7.19(2H, m), 7.29–7.33(1H, m), 7.41–7.48(3H, m), 7.71–7.76 (2H, m) |
| I-32 | | 1.18(6H, d, J=6.9), 1.22(6H, s), 2.26(3H, s), 2.66(2H, s), 3.06 (1H, sept, J=6.9), 4.48(2H, s), 4.58(2H, s), 6.09(1H, s), 6.87–6.92 (1H, m), 7.13–7.20(2H, m), 7.28–7.34(1H, m) |
| I-33 | | 1.18(6H, d, J=6.9), 1.21(6H, s), 1.25(6H, d, J=6.9), 2.66(2H, s), 3.02(1H, sept, J=6.9), 3.04(1H, sept, J=6.9), 4.49(2H, s), 4.59 (2H, s), 6.12(1H, s), 6.88–6.92(1H, m), 7.13–7.21(2H, m), 7.29–7.34 (1H, m) |
| I-34 | | 0.94(6H, d, J=6.6), 1.18(6H, d, J=6.9), 1.21(6H, s), 1.88–2.05 (1H, m), 2.49(2H, d, J=6.6), 2.65(2H, s), 3.07(1H, sept, J=6.9), 4.49(2H, s), 4.59(2H, s), 6.09(1H, s), 6.87–6.91(1H, m), 7.13–7.20 (2H, m), 7.29–7.34(1H, m) |
| I-35 | 124–125 | 1.18(6H, d, J=6.9), 1.21(6H, s), 1.30(9H, s), 2.65(2H, s), 3.07 (1H, sept, J=6.9), 4.49(2H, s), 4.59(2H, s), 6.15(1H, s), 6.88–6.93 (1H, m), 7.13–7.21(2H, m), 7.29–7.34(1H, m) |
| I-36 | | 1.17(6H, d, J=6.9), 1.22(6H, s), 1.26(9H, s), 2.67(2H, s), 3.07 (1H, sept, J=6.9), 4.49(2H, s), 4.59(2H, s), 6.61(1H, s), 6.88–6.92 (1H, m), 7.11–7.18(2H, m), 7.29–7.32(1H, m) |
| I-37 | | 1.21(6H, d, J=6.9), 1.23(6H, s), 2.52–2.56(4H, m), 2.65(2H, s), 2.68–2.73(2H, m), 3.11(1H, sept, J=6.9), 3.41–3.52(2H, m), 3.70–3.73(4H, m), 4.48(2H, s), 6.87–6.92(1H, m), 7.15–7.19(2H, m), 7.31–7.35(1H, m) |
| I-38 | 123.5–124.5 | 1.20(6H, d, J=6.9), 1.23(6H, s), 1.38(6H, s), 2.67(2H, s), 2.80 (2H, s), 3.08(1H, sept, J=6.9), 4.32(2H, s), 4.49(2H, s), 6.87–6.91 (1H, m), 7.16–7.21(2H, m), 7.31–7.35(1H, m) |
| I-39 | | 0.88(6H, t, J=7.4), 1.20(6H, d, J=6.9), 1.47–1.62(4H, m), 2.61 (2H, s), 3.08(1H, sept, J=6.9), 3.93–3.97(2H, m), 4.43(2H, s), 5.15–5.19(1H, m), 5.28–5.39(1H, m), 5.86–6.01(1H, m), 6.89–6.94 (1H, m), 7.16–7.21(2H, m), 7.30–7.36(1H, m) |
| I-40 | | 0.87(6H, t, J=7.4), 1.20(6H, d, J=6.9), 1.28(3H, t, J=7.3), 1.42–1.60 (4H, m), 2.64(2H, s), 3.11(1H, sept, J=6.9), 4.06(2H, s), 4.21(2H, q, J=7.3), 4.43(2H, s), 6.91–6.96(1H, m), 7.15–7.19 (2H, m), 7.31–7.34(1H, m) |

TABLE 14

| Compound No | m.p. | NMR(CHCl₃) |
|---|---|---|
| I-41 | | 0.87(6H, t, J=7.4), 1.20(6H, d, J=6.9), 1.27(6H, d, J=7.0), 1.48–1.63(4H, m), 2.65(2H, s), 3.11(1H, sept, J=6.9), 4.02(2H, s), 4.43(2H, s), 5.01(1H, sept, J=7.0), 6.91–6.96(1H, m), 7.15–7.19 (2H, m), 7.31–7.34(1H, m) |
| I-42 | | 0.88(6H, t, J=7.4), 1.20(6H, d, J=6.9), 1.46(9H, s), 1.42–1.60 (4H, m), 2.64(2H, s), 3.11(1H, sept, J=6.9), 3.90(2H, s), 4.42 (2H, s), 6.89–6.96(1H, m), 7.18–7.23(2H, m), 7.31–7.34(1H, m) |
| I-43 | | 0.88(6H, t, J=7.4), 1.20(6H, d, J=6.9), 1.26(3H, t, J=7.0), 1.42–1.60 (4H, m), 2.60(2H, s), 2.79(2H, t, J=7.2), 3.08(1H, sept, J=6.9), 3.54(2H, t, J=7.2), 4.16(2H, q, J=7.0), 4.43(2H, s), 6.89–6.94(1H, m), 7.15–7.19(2H, m), 7.31–7.34(1H, m) |
| I-44 | | 0.88(6H, t, J=7.4), 1.19(6H, d, J=6.9), 1.50–1.70(4H, m), 1.71 (3H, d, J=6.9), 2.61(2H, s), 3.15(1H, sept, J=6.9), 3.88(2H, d, J=6.9), 4.43(2H, s), 5.56–5.62(1H, m), 5.69–5.78(1H, m), 6.89–6.94 (1H, m), 7.11–7.21(2H, m), 7.29–7.34(1H, m) |
| I-45 | | 0.88(6H, t, J=7.2), 1.19(6H, d, J=6.9), 1.48–1.65(4H, m), 1.72 (6H, d, J=6.9), 2.61(2H, s), 3.15(1H, sept, J=6.9), 3.89(2H, d, J=6.9), 4.44(2H, s), 5.28–5.35(1H, m), 6.87–6.92(1H, m), 7.11–7.21 (2H, m), 7.29–7.34(1H, m) |
| I-46 | | 0.88(6H, t, J=7.1), 1.19(6H, d, J=6.9), 1.48–1.65(4H, m), 2.47 (2H, q, J=7.4), 2.60(2H, s), 3.12(1H, sept, J=6.9), 3.34(2H, t, J=7.4), 4.44(2H, s), 5.01–5.14(2H, m), 5.74–5.98(1H, m), 6.82–6.89 (1H, m), 7.11–7.21(2H, m), 7.29–7.34(1H, m) |
| I-47 | | 0.85(3H, t, J=7.4), 1.18(3H, d, J=7.4), 1.23(6H, s), 1.26(3H, t, J=7.0), 1.42–1.60(4H, m), 2.68(2H, s), 3.11(1H, sext, J=7.0), 4.06(2H, s), 4.15(2H, q, J=7.0), 4.38(1H, d, J=13.5), 4.57(1H, d, J=13.5), 6.83–6.90(1H, m), 7.11–7.19(2H, m), 7.28–7.31(1H, m) |
| I-48 | | 0.85(3H, t, J=7.4), 1.18(3H, d, J=7.4), 1.23(6H, s), 1.47(9H, s), 1.42–1.60(4H, m), 2.68(2H, s), 3.00(1H, sext, J=7.0), 4.01(2H, s), 4.38(1H, d, J=13.5), 4.57(1H, d, J=13.5), 6.89–6.95(1H, m), 7.11–7.19(2H, m), 7.28–7.31(1H, m) |
| I-49 | | 0.82–0.91(9H, m), 1.17(3H, d, J=6.9), 2.61(2H, s), 2.87(1H, sext, J=6.9), 3.65(2H, d, J=6.9), 4.30(1H, d, J=13.5), 4.57(1H, d, J=13.5), 5.15–5.35(2H, m), 5.86–5.99(1H, m), 6.88–6.92(1H, m), 7.11–7.28(3H, m) |
| I-50 | | 0.83–0.92(9H, m), 1.18(3H, d, J=6.9), 1.47–1.69(6H, m), 2.06 (3H, s), 2.62(2H, s), 2.87(1H, sext, J=6.9), 3.58(2H, t, J=6.6), 4.31(1H, d, J=13.9), 4.35(2H, t, J=6.6), 4.55(1H, d, J=13.9), 6.88–6.91(1H, m), 7.11–7.20(2H, m), 7.25–7.29(1H, m) |

TABLE 15

| Compound No | m.p. | NMR(CHCl₃) |
|---|---|---|
| I-51 | | 0.83–0.92(9H, m), 1.18(3H, d, J=6.9), 2.53–2.56(4H, m), 2.60 (2H, s), 2.71(2H, t, J=7.3), 2.90(1H, sept, J=6.9), 3.45(2H, t, J=7.3), 3.69–3.73(6H, m), 4.32(1H, d, J=13.9), 4.55(1H, d, J=13.9), 6.89–6.91(1H, m), 7.14–7.20(2H, m), 7.25–7.29(1H, m) |
| I-52 | | 1.22(6H, s), 1.24(3H, t, J=7.3), 1.33(3H, t, J=7.2), 2.64(2H, q, J=7.3), 2.66(2H, s), 4.06(2H, s), 4.20(2H, q, J=7.2), 4.48(2H, s), 6.97(2H, d, J=8.3), 7.20(2H, d, J=8.3) |
| I-53 | | 1.22(6H, s), 1.26(6H, d, J=6.9), 1.29(3H, t, J=7.2), 2.70(2H, s), 2.94(1H, sept, J=6.9), 4.06(2H, s), 4.12(2H, q, J=7.2), 4.49(2H, s), 6.85–6.90(2H, m), 7.04–7.10(1H, m), 7.31–7.34(1H, m) |
| I-54 | | 1.23(6H, s), 1.29(3H, t, J=7.3), 2.68(2H, s), 2.72(6H, s), 4.07 (2H, s), 4.22(2H, q, J=7.3), 4.49(2H, s), 6.98–7.10(4H, m) |
| I-55 | | 1.27(6H, s), 1.33(3H, t, J=7.3), 2.73(2H, s), 3.01(6H, s), 4.10 (2H, s), 4.25(2H, q, J=7.3), 4.54(2H, s), 6.41(1H, d, J=2.3), 6.48 (1H, d, J=7.6), 6.60(1H, dd, J=7.6, 2.3), 7.20(1H, d, J=7.6) |
| I-56 | | 1.16(6H, t, J=7.3), 1.21(6H, s), 1.28(3H, t, J=7.3), 2.68(2H, s), 3.35(4H, q, J=7.3), 4.05(2H, s), 4.19(2H, q, J=7.3), 4.48(2H, s), 6.29(1H, d, J=2.3), 6.32(1H, d, J=8.6), 6.50(1H, dd, J=8.6, 2.3), 7.20(1H, d, J=8.6) |
| I-57 | | 1.21(6H, s), 1.22(3H, t, J=7.6), 1.46(9H, s), 2.65(2H, q, J=7.6), 2.69(2H, s), 3.96(2H, s), 4.48(2H, s), 6.97(2H, d, J=8.3), 7.20 (2H, d, J=8.3) |
| I-58 | | 1.21(6H, s), 1.25(6H, d, J=6.9), 1.56(9H, s), 2.69(2H, s), 2.90 (1H, sept, J=6.9), 3.97(2H, s), 4.48(2H, s), 6.85–6.90(2H, m), 7.04–7.10(1H, m), 7.31–7.34(1H, m) |

TABLE 15-continued

| Compound No | m.p. | Physical properties NMR(CHCl$_3$) |
|---|---|---|
| I-59 | | 1.21(6H, s), 1.56(9H, s), 2.67(2H, s), 2.69(6H, s), 3.96(2H, s), 4.47(2H, s), 6.98–7.10(4H, m) |
| I-60 | | 1.21(6H, s), 1.47(9H, s), 2.68(2H, s), 2.96(6H, s), 3.96(2H, s), 4.48(2H, s), 6.36(1H, d, J=7.6), 6.37(1H, d, J=2.3), 6.55(1H, dd, J=7.6, 2.3), 7.20(1H, d, J=7.6) |

TABLE 16

| Compound No | m.p. | Physical properties NMR(CHCl$_3$) |
|---|---|---|
| I-61 | | 1.16(6H, t, J=7.3), 1.21(6H, s), 1.57(9H, s), 2.68(2H, s), 3.35 (4H, q, J=7.3), 3.93(2H, s), 4.48(2H, s), 6.29(1H, d, J=2.3), 6.32 (1H, d, J=8.6), 6.50(1H, dd, J=8.6, 2.3), 7.20(1H, d, J=8.6) |
| I-62 | | 1.15(6H, t, J=7.2), 1.22(6H, s), 2.65(2H, s), 3.31(4H, q, J=7.3), 3.93–3.97(2H, m), 4.49(2H, s), 5.15–5.19(1H, m), 5.28–5.39(1H, m), 5.86–6.01(1H, m), 6.28(1H, d, J=2.2), 6.32(1H, d, J=8.6), 6.50(1H, dd, J=8.6, 2.2), 7.20(1H, d, J=8.6) |
| I-63 | | 0.97(6H, t, J=7.2), 1.22(6H, s), 2.15(3H, s), 2.64(2H, s), 2.97 (4H, q, J=7.3), 3.93–3.97(2H, m), 4.49(2H, s), 5.15–5.19(1H, m), 5.28–5.39(1H, m), 5.86–6.01(1H, m), 6.64(1H, d, J=7.9), 6.90 (1H, d, J=7.9), 7.15(1H, d, J=7.9) |
| I-64 | | 1.22(6H, s), 2.16(3H, s), 2.64(2H, s), 2.68(6H, s), 3.93–3.97 (2H, m), 4.49(2H, s), 5.15–5.19(1H, m), 5.28–5.39(1H, m), 5.86–6.01(1H, m), 6.63(1H, d, J=7.9), 6.85(1H, d, J=7.9), 7.12 (1H, d, J=7.9) |
| I-65 | | 0.88(6H, t, J=7.3), 1.43–1.65(4H, m), 2.60(2H, s), 2.70(6H, s), 3.94(2H, d, J=6.9), 4.43(2H, s), 5.16(2H, d, J=10.2), 5.31(1H, dd, J=16.8, 1.3), 5.86–6.01(1H, m), 6.93–7.03(3H, m), 7.08–7.14 (1H, m) |
| I-66 | | 0.87(6H, t, J=7.3), 1.47(9H, s), 1.48–1.63(4H, m), 2.62(2H, s), 2.70(6H, s), 3.96(2H, s), 4.43(2H, s), 6.92–7.14(4H, m) |
| I-67 | | 0.88(6H, t, J=7.6), 1.47–1.65(4H, m), 2.60(2H, s), 3.82(3H, s), 3.92–3.95(2H, m), 4.48(2H, s), 5.14–5.19(1H, m), 5.32(1H dd, J=16.8, 1.3), 5.87–6.00(1H, m), 6.93–7.00(3H, m), 7.10–7.17(1H, m) |
| I-68 | | 0.87(6H, t, J=7.6), 1.47(9H, s), 1.51–1.60(4H, m), 2.63(2H, s), 3.83(3H, s), 3.96(2H, s), 4.47(2H, s), 6.93–7.03(3H, m), 7.10–7.14 (1H, m) |
| I-69 | | 0.86(6H, t, J=7.6), 1.24(3H, t, J=7.6), 1.41–1.65(4H, m), 2.61–2.71 (4H, m), 3.94(2H, d, J=7.3), 4.45(2H, s), 5.16(1H, d, J=9.9), 5.28–5.34(1H, m), 5.86–6.01(1H, m), 6.94–6.98(1H, m), 7.18–7.21(2H, m) |
| I-70 | | 0.88(6H, t, J=7.6), 1.47(9H, s), 1.49–1.58(4H, m), 2.61–2.70 (4H, m), 3.97(2H, s), 4.45(2H, s), 6.96–6.99(2H, m), 7.18–7.21 (2H, m) |

TABLE 17

| Compound No | m.p. | Physical properties NMR(CHCl$_3$) |
|---|---|---|
| I-71 | | 0.89(6H, t, J=7.6), 1.47–1.65(4H, m), 2.64(2H, s), 3.94(2H, d, J=7.3), 4.45(2H, s), 5.18(1H, d, J=9.9), 5.32(1H, dd, J=17.2, 1.3), 5.86–6.01(1H, m), 7.01–7.06(2H, m), 7.20–7.23(2H, m) |
| I-72 | | 0.88(6H, t, J=7.3), 1.47(9H, s), 1.48–1.66(4H, m), 2.67(2H, s), 3.97(2H, s), 4.44(2H, s), 7.03–7.08(2H, m), 7.20–7.26(2H, m) |
| I-73 | 103.5–104.5 | 0.88(6H, t, J=7.3), 1.50–1.63(4H, m), 2.62(2H, s), 2.72(6H, s), 3.43(3H, s), 4.43(2H, s), 5.45(2H, s), 6.95–7.18(4H, m) |
| I-74 | | 1.20(6H, d, J=6.9), 1.60–1.87(8H, m), 2.74(2H, s), 3.10(1H, sept, J=6.9), 3.93–3.96(2H, m), 5.15(1H, dd, J=9.9, 1.3), 5.31 (1H, dd, J=17.1, 1.3), 5.86–6.01(1H, m), 6.90–9.94(1H, m), 7.12–7.20(2H, m), 7.31–7.34(1H, m) |
| I-75 | | 1.62–1.86(8H, m), 2.72(6H, s), 3.92–3.95(2H, m), 4.55(2H, s), 5.15(1H, d, J=10.0), 5.26–5.33(1H, m), 5.86–5.98(1H, m), 6.93–7.01 (3H, m), 7.09–7.16(1H, m) |

TABLE 17-continued

| Compound No | m.p. | Physical properties NMR(CHCl$_3$) |
|---|---|---|
| I-76 | | 1.47(9H, s), 1.64–1.76(8H, m), 2.71(6H, s), 2.76(2H, s), 3.95 (2H, s), 4.54(2H, s), 6.92–7.05(3H, m), 7.09–7.15(1H, m) |
| I-77 | 85.5–87.5 | 1.20(6H, d, J=6.9), 1.60–1.84(8H, m), 2.79(2H, s), 3.09(1H, sept, J=6.9), 3.40(3H, s), 3.61–3.64(2H, m), 4.09(2H, s), 4.29–4.32 (2H, m), 4.52(2H, s), 6.92–6.95(1H, m), 7.13–7.20(2H, m), 7.31–7.34(1H, m) |
| I-78 | | 1.19(6H, d, J=6.9), 1.60–1.87(8H, m), 2.23(3H, s), 2.76(2H, s), 3.06(1H, sept, J=6.9), 4.53(2H, s), 4.57(2H, s), 6.09(1H, s), 6.87–6.92(1H, m), 7.13–7.20(2H, m), 7.29–7.34(1H, m) |
| I-79 | | 1.64–1.84(8H, m), 2.75(2H, s), 3.83(3H, s), 3.93(2H, d, J=6.9), 4.56(2H, s), 5.16(1H, d, J=9.9), 5.31(1H, dd, J=17.1, 1.7), 5.87–5.99(1H, m), 6.92–7.01(3H, m), 7.11–7.18(1H, m) |
| I-80 | | 1.47(9H, s), 1.64–1.83(8H, m), 2.78(2H, s), 3.84(3H, s), 3.96 (2H, s), 4.55(2H, s), 6.92–7.04(3H, m), 7.11–7.18(1H, m) |

TABLE 18

| Compound No | m.p. | Physical properties NMR(CHCl$_3$) |
|---|---|---|
| I-81 | | 1.57–1.86(8H, m), 2.73(6H, s), 2.74(2H, s), 3.42(3H, s), 4.55 (2H, s), 5.44(2H, s), 6.94–7.04(3H, m), 7.11–7.17(1H, m) |
| I-82 | | 1.24(3H, t, J=7.6), 1.65–1.87(8H, m), 2.65(2H, m), 3.93–3.95 (2H, m), 4.54(2H, m), 5.16(1H, d, J=9.9), 5.27–5.35(1H, m), 5.86–6.01(1H, m), 6.93–6.98(2H, m), 7.19–7.22(1H, m) |
| I-83 | | 1.55–1.84(8H, m), 2.77(2H, s), 3.92–3.95(2H, m), 4.55(2H, s), 5.18(1H, d, J=9.9), 5.28–5.35(1H, m), 5.86–6.01(1H, m), 7.01–7.06 (2H, m), 7.22(2H, d, J=8.9) |
| I-84 | | 1.37–1.60(8H, m), 1.73–1.86(2H, m), 2.65(2H, s), 2.70(6H, s), 3.94(2H, d, J=7.3), 4.52(2H, s), 5.15(1H, d, J=9.9), 5.30(1H, dd, J=17.2, 1.3), 5.86–6.01(1H, m), 6.93–7.15(4H, m) |
| I-85 | | 1.36–1.62(8H, m), 1.47(9H, s), 1.69–1.82(2H, m), 2.67(2H, s), 2.70(6H, s), 3.79(2H, s), 4.52(2H, s), 6.93–7.14(4H, m) |
| I-86 | 108.5–109.5 | 1.33–1.62(8H, m), 1.75–1.82(2H, m), 2.65(2H, s), 3.82(3H, s), 3.94(2H, d, J=6.9), 4.56(2H, s), 5.15(1H, d, J=10.2), 5.31(1H, dd, J=17.2, 1.6), 5.88–6.02(1H, m), 6.93–7.02(3H, m), 7.10–7.17 (1H, m) |
| I-87 | | 1.23–1.78(10H, m), 1.46(9H, s), 2.67(2H, s), 3.83(3H, s), 3.97 (2H, s), 4.55(2H, s), 6.89–7.05(3H, m), 7.10–7.17(12H, m) |
| I-88 | 98–100 | 1.24(3H, t, J=7.6), 1.36–1.54(8H, m), 1.76–1.81(2H, m), 2.61–2.69 (4H, m), 3.94(2H, d, J=6.9), 4.53(2H, s), 5.16(1H, d, J=9.9), 5.27–5.34(1H, m), 5.86–5.98(1H, m), 6.95–6.98(2H, m), 7.18–7.21(2H, m) |
| I-89 | | 1.20(6H, d, J=6.9), 1.37–1.90(16H, m), 2.66(2H, s), 3.10(1H, sept, J=6.9), 3.47–3.59(3H, m), 3.69–4.06(3H, m), 4.45(1H, d, J=13.9), 4.59(1H, d, J=13.9), 4.65–4.68(1H, m), 6.90–6.93(1H, m), 7.12–7.19(2H, m), 7.29–7.34(1H, m) |
| I-90 | | 1.20(6H, d, J=6.9), 1.30–1.60(8H, m), 1.72–1.83(2H, m), 2.04 (2H, brs), 2.67(2H, s), 3.09(1H, sept, J=6.9), 3.56(2H, t, J=5.9), 3.93(2H, brs), 4.51(2H, s), 6.91–6.94(1H, m), 7.13–7.21(2H, m), 7.29–7.34(1H, m) |

TABLE 19

| Compound No | m.p. | Physical properties NMR(CHCl$_3$) |
|---|---|---|
| I-91 | | 1.30–1.63(8H, m), 1.75–1.82(2H, m), 2.68(2H, s), 3.93–3.96(2H, m), 4.54(2H, s), 5.17(1H, dd, J=9.9, 1.3), 5.28–5.35(1H, m), 5.86–6.01(1H, m), 7.01–7.07(2H, m), 7.20–7.23(2H, m) |
| I-92 | 73.5–75.0 | 1.20(6H, d, J=6.9), 1.58–1.67(2H, m), 1.89–1.95(2H, m), 2.73 (2H, s), 3.09(1H, sept, J=6.6), 3.94(2H, d, J=7.3), 4.66(2H, s), 5.18(1H, d, J=9.9), 5.29–5.36(1H, m), 5.87–5.98(1H, m), 7.15–7.19 (2H, m), 7.31–7.35(1H, m) |

TABLE 19-continued

| Compound No | m.p. | NMR(CHCl₃) |
|---|---|---|
| I-93 | 127–128 | 1.21(6H, d, J=6.6), 1.55–1.67(2H, m), 1.89–1.97(2H, m), 2.65 (3H, s), 2.74(2H, s), 3.09(1H, sept, J=6.6), 3.69–3.76(4H, m), 4.69(2H, s), 6.89–6.92(1H, m), 7.13–7.21(2H, m), 7.30–7.35(1H, m) |
| I-94 | | 0.90(6H, t, J=7.3), 1.20(6H, d, J=7.3), 1.48–1.62(4H, m), 2.69 (2H, s), 3.05(1H, sept, J=7.3), 4.16(2H, s), 4.38(2H, s), 4.97 (1H, brs), 6.92–6.96(1H, m), 7.13–7.21(2H, m), 7.32–7.36(1H, m) |
| I-95 | 98–99 | 1.23(6H, s), 2.65(2H, s), 4.00(2H, d, J=6.9), 4.58(2H, s), 5.19 (1H, d, J=6.9), 5.35(1H, dd, J=17.2, 1.3), 5.90–6.03(1H, m), 7.09 (1H, d, J=7.3), 7.42–7.53(3H, m), 7.67(1H, d, J=8.2), 7.85(1H, dd, J=7.3, 3.0), 8.05(1H, d, J=6.9) |
| I-96 | 120–121 | 1.23(6H, s), 1.49(9H, s), 2.69(2H, s), 4.01(2H, s), 4.57(2H, s), 7.11(1H, d, J=8.2), 7.42–7.51(3H, m), 7.67(1H, d, J=8.2), 7.84–7.87 (1H, m), 8.06(1H, d, J=7.6) |
| I-97 | | 1.23(6H, s), 2.69(2H, s), 3.40(3H, s), 3.61–3.65(2H, m), 4.15 (2H, s), 4.30–4.33(2H, m), 4.56(2H, s), 7.11(1H, dd, J=7.3, 1.0), 7.42–7.54(3H, m), 7.67(1H, d, J=8.2), 7.84–7.88(1H, m), 8.04 (1H, dd, J=6.9, 3.3) |
| I-98 | 99–100 | 0.92(6H, t, J=7.3), 1.22–1.60(4H, m), 2.62(2H, s), 4.00(2H, s), 4.54(2H, s), 5.19(1H, d, J=9.9), 5.35(1H, dd, J=7.2, 1.7), 5.93–6.03(1H, m), 7.09(1H, d, J=7.3), 7.42–7.52(3H, m), 7.66 (1H, d, J=8.2), 7.83–7.86(1H, m), 8.06(1H, d, J=7.9) |
| I-99 | 111–113 | 0.90(6H, t, J=6.9), 1.16–1.56(4H, m), 1.49(9H, s), 2.65(2H, s), 4.02(2H, s), 4.54(2H, s), 7.10–7.12(1H, m), 7.42–7.53(3H, m), 7.66(1H, d, J=8.2), 7.83–7.86(1H, m), 8.05–8.08(1H, m) |
| I-100 | 86–87 | 0.90(6H, t, J=7.3), 1.43–1.66(4H, m), 2.63(2H, s), 4.00(2H, d, J=6.9), 4.54(2H, s), 5.20(2H, d, J=9.9), 5.35(1H, dd, J=16.8, 1.3), 5.90–6.05(1H, m), 7.15–7.18(1H, m), 7.38(1H, dd, J=8.6, 4.3), 7.69(1H, dd, J=8.6, 7.3), 7.92(1H, d, J=8.6), 8.45(1H, d, J=7.3), 8.93(1H, dd, J=4.3, 1.7) |

TABLE 20

| Compound No | m.p. | NMR(CHCl₃) |
|---|---|---|
| I-101 | 103–104 | 1.59–1.84(8H, m), 2.74(2H, s), 3.97(2H, d, J=6.9), 4.61(2H, s), 5.17(1H, d, J=10.2), 5.32(1H, dd, J=16.8, 1.3), 5.88–6.01(1H, m), 7.08(1H, d, J=8.2), 7.41–7.52(3H, m), 7.60(1H, d, J=8.2), 7.84(1H, dd, J=7.3, 2.6), 8.02(1H, d, J=6.6) |
| I-102 | | 1.49(9H, s), 1.54–1.90(8H, m), 2.79(2H, s), 4.00(2H, s), 4.61 (2H, s), 7.11(1H, dd, J=7.6, 1.3), 7.42–7.53(3H, m), 7.67(1H, d, J=8.2), 7.84–7.89(1H, m), 8.02–8.06(1H, m) |
| I-103 | | 1.58–1.85(8H, m), 2.77(2H, s), 3.99(2H, d, J=7.3), 4.62(2H, s), 5.19(1H, d, J=8.9), 5.31–5.38(1H, m), 5.91–6.04(1H, m), 7.17 (1H, d, J=7.6), 7.39(1H, dd, J=8.6, 4.3), 7.66–7.73(1H, m), 7.93 (1H, d, J=8.6), 8.42(1H, d, J=8.6), 8.93(1H, dd, J=4.3, 2.0) |
| I-104 | 109–110 | 1.33–1.84(10H, m), 2.66(2H, s), 4.00(2H, d, J=6.9), 4.63(2H, s), 5.19(1H, d, J=9.9), 5.35(1H, dd, J=16.8, 1.3), 5.91–6.06(1H, m), 7.10(1H, d, J=7.3), 7.42–7.52(3H, m), 7.66(1H, J=8.2), 7.83–7.86 (1H, m), 8.06(1H, d, J=7.3) |
| I-105 | | 1.30–1.63(8H, m), 1.72–1.84(2H, m), 2.68(2H, s), 4.00(2H, d, J=6.9), 4.62(2H, s), 5.20(1H, d, J=9.9), 5.35(1H, dd, J=16.8, 1.3), 5.92–6.04(1H, m), 7.17(1H, d, J=6.9), 7.38(1H, dd, J=8.6, 4.3), 7.66–7.72(1H, m), 7.93(1H, d, J=8.6), 8.45(1H, d, J=8.6), 8.93(1H, dd, J=4.3, 1.7) |
| I-106 | | 1.15(6H, s), 1.22(6H, d, J=6.9), 2.67(2H, s), 3.02(1H, sept, J=6.9), 4.08(2H, s), 6.77–6.80(1H, m), 7.07–7.18(2H, m), 7.28–7.31 (1H, m), 7.77(1H, dd, J=8.6, 2.6), 8.11(1H, d, J=8.9), 8.57–8.58 (1H, m) |
| I-107 | 121.5–122.5 | 1.23(6H, d, J=6.9), 1.27(6H, s), 2.80(2H, s), 3.17(1H, sept, J=6.9), 4.36(2H, s), 6.80–6.84(1H, m), 7.13–7.23(3H, m), 7.32–7.42 (2H, m), 7.70–7.79(2H, m) |
| I-108 | 158.5–159.5 | 1.20(6H, s), 1.27(6H, d, J=6.9), 2.72(2H, s), 3.29(1H, sept, J=6.9), 3.99(2H, s), 6.80–6.84(1H, m), 7.09–7.39(6H, m), 7.53–7.56 (1H, m) |

TABLE 20-continued

| Compound No | Physical properties m.p. | NMR(CHCl$_3$) |
|---|---|---|
| I-109 | | 1.16(6H, s), 1.23(6H, d, J=6.9), 2.67(2H, s), 3.00(1H, sept, J=6.9), 4.19(2H, s), 6.79–6.83(1H, m), 7.11–7.21(2H, m), 7.30–7.34 (1H, m), 8.18(1H, d, J=9.2), 8.32(1H, dd, J=9.2, 2.6), 9.17 (1H, d, J=2.6) |
| I-110 | | 0.94(2H, t, J=7.3), 1.14(6H, s), 1.57–1.71(2H, m), 2.57(2H, t, J=7.3), 2.67(2H, s), 4.09(2H, s), 6.81–6.87(2H, m), 7.08–7.16 (2H, m), 7.75(1H, dd, J=8.9, 2.6), 8.09(1H, d, J=8.9), 8.55(1H, s) |

TABLE 21

| Compound No | m.p. | NMR(CHCl$_3$) |
|---|---|---|
| I-111 | | 0.88(6H, t, J=7.4), 1.22(6H, d, J=6.9), 1.42–1.52(4H, m), 2.61 (2H, s), 3.06(1H, sept, J=6.9), 4.11(2H, s), 6.75–6.80(1H, m), 7.07–7.18(2H, m), 7.29–7.34(1H, m), 7.75(1H, dd, J=8.6, 2.6), 8.08(1H, d, J=8.9), 8.57–8.58(1H, m) |
| I-112 | | 1.20(6H, d, J=6.9), 1.28(6H< s), 2.85(2H, s), 2.95(1H, sept, J=6.9), 4.34(2H, s), 6.72–6.79(1H, m), 7.14–7.20(2H, m), 7.31–7.36 (1H, m) |
| I-113 | 120–121 | 1.19(6H, d, J=6.9), 1.58–1.66(2H, m), 1.88–1.98(2H, m), 2.38–2.60 (4H, m), 2.64(3H, s), 2.69(2H, s), 3.08(1H, sept, J=6.9), 3.52(2H, s), 4.59(2H, s), 6.89–6.92(1H, m), 7.12–7.34(8H, m) |
| I-114 | | 0.89(6H, t, J=7.3), 1.43–1.65(4H, m), 2.49(3H, s), 2.62(2H, s), 3.93–3.96(2H, m), 4.45(2H, s), 5.17(1H, m), 5.31(1H, m), 5.89 (1H, m), 6.80(1H, m), 6.91(1H, m), 7.04(1H, m), 7.24–7.30(2H, m) |
| I-115 | | 1.57–1.88(8H, m), 2.49(3H, s), 2.75(2H, s), 3.95(2H, m), 4.55 (2H, s), 5.17(1H, m), 5.32(1H, m), 5.93(1H, m), 6.80(1H, m), 6.91(1H, m), 7.05(1H, m), 7.29(1H, m) |
| I-116 | | 1.32–1.60(8H, m), 1.72–1.84(2H, m), 2.49(3H, s), 2.66(2H, s), 3.95(2H, m), 4.54(2H, s), 5.17(1H, d, J=10.2), 5.32(1H, dd, J=17.2, 1.3), 5.89(1H, m), 6.80(1H, m), 6.91(1H, m), 7.04(1H, m), 7.28(1H, m) |
| I-117 | | 1.65–1.86(8H, m), 2.49(3H, s), 2.75(2H, s), 3.93(2H, m), 4.54 (2H, s), 5.17(1H, m), 5.31(1H, m), 5.89(1H, m), 6.96–7.01(2H, m), 7.26–7.31(2H, m) |
| I-118 | 111–112 | 1.37–1.63(8H, m), 1.73–1.84(2H, m), 2.49(3H, s), 2.67(2H, s), 3.94(2H, m), 4.53(2H, s), 5.17(1H, d, J=10.2), 5.31(1H, dd, J=17.2, 1.7), 5.92(1H, m), 6.97–7.01(2H, m), 7.26–7.30(2H, m) |
| I-119 | | 1.22(6H, s), 1.25(3H, t, J=6.9), 2.62(2H, s), 2.65(2H, q, J=6.9), 3.81(3H, s), 3.95(2H, m), 4.50(2H, s), 5.17(1H, m), 5.29(1H, m), 5.94(1H, m), 6.80–6.84(2H, m), 6.93(1H, m). |
| I-120 | | 1.22(6H, s), 1.24(6H, d, J=6.9), 2.64(2H, s), 2.89(1H, sept, J=6.9), 3.82(3H, s), 3.95(2H, m), 4.49(2H, s), 5.17(1H, m), 5.28(1H, m), 5.94(1H, m), 6.89–6.94(2H, m), 6.93(1H, m). |
| I-121 | | 1.18(6H, d, J=6.9), 1.22(6H, s), 2.64(2H, s), 3.10(1H, sept, J=6.9), 3.81(3H, s), 3.95(2H, m), 4.47(2H, s), 5.17(1H, m), 5.28(1H, m), 5.97(1H, m), 6.72(1H, m), 6.85–6.95(2H, m). |
| I-122 | | 1.17(6H, d, J=6.9), 1.22(6H, s), 1.43(3H, t, J=7.5), 2.65(2H, s), 3.05(1H, sept, J=6.9), 3.95(2H, m), 4.05(2H, q, J=7.5), 4.46 (2H, s), 5.17(1H, m), 5.28(1H, m), 5.97(1H, m), 6.72(1H, m), 6.85–6.90(2H, m). |

TABLE 22

| Compound No | m.p. | NMR(CHCl$_3$) |
|---|---|---|
| I-123 | | 1.22(6H, s), 1.45(6H, t, J=7.4), 2.64(2H, s), 3.95(2H, m), 4.10 (4H, q, J=7.4), 4.48(2H, s), 5.17(1H, m), 5.28(1H, m), 5.97(1H, m), 6.55–6.63(2H, m), 6.88(1H, m). |
| I-124 | | 1.05(6H, t, J=7.4), 1.22(6H, s), 1.78–1.86(4H, m), 2.66(2H, s), 3.93(4H, q, J=7.4), 3.95(2H, m), 4.48(2H, s), 5.17(1H, m), 5.28 (1H, m), 5.97(1H, m), 6.55–6.68(2H, m), 6.88(1H. m). |

TABLE 22-continued

| Compound | Physical properties | |
|---|---|---|
| No | m.p. | NMR(CHCl$_3$) |
| I-125 | 86–88 | 1.23(6H, s), 1.45(3H, t, J=7.4), 2.67(2H, s), 3.22(3H, s), 3.95 (2H, m), 4.12(2H, q, J=7.4), 4.47(2H, s), 5.17(1H, m), 5.28(1H, m), 5.97(1H, m), 6.95–6.99(2H, m), 7.12(1H, m). |
| I-126 | 65–66 | 1.22(6H, s), 1.25(3H, t, J=6.9), 2.65(2H, s), 3.54(2H, q, J=6.9), 3.95(2H, m), 4.49(2H, s), 5.17(1H, m), 5.28(1H, m), 5.97(1H, m), 6.99(2H, d, J=7.9), 7.34(2H, d, J=7.9). |
| I-127 | | 0.88(6H, t, J=7.4), 1.45(3H, t, J=7.4), 1.44–1.58(4H, m), 2.62 (2H, s), 3.80(3H, s), 3.95(2H, m), 4.11(2H, q, J=7.4), 4.45(2H, s), 5.17(1H, m), 5.28(1H, m), 5.97(1H, m), 6.50–6.65(2H, m), 6.88(1H, m). |
| I-128 | | 0.88(6H, t, J=7.4), 1.45(6H, t, J=7.4), 1.44–1.58(4H, m), 2.62 (2H, s), 3.95(2H, m), 4.11(4H, q, J=7.4), 4.45(2H, s), 5.17(1H, m), 5.28(1H, m), 5.97(1H, m), 6.55–6.65(2H, m), 6.88(1H, m). |
| I-129 | 62–64 | 0.88(6H, t, J=7.4), 1.04(3H, t, J=7.4), 1.43(3H, t, J=7.4), 1.44–1.58 (4H, m), 1.86(2H, sext, J=7.4), 2.62(2H, s), 3.95(2H, m), 3.98(2H, t, J=7.4), 4.10(2H, q, J=7.4), 4.49(2H, s), 5.13(1H, m), 5.28(1H, m), 5.97(1H, m), 6.55–6.65(2H, m), 6.88(1H, m). |
| I-130 | 104–105 | 0.88(6H, t, J=7.4), 1.06(3H, t, J=7.4), 1.44–1.58(4H, m), 1.86 (2H, sext, J=7.4), 2.62(2H, s), 3.21(3H, s), 3.95(2H, m), 3.98 (2H, t, J=7.4), 4.43(2H, s), 5.13(1H, m), 5.28(1H, m), 5.97(1H, m), 6.84–6.88(2H, m), 7.13(1H, m). |
| I-131 | 70–72 | 0.88(6H, t, J=7.4), 1.04(6H, t, J=7.4), 1.44–1.58(4H, m), 1.86 (4H, m), 2.64(2H, s), 3.95(2H, m), 3.98(2H, t, J=7.4), 4.49(2H, s), 5.13(1H, m), 5.28(1H, m), 5.97(1H, m), 6.55–6.65(2H, m), 6.88(1H, m). |
| I-132 | 59–60 | 0.88(6H, t, J=7.4), 1.04(3H, t, J=7.4), 1.35(6H, d, J=6.9), 1.44–1.58 (4H, m), 1.79(2H, sext, J=7.4), 2.62(2H, s), 3.95(2H, m), 3.98(2H, t, J=7.4), 4.46(1H, sept, J=6.9), 4.46(2H, s), 5.13(1H, m), 5.28(1H, m), 5.97(1H, m), 6.52–6.61(2H, m), 6.88(1H, m). |
| I-133 | | 1.22(6H, s), 2.30(6H, s), 2.51–2.60(2H, m), 2.65(2H, s), 2.81–2.88 (2H, m), 3.95(2H, m), 4.49(2H, s), 5.17(1H, m), 5.28(1H, m), 5.97(1H, m), 6.98(2H, d, J=7.9), 7.20(2H, d, J=7.9). |

TABLE 23

| Compound | Physical properties | |
|---|---|---|
| No | m.p. | NMR(CHCl$_3$) |
| I-134 | | 1.20(6H, d, J=6.9), 1.32–1.60(8H, m), 1.47(9H, s), 1.70–1.81 (2H, m), 2.70(2H, s), 3.09(1H, sept, J=6.9), 3.97(2H, s), 4.52 (2H, s), 6.95(1H, m), 7.11–7.20(2H, m), 7.31(1H, m) |
| I-135 | | 1.20(6H, d, J=6.9), 1.58–1.68(2H, m), 1.93–1.97(2H, m), 2.31 (3H, s), 2.38–2.59(4H, m), 2.64(3H, s), 2.68(2H, s), 3.09(1H, sept, J=6.9), 4.59(2H, s), 6.91(1H, m), 7.13–7.21(2H, m), 7.33 (1H, m) |
| I-136 | | 1.11(3H, t, J=6.9), 1.20(6H, d, J=6.9), 1.65–1.70(2H, m), 1.94–2.00 (2H, m), 2.41–2.50(4H, m), 2.56–2.69(2H, m), 2.65(3H, s), 2.69(2H, s), 3.09(1H, sept, J=6.9), 4.60(2H, s), 6.91(1H, m), 7.13–7.21(2H, m), 7.33(1H, m) |
| I-137 | 67–68 | 1.22(6H, s), 2.65(2H, s), 3.93–3.97(2H, m), 4.45(2H, s), 5.17 (1H, m), 5.28(1H, m), 5.97(1H, m), 6.85–6.91(2H, m), 7.02(1H, m). |
| I-138 | 80–82 | 1.22(6H, s), 2.66(2H, s), 3.95(2H, m), 4.46(2H, s), 5.17(1H, m), 5.28(1H, m), 5.97(1H, m), 6.85(1H, dd, J=8.2, 2.0), 7.16 (1H, d, J=2.0), 7.44(1H, d, J=8.2). |
| I-139 | | 1.22(6H, s), 2.21(3H, s), 2.64(2H, s), 3.93–3.97(2H, m), 4.51 (2H, s), 5.17(1H, s), 5.28(1H, m), 5.97(1H, m), 6.85(1H, d, J=8.2), 7.16(1H, dd, J=8.2, 2.0), 7.22(1H, d, J=2.0). |
| I-140 | | 1.22(6H, s), 2.30(3H, s), 2.64(2H, s), 3.95(2H, m), 4.51(2H, s), 5.17(1H, m), 5.28(1H, m), 5.97(1H, m), 6.89(1H, d, J=8.2), 7.16(1H, dd, J=8.2, 2.0), 7.30(1H, d, J=2.0). |

TABLE 23-continued

| Compound | Physical properties | |
|---|---|---|
| No | m.p. | NMR(CHCl$_3$) |
| I-141 | | 1.22(6H, s), 2.65(2H, s), 2.88(2H, t, J=7.1), 3.36(3H, s), 3.66 (2H, t, J=7.1), 3.95(2H, m), 4.49(2H, s), 5.17(1H, m), 5.28(1H, m), 5.97(1H, m), 6.98(2H, d, J=8.3), 7.20(2H, d, J=8.3). |
| I-142 | | 1.25(6H, d, J=6.9), 1.55–1.87(8H, m), 2.72(2H, s), 2.91(1H, sept, J=6.9), 3.93(2H, m), 4.54(2H, s), 5.16(1H, m), 5.30(1H, m), 5.93(1H, m), 6.95–7.00(2H, m), 7.21–7.24(2H, m) |
| I-143 | | 1.25(6H, d, J=6.9), 1.47(9H, s), 1.63–1.85(8H, m), 2.78(2H, s), 2.91(1H, sept, J=6.9), 3.95(2H, s), 4.53(2H, ), 6.96–7.01(2H, m), 7.20–7.24(2H, m) |

TABLE 24

| Compound | Physical properties | |
|---|---|---|
| No | m.p. | NMR(CHCl$_3$) |
| I-144 | | 0.88(6H, t, J=7.3), 1.25(6H, d, J=6.9), 1.43–1.68(4H, m), 2.61 (2H, s), 2.90(1H, sept, J=6.9), 3.94(2H, m), 4.45(2H, s), 5.15 (1H, m), 5.31(1H, m), 5.94(1H, m), 6.95–6.99(2H, m), 7.20–7.24 (2H, m) |
| I-145 | | 0.87(6H, t, J=7.3), 1.25(6H, d, J=6.9), 1.47(9H, s), 1.48–1.70 (4H, m), 2.65(2H, s), 2.90(1H, sept, J=6.9), 3.96(2H, s), 4.44 (2H, s), 6.97–7.01(2H, m), 7.20–7.23(2H, m) |
| I-146 | 90.5–92.5 | 1.25(6H, d, J=6.9), 1.30–1.62(8H, m), 1.73–1.85(2H, m), 2.66 (2H, s), 2.91(1H, sept, J=6.9), 3.94(2H, m), 4.54(2H, s), 5.16 (1H, dd, J=9.9, 1.3), 5.31(1H, m), 5.94(1H, m), 6.96–7.00(2H, m), 7.20–7.24(2H, m) |
| I-147 | | 0.90(6H, t, J=6.9), 1.15–1.57(8H, m), 1.47(9H, s), 2.64(2H, s), 3.83(3H, s), 3.96(2H, s), 4.46(2H, s), 6.92–6.97(2H, m), 7.02 (1H, dd, J=7.9, 1.6), 7.13(1H, m) |
| I-148 | | 1.00(6H, d, J=6.9), 1.06(6H, d, J=6.9), 1.46(9H, s), 2.01(2H, sept, J=6.9), 2.80(2H, s), 3.82(3H, s), 3.87(2H, s), 4.66(2H, s), 6.91–7.01(3H, m), 7.13(1H, m) |
| I-149 | | 0.92(6H, t, J=7.3), 1.16–1.54(8H, m), 2.61(2H, s), 3.82(3H, s), 3.94(2H, dd, J=6.9, 1.0), 4.47(2H, s), 5.16(1H, m), 5.32(1H, m), 5.94(1H, m), 6.92–7.01(3H, m), 7.13(1H, m) |
| I-150 | | 0.85(3H, t, J=7.3), 1.18(3H, d, J=6.9), 1.47–1.68(4H, m), 1.90–2.00 (2H, m), 2.31(3H, s), 2.39–2.63(4H, m), 2.65(3H, s), 2.69 (2H, d, J=2.3), 2.89(1H, sext, J=7.3), 4.46(1H, d, J=13.8), 4.71 (1H, d, 13.8), 6.92(1H, m), 7.12–7.29(3H, m) |
| I-151 | | 1.37–1.63(8H, m), 1.48(9H, s), 1.70–1.83(2H, m), 2.67(2H, s), 4.02(2H, s), 4.62(2H, s), 7.11(1H, dd, J=7.6, 1.3), 7.42–7.53 (3H, m), 7.67(1H, d, J=8.2), 7.85(1H, dd, J=6.9, 3.3), 8.07(1H, m) |
| I-152 | | 0.88(6H, t, J=7.3), 1.44–1.65(4H, m), 1.49(9H, s), 2.65(2H, s), 4.02(2H, s), 4.54(2H, s), 7.11(1H, dd, J=7.3, 1.0), 7.42–7.53 (3H, m), 7.67(1H, d, J=8.2), 7.85(1H, dd, J=5.6, 3.3), 8.07(1H, dd, J=7.3, 3.3) |
| I-153 | | 1.21(6H, d, J=6.9), 1.58–1.67(2H, m), 2.31(3H, s), 2.33(3H, s), 2.41–2.45(4H, m), 2.67(2H, s), 3.13(1H, sept, J=6.9), 3.89(2H, s), 6.80(1H, m), 7.10–7.18(2H, m), 7.31(1H, m) |
| I-154 | | 0.85(3H, t, J=7.3), 1.19(3H, d, J=7.3), 1.47–1.81(6H, m), 2.31 (3H, s), 2.32(3H, s), 2.40–2.50(4H, m), 2.67(2H, s), 2.92(1H, sext, J=7.3), 3.84(1H, d, J=13.9), 6.80(1H, m), 7.11–7.17(2H, m), 7.25(1H, m) |

The compounds shown the following Tables include in the compound of the present invention. These compounds are synthesized in a similar manner to above Examples. Numbers in column of the left side of Table show compound No.

TABLE 25

| | $R^1$ | $R^2$ | $R^3$ | $R^4$ | $R^5$ | $R^6$ | $R^7$ | $R^8$ |
|---|---|---|---|---|---|---|---|---|
| A-1 | H | H | H | H | H | Allyl | Me | Me |
| A-2 | Cl | H | H | H | H | Allyl | Me | Me |
| A-3 | Br | H | H | H | H | Allyl | Me | Me |
| A-4 | Me | H | H | H | H | Allyl | Me | Me |
| A-5 | Et | H | H | H | H | Allyl | Me | Me |
| A-6 | Pr | H | H | H | H | Allyl | Me | Me |
| A-7 | Bu | H | H | H | H | Allyl | Me | Me |
| A-8 | $Bu^i$ | H | H | H | H | Allyl | Me | Me |
| A-9 | $Bu^t$ | H | H | H | H | Allyl | Me | Me |
| A-10 | OMe | H | H | H | H | Allyl | Me | Me |
| A-11 | OEt | H | H | H | H | Allyl | Me | Me |
| A-12 | $OPr^i$ | H | H | H | H | Allyl | Me | Me |
| A-13 | OPr | H | H | H | H | Allyl | Me | Me |
| A-14 | $OCHF_2$ | H | H | H | H | Allyl | Me | Me |
| A-15 | $OCF_3$ | H | H | H | H | Allyl | Me | Me |
| A-16 | $CF_3$ | H | H | H | H | Allyl | Me | Me |
| A-17 | SMe | H | H | H | H | Allyl | Me | Me |
| A-18 | SEt | H | H | H | H | Allyl | Me | Me |
| A-19 | $SPr^i$ | H | H | H | H | Allyl | Me | Me |
| A-20 | $NMe_2$ | H | H | H | H | Allyl | Me | Me |
| A-21 | $NEt_2$ | H | H | H | H | Allyl | Me | Me |
| A-22 | H | Cl | H | H | H | Allyl | Me | Me |
| A-23 | H | Br | H | H | H | Allyl | Me | Me |
| A-24 | H | Me | H | H | H | Allyl | Me | Me |
| A-25 | H | Et | H | H | H | Allyl | Me | Me |

TABLE 26

| | $R^1$ | $R^2$ | $R^3$ | $R^4$ | $R^5$ | $R^6$ | $R^7$ | $R^8$ |
|---|---|---|---|---|---|---|---|---|
| A-26 | H | Pr | H | H | H | Allyl | Me | Me |
| A-27 | H | $Pr^i$ | H | H | H | Allyl | Me | Me |
| A-28 | H | Bu | H | H | H | Allyl | Me | Me |
| A-29 | H | $Bu^i$ | H | H | H | Allyl | Me | Me |
| A-30 | H | $Bu^s$ | H | H | H | Allyl | Me | Me |
| A-31 | H | $Bu^t$ | H | H | H | Allyl | Me | Me |
| A-32 | H | OMe | H | H | H | Allyl | Me | Me |
| A-33 | H | OEt | H | H | H | Allyl | Me | Me |
| A-34 | H | OPr | H | H | H | Allyl | Me | Me |
| A-35 | H | $OPr^i$ | H | H | H | Allyl | Me | Me |
| A-36 | H | $OCHF_2$ | H | H | H | Allyl | Me | Me |
| A-37 | H | $OCF_3$ | H | H | H | Allyl | Me | Me |
| A-38 | H | $CF_3$ | H | H | H | Allyl | Me | Me |
| A-39 | H | SMe | H | H | H | Allyl | Me | Me |
| A-40 | H | SEt | H | H | H | Allyl | Me | Me |

TABLE 26-continued

| | $R^1$ | $R^2$ | $R^3$ | $R^4$ | $R^5$ | $R^6$ | $R^7$ | $R^8$ |
|---|---|---|---|---|---|---|---|---|
| A-41 | H | $SPr^i$ | H | H | H | Allyl | Me | Me |
| A-42 | H | $NMe_2$ | H | H | H | Allyl | Me | Me |
| A-43 | H | $NEt_2$ | H | H | H | Allyl | Me | Me |
| A-44 | H | H | Cl | H | H | Allyl | Me | Me |
| A-45 | H | H | Br | H | H | Allyl | Me | Me |
| A-46 | H | H | Me | H | H | Allyl | Me | Me |
| A-47 | H | H | Et | H | H | Allyl | Me | Me |
| A-48 | H | H | Pr | H | H | Allyl | Me | Me |
| A-49 | H | H | $Pr^i$ | H | H | Allyl | Me | Me |
| A-50 | H | H | Bu | H | H | Allyl | Me | Me |

TABLE 27

| | $R^1$ | $R^2$ | $R^3$ | $R^4$ | $R^5$ | $R^6$ | $R^7$ | $R^8$ |
|---|---|---|---|---|---|---|---|---|
| A-51 | H | H | $Bu^i$ | H | H | Allyl | Me | Me |
| A-52 | H | H | $Bu^s$ | H | H | Allyl | Me | Me |
| A-53 | H | H | $Bu^t$ | H | H | Allyl | Me | Me |
| A-54 | H | H | OMe | H | H | Allyl | Me | Me |
| A-55 | H | H | OEt | H | H | Allyl | Me | Me |
| A-56 | H | H | OPr | H | H | Allyl | Me | Me |
| A-57 | H | H | $OPr^i$ | H | H | Allyl | Me | Me |
| A-58 | H | H | $OCHF_2$ | H | H | Allyl | Me | Me |
| A-59 | H | H | $OCF_3$ | H | H | Allyl | Me | Me |
| A-60 | H | H | $CF_3$ | H | H | Allyl | Me | Me |
| A-61 | H | H | SMe | H | H | Allyl | Me | Me |
| A-62 | H | H | SEt | H | H | Allyl | Me | Me |
| A-63 | H | H | $SPr^i$ | H | H | Allyl | Me | Me |
| A-64 | H | H | $NMe_2$ | H | H | Allyl | Me | Me |
| A-65 | H | H | $NEt_2$ | H | H | Allyl | Me | Me |
| A-66 | Et | $NMe_2$ | H | H | H | Allyl | Me | Me |
| A-67 | $NMe_2$ | Cl | H | H | H | Allyl | Me | Me |
| A-68 | Et | $NEt_2$ | H | H | H | Allyl | Me | Me |
| A-69 | H | $NEt_2$ | Me | H | H | Allyl | Me | Me |
| A-70 | $Bu^s$ | H | H | H | H | Allyl | Me | Me |
| A-71 | OMe | H | OMe | H | H | Allyl | Me | Me |
| A-72 | H | OMe | OMe | H | H | Allyl | Me | Me |
| A-73 | H | OMe | OEt | H | H | Allyl | Me | Me |
| A-74 | H | OEt | OMe | H | H | Allyl | Me | Me |
| A-75 | OMe | H | Me | H | H | Allyl | Me | Me |
| A-76 | —$(CH_2)_3$— | | H | H | H | Allyl | Me | Me |
| A-77 | —$(CH_2)_4$— | | H | H | H | Allyl | Me | Me |

TABLE 28

| | R¹ | R² | R³ | R⁴ | R⁵ | R⁶ | R⁷ | R⁸ |
|---|---|---|---|---|---|---|---|---|
| B-1 | H | H | H | H | H | Allyl | Et | Et |
| B-2 | Cl | H | H | H | H | Allyl | Et | Et |
| B-3 | Br | H | H | H | H | Allyl | Et | Et |
| B-4 | Me | H | H | H | H | Allyl | Et | Et |
| B-5 | Et | H | H | H | H | Allyl | Et | Et |
| B-6 | Pr | H | H | H | H | Allyl | Et | Et |
| B-7 | Bu | H | H | H | H | Allyl | Et | Et |
| B-8 | Buⁱ | H | H | H | H | Allyl | Et | Et |
| B-9 | Buᵗ | H | H | H | H | Allyl | Et | Et |
| B-10 | OMe | H | Et | H | H | Allyl | Et | Et |
| B-11 | OEt | H | H | H | H | Allyl | Et | Et |
| B-12 | OPrⁱ | H | H | H | H | Allyl | Et | Et |
| B-13 | OPr | H | H | H | H | Allyl | Et | Et |
| B-14 | OCHF₂ | H | H | H | H | Allyl | Et | Et |
| B-15 | OCF₃ | H | H | H | H | Allyl | Et | Et |
| B-16 | CF₃ | H | H | H | H | Allyl | Et | Et |
| B-17 | SMe | H | H | H | H | Allyl | Et | Et |
| B-18 | SEt | H | H | H | H | Allyl | Et | Et |
| B-19 | SPrⁱ | H | H | H | H | Allyl | Et | Et |
| B-20 | OEt | H | Et | H | H | Allyl | Et | Et |
| B-21 | NEt₂ | H | H | H | H | Allyl | Et | Et |
| B-22 | H | Cl | H | H | H | Allyl | Et | Et |
| B-23 | H | Br | H | H | H | Allyl | Et | Et |
| B-24 | H | Me | H | H | H | Allyl | Et | Et |
| B-25 | H | Et | H | H | H | Allyl | Et | Et |

TABLE 29

| | R¹ | R² | R³ | R⁴ | R⁵ | R⁶ | R⁷ | R⁸ |
|---|---|---|---|---|---|---|---|---|
| B-26 | H | Pr | H | H | H | Allyl | Et | Et |
| B-27 | H | Prⁱ | H | H | H | Allyl | Et | Et |
| B-28 | H | Bu | H | H | H | Allyl | Et | Et |
| B-29 | H | Buⁱ | H | H | H | Allyl | Et | Et |
| B-30 | H | Buˢ | H | H | H | Allyl | Et | Et |
| B-31 | H | Buᵗ | H | H | H | Allyl | Et | Et |
| B-32 | H | OMe | H | H | H | Allyl | Et | Et |
| B-33 | H | OEt | H | H | H | Allyl | Et | Et |
| B-34 | H | OPr | H | H | H | Allyl | Et | Et |
| B-35 | H | OPrⁱ | H | H | H | Allyl | Et | Et |
| B-36 | H | OCHF₂ | H | H | H | Allyl | Et | Et |
| B-37 | H | OCF₃ | H | H | H | Allyl | Et | Et |
| B-38 | H | CF₃ | H | H | H | Allyl | Et | Et |
| B-39 | H | SMe | H | H | H | Allyl | Et | Et |
| B-40 | H | SEt | H | H | H | Allyl | Et | Et |
| B-41 | H | SPrⁱ | H | H | H | Allyl | Et | Et |
| B-42 | H | NMe₂ | H | H | H | Allyl | Et | Et |
| B-43 | H | NEt₂ | H | H | H | Allyl | Et | Et |
| B-44 | H | H | Cl | H | H | Allyl | Et | Et |
| B-45 | H | H | Br | H | H | Allyl | Et | Et |
| B-46 | H | H | Me | H | H | Allyl | Et | Et |
| B-47 | H | H | CH₂OMe | H | H | Allyl | Et | Et |
| B-48 | H | H | Pr | H | H | Allyl | Et | Et |
| B-49 | MeO | H | Me | H | H | Allyl | Et | Et |
| B-50 | H | H | Bu | H | H | Allyl | Et | Et |

TABLE 30

| | R¹ | R² | R³ | R⁴ | R⁵ | R⁶ | R⁷ | R⁸ |
|---|---|---|---|---|---|---|---|---|
| B-51 | H | H | Buⁱ | H | H | Allyl | Et | Et |
| B-52 | H | H | Buˢ | H | H | Allyl | Et | Et |
| B-53 | H | H | Buᵗ | H | H | Allyl | Et | Et |
| B-54 | H | H | OMe | H | H | Allyl | Et | Et |
| B-55 | H | H | OEt | H | H | Allyl | Et | Et |
| B-56 | H | H | OPr | H | H | Allyl | Et | Et |
| B-57 | H | H | OPrⁱ | H | H | Allyl | Et | Et |
| B-58 | H | H | OCHF₂ | H | H | Allyl | Et | Et |
| B-59 | H | H | OCF₃ | H | H | Allyl | Et | Et |
| B-60 | H | H | CF₃ | H | H | Allyl | Et | Et |
| B-61 | H | H | SMe | H | H | Allyl | Et | Et |
| B-62 | H | H | SEt | H | H | Allyl | Et | Et |
| B-63 | H | H | SPrⁱ | H | H | Allyl | Et | Et |
| B-64 | H | H | NMe₂ | H | H | Allyl | Et | Et |
| B-65 | H | H | NEt₂ | H | H | Allyl | Et | Et |
| B-66 | Et | NMe₂ | H | H | H | Allyl | Et | Et |
| B-67 | NMe₂ | Cl | H | H | H | Allyl | Et | Et |
| B-68 | Et | NEt₂ | H | H | H | Allyl | Et | Et |
| B-69 | H | NEt₂ | Me | H | H | Allyl | Et | Et |
| B-70 | Me | NEt₂ | H | H | H | Allyl | Et | Et |
| B-71 | OMe | H | OMe | H | H | Allyl | Et | Et |
| B-72 | H | OMe | OMe | H | H | Allyl | Et | Et |
| B-73 | OMe | H | Et | H | H | Allyl | Et | Et |
| B-74 | H | OEt | OMe | H | H | Allyl | Et | Et |
| B-75 | —(CH₂)₃— | | H | H | H | Allyl | Et | Et |
| B-76 | —(CH₂)₄— | | H | H | H | Allyl | Et | Et |

TABLE 31

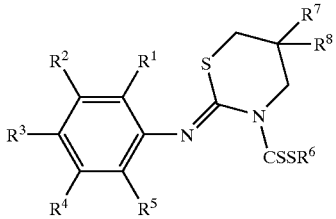

| | R¹ | R² | R³ | R⁴ | R⁵ | R⁶ | R⁷ | R⁸ |
|---|---|---|---|---|---|---|---|---|
| C-1 | H | H | H | H | H | Allyl | —(CH₂)₂— | |
| C-2 | Cl | H | H | H | H | Allyl | —(CH₂)₂— | |
| C-3 | Br | H | H | H | H | Allyl | —(CH₂)₂— | |
| C-4 | Me | H | H | H | H | Allyl | —(CH₂)₂— | |
| C-5 | Et | H | H | H | H | Allyl | —(CH₂)₂— | |
| C-6 | Pr | H | H | H | H | Allyl | —(CH₂)₂— | |
| C-7 | Bu | H | H | H | H | Allyl | —(CH₂)₂— | |
| C-8 | Buⁱ | H | H | H | H | Allyl | —(CH₂)₂— | |
| C-9 | Buᵗ | H | H | H | H | Allyl | —(CH₂)₂— | |
| C-10 | OMe | H | H | H | H | Allyl | —(CH₂)₂— | |
| C-11 | OEt | H | H | H | H | Allyl | —(CH₂)₂— | |
| C-12 | OPrⁱ | H | H | H | H | Allyl | —(CH₂)₂— | |
| C-13 | OPr | H | H | H | H | Allyl | —(CH₂)₂— | |
| C-14 | OCHF₂ | H | H | H | H | Allyl | —(CH₂)₂— | |
| C-15 | OCF₃ | H | H | H | H | Allyl | —(CH₂)₂— | |
| C-16 | CF₃ | H | H | H | H | Allyl | —(CH₂)₂— | |
| C-17 | SMe | H | H | H | H | Allyl | —(CH₂)₂— | |
| C-18 | SEt | H | H | H | H | Allyl | —(CH₂)₂— | |
| C-19 | SPrⁱ | H | H | H | H | Allyl | —(CH₂)₂— | |
| C-20 | NMe₂ | H | H | H | H | Allyl | —(CH₂)₂— | |
| C-21 | NEt₂ | H | H | H | H | Allyl | —(CH₂)₂— | |
| C-22 | H | Cl | H | H | H | Allyl | —(CH₂)₂— | |
| C-23 | H | Br | H | H | H | Allyl | —(CH₂)₂— | |
| C-24 | H | Me | H | H | H | Allyl | —(CH₂)₂— | |
| C-25 | H | Et | H | H | H | Allyl | —(CH₂)₂— | |

TABLE 32

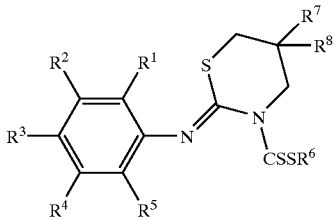

| | R¹ | R² | R³ | R⁴ | R⁵ | R⁶ | R⁷ | R⁸ |
|---|---|---|---|---|---|---|---|---|
| C-26 | H | Pr | H | H | H | Allyl | —(CH₂)₂— | |
| C-27 | H | Prⁱ | H | H | H | Allyl | —(CH₂)₂— | |
| C-28 | H | Bu | H | H | H | Allyl | —(CH₂)₂— | |
| C-29 | H | Buⁱ | H | H | H | Allyl | —(CH₂)₂— | |
| C-30 | H | Buˢ | H | H | H | Allyl | —(CH₂)₂— | |
| C-31 | H | Buᵗ | H | H | H | Allyl | —(CH₂)₂— | |
| C-32 | H | OMe | H | H | H | Allyl | —(CH₂)₂— | |
| C-33 | H | OEt | H | H | H | Allyl | —(CH₂)₂— | |
| C-34 | H | OPr | H | H | H | Allyl | —(CH₂)₂— | |
| C-35 | H | OPrⁱ | H | H | H | Allyl | —(CH₂)₂— | |
| C-36 | H | OCHF₂ | H | H | H | Allyl | —(CH₂)₂— | |
| C-37 | H | OCF₃ | H | H | H | Allyl | —(CH₂)₂— | |
| C-38 | H | CF₃ | H | H | H | Allyl | —(CH₂)₂— | |
| C-39 | H | SMe | H | H | H | Allyl | —(CH₂)₂— | |
| C-40 | H | SEt | H | H | H | Allyl | —(CH₂)₂— | |
| C-41 | H | SPrⁱ | H | H | H | Allyl | —(CH₂)₂— | |
| C-42 | H | NMe₂ | H | H | H | Allyl | —(CH₂)₂— | |
| C-43 | H | NEt₂ | H | H | H | Allyl | —(CH₂)₂— | |
| C-44 | H | H | Cl | H | H | Allyl | —(CH₂)₂— | |
| C-45 | H | H | Br | H | H | Allyl | —(CH₂)₂— | |
| C-46 | H | H | Me | H | H | Allyl | —(CH₂)₂— | |
| C-47 | H | H | Et | H | H | Allyl | —(CH₂)₂— | |

TABLE 32-continued

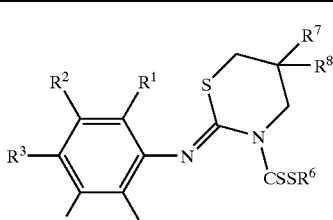

| | R¹ | R² | R³ | R⁴ | R⁵ | R⁶ | R⁷ | R⁸ |
|---|---|---|---|---|---|---|---|---|
| C-48 | H | H | Pr | H | H | Allyl | —(CH₂)₂— | |
| C-49 | H | H | Prⁱ | H | H | Allyl | —(CH₂)₂— | |
| C-50 | H | H | Bu | H | H | Allyl | —(CH₂)₂— | |

TABLE 33

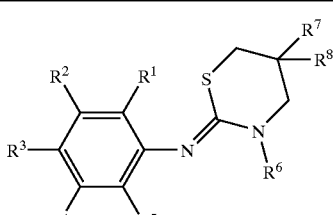

| | R¹ | R² | R³ | R⁴ | R⁵ | R⁶ | R⁷ | R⁸ |
|---|---|---|---|---|---|---|---|---|
| C-51 | H | H | Buⁱ | H | H | Allyl | —(CH₂)₂— | |
| C-52 | H | H | Buˢ | H | H | Allyl | —(CH₂)₂— | |
| C-53 | H | H | Buᵗ | H | H | Allyl | —(CH₂)₂— | |
| C-54 | H | H | OMe | H | H | Allyl | —(CH₂)₂— | |
| C-55 | H | H | OEt | H | H | Allyl | —(CH₂)₂— | |
| C-56 | H | H | OPr | H | H | Allyl | —(CH₂)₂— | |
| C-57 | H | H | OPrⁱ | H | H | Allyl | —(CH₂)₂— | |
| C-58 | H | H | OCHF₂ | H | H | Allyl | —(CH₂)₂— | |
| C-59 | H | H | OCF₃ | H | H | Allyl | —(CH₂)₂— | |
| C-60 | H | H | CF₃ | H | H | Allyl | —(CH₂)₂— | |
| C-61 | H | H | SMe | H | H | Allyl | —(CH₂)₂— | |
| C-62 | H | H | SEt | H | H | Allyl | —(CH₂)₂— | |
| C-63 | H | H | SPrⁱ | H | H | Allyl | —(CH₂)₂— | |
| C-64 | H | H | NMe₂ | H | H | Allyl | —(CH₂)₂— | |
| C-65 | H | H | NEt₂ | H | H | Allyl | —(CH₂)₂— | |
| C-66 | Me | NMe₂ | H | H | H | Allyl | —(CH₂)₂— | |
| C-67 | NMe₂ | Cl | H | H | H | Allyl | —(CH₂)₂— | |
| C-68 | Me | NEt₂ | H | H | H | Allyl | —(CH₂)₂— | |
| C-69 | H | NEt₂ | Me | H | H | Allyl | —(CH₂)₂— | |
| C-70 | Buˢ | H | H | H | H | Allyl | —(CH₂)₂— | |
| C-71 | Prⁱ | H | H | H | H | Allyl | —(CH₂)₂— | |
| C-72 | H | OMe | OMe | H | H | Allyl | —(CH₂)₂— | |
| C-73 | H | OMe | OEt | H | H | Allyl | —(CH₂)₂— | |
| C-74 | H | OEt | OMe | H | H | Allyl | —(CH₂)₂— | |
| C-75 | H | OEt | OEt | H | H | Allyl | —(CH₂)₂— | |
| C-76 | OMe | H | Me | H | H | Allyl | —(CH₂)₂— | |
| C-77 | OMe | H | Et | H | H | Allyl | —(CH₂)₂— | |
| C-78 | —(CH₂)₃— | | H | H | H | Allyl | —(CH₂)₂— | |
| C-79 | —(CH₂)₄— | | H | H | H | Allyl | —(CH₂)₂— | |

TABLE 34

[Structure: phenyl ring with R1-R5 substituents, connected via N=C to a thiazine ring bearing S, CSSR6 on N, and R7, R8 substituents]

| | R¹ | R² | R³ | R⁴ | R⁵ | R⁶ | R⁷ | R⁸ |
|---|---|---|---|---|---|---|---|---|
| D-1 | H | H | H | H | H | Allyl | —(CH₂)₄— | |
| D-2 | Cl | H | H | H | H | Allyl | —(CH₂)₄— | |
| D-3 | Br | H | H | H | H | Allyl | —(CH₂)₄— | |
| D-4 | Me | H | H | H | H | Allyl | —(CH₂)₄— | |
| D-5 | Et | H | H | H | H | Allyl | —(CH₂)₄— | |
| D-6 | Pr | H | H | H | H | Allyl | —(CH₂)₄— | |
| D-7 | Bu | H | H | H | H | Allyl | —(CH₂)₄— | |
| D-8 | Buⁱ | H | H | H | H | Allyl | —(CH₂)₄— | |
| D-9 | Buᵗ | H | H | H | H | Allyl | —(CH₂)₄— | |
| D-10 | OMe | H | Et | H | H | Allyl | —(CH₂)₄— | |
| D-11 | OEt | H | H | H | H | Allyl | —(CH₂)₄— | |
| D-12 | OPrⁱ | H | H | H | H | Allyl | —(CH₂)₄— | |
| D-13 | OPr | H | H | H | H | Allyl | —(CH₂)₄— | |
| D-14 | OCHF₂ | H | H | H | H | Allyl | —(CH₂)₄— | |
| D-15 | OCF₃ | H | H | H | H | Allyl | —(CH₂)₄— | |
| D-16 | CF₃ | H | H | H | H | Allyl | —(CH₂)₄— | |
| D-17 | SMe | H | H | H | H | Allyl | —(CH₂)₄— | |
| D-18 | SEt | H | H | H | H | Allyl | —(CH₂)₄— | |
| D-19 | SPrⁱ | H | H | H | H | Allyl | —(CH₂)₄— | |
| D-20 | OEt | H | Et | H | H | Allyl | —(CH₂)₄— | |
| D-21 | NEt₂ | H | H | H | H | Allyl | —(CH₂)₄— | |
| D-22 | H | Cl | H | H | H | Allyl | —(CH₂)₄— | |
| D-23 | H | Br | H | H | H | Allyl | —(CH₂)₄— | |
| D-24 | H | Me | H | H | H | Allyl | —(CH₂)₄— | |
| D-25 | H | Et | H | H | H | Allyl | —(CH₂)₄— | |

TABLE 35

[Structure as above]

| | R¹ | R² | R³ | R⁴ | R⁵ | R⁶ | R⁷ | R⁸ |
|---|---|---|---|---|---|---|---|---|
| D-26 | H | Pr | H | H | H | Allyl | —(CH₂)₄— | |
| D-27 | H | Prⁱ | H | H | H | Allyl | —(CH₂)₄— | |
| D-28 | H | Bu | H | H | H | Allyl | —(CH₂)₄— | |
| D-29 | H | Buⁱ | H | H | H | Allyl | —(CH₂)₄— | |
| D-30 | H | Buˢ | H | H | H | Allyl | —(CH₂)₄— | |
| D-31 | H | Buᵗ | H | H | H | Allyl | —(CH₂)₄— | |
| D-32 | H | OMe | H | H | H | Allyl | —(CH₂)₄— | |
| D-33 | H | OEt | H | H | H | Allyl | —(CH₂)₄— | |
| D-34 | H | OPr | H | H | H | Allyl | —(CH₂)₄— | |
| D-35 | H | OPrⁱ | H | H | H | Allyl | —(CH₂)₄— | |
| D-36 | H | OCHF₂ | H | H | H | Allyl | —(CH₂)₄— | |
| D-37 | H | OCF₃ | H | H | H | Allyl | —(CH₂)₄— | |
| D-38 | H | CF₃ | H | H | H | Allyl | —(CH₂)₄— | |
| D-39 | OMe | H | Me | H | H | Allyl | —(CH₂)₄— | |
| D-40 | H | SEt | H | H | H | Allyl | —(CH₂)₄— | |
| D-41 | H | SPrⁱ | H | H | H | Allyl | —(CH₂)₄— | |
| D-42 | H | NMe₂ | H | H | H | Allyl | —(CH₂)₄— | |
| D-43 | H | NEt₂ | H | H | H | Allyl | —(CH₂)₄— | |
| D-44 | H | H | Cl | H | H | Allyl | —(CH₂)₄— | |
| D-45 | H | H | Br | H | H | Allyl | —(CH₂)₄— | |
| D-46 | H | H | Me | H | H | Allyl | —(CH₂)₄— | |
| D-47 | H | OMe | Et | H | H | Allyl | —(CH₂)₄— | |

TABLE 35-continued

[Structure as above]

| | R¹ | R² | R³ | R⁴ | R⁵ | R⁶ | R⁷ | R⁸ |
|---|---|---|---|---|---|---|---|---|
| D-48 | H | H | Pr | H | H | Allyl | —(CH₂)₄— | |
| D-49 | H | H | Prⁱ | H | H | Allyl | —(CH₂)₄— | |
| D-50 | H | H | Bu | H | H | Allyl | —(CH₂)₄— | |

TABLE 36

[Structure as above]

| | R¹ | R² | R³ | R⁴ | R⁵ | R⁶ | R⁷ | R⁸ |
|---|---|---|---|---|---|---|---|---|
| D-51 | H | H | Buⁱ | H | H | Allyl | —(CH₂)₄— | |
| D-52 | H | H | Buˢ | H | H | Allyl | —(CH₂)₄— | |
| D-53 | H | H | Buᵗ | H | H | Allyl | —(CH₂)₄— | |
| D-54 | H | H | OMe | H | H | Allyl | —(CH₂)₄— | |
| D-55 | H | H | OEt | H | H | Allyl | —(CH₂)₄— | |
| D-56 | H | H | OPr | H | H | Allyl | —(CH₂)₄— | |
| D-57 | H | H | OPrⁱ | H | H | Allyl | —(CH₂)₄— | |
| D-58 | H | H | OCHF₂ | H | H | Allyl | —(CH₂)₄— | |
| D-59 | Et | NMe₂ | H | H | H | Allyl | —(CH₂)₄— | |
| D-60 | H | H | CF₃ | H | H | Allyl | —(CH₂)₄— | |
| D-61 | MeO | H | Et | H | H | Allyl | —(CH₂)₄— | |
| D-62 | H | H | SEt | H | H | Allyl | —(CH₂)₄— | |
| D-63 | H | H | SPrⁱ | H | H | Allyl | —(CH₂)₄— | |
| D-64 | H | H | NMe₂ | H | H | Allyl | —(CH₂)₄— | |
| D-65 | H | H | NEt₂ | H | H | Allyl | —(CH₂)₄— | |
| D-66 | Me | NMe₂ | H | H | H | Allyl | —(CH₂)₄— | |
| D-67 | NMe₂ | Cl | H | H | H | Allyl | —(CH₂)₄— | |
| D-68 | Me | NEt₂ | H | H | H | Allyl | —(CH₂)₄— | |
| D-69 | H | NEt₂ | Me | H | H | Allyl | —(CH₂)₄— | |
| D-70 | Buˢ | H | H | H | H | Allyl | —(CH₂)₄— | |
| D-71 | Et | NEt₂ | H | H | H | Allyl | —(CH₂)₄— | |
| D-72 | H | OMe | OMe | H | H | Allyl | —(CH₂)₄— | |
| D-73 | H | OMe | OEt | H | H | Allyl | —(CH₂)₄— | |
| D-74 | H | OEt | OMe | H | H | Allyl | —(CH₂)₄— | |
| D-75 | H | OEt | OEt | H | H | Allyl | —(CH₂)₄— | |
| D-76 | —(CH₂)₃— | | H | H | H | Allyl | —(CH₂)₄— | |
| D-77 | —(CH₂)₂— | | H | H | H | Allyl | —(CH₂)₄— | |

TABLE 37

| | R¹ | R² | R³ | R⁴ | R⁵ | R⁶ | R⁷ | R⁸ |
|---|---|---|---|---|---|---|---|---|
| E-1 | H | H | H | H | H | Allyl | —(CH$_2$)$_5$— | |
| E-2 | Cl | H | H | H | H | Allyl | —(CH$_2$)$_5$— | |
| E-3 | Br | H | H | H | H | Allyl | —(CH$_2$)$_5$— | |
| E-4 | Me | H | H | H | H | Allyl | —(CH$_2$)$_5$— | |
| E-5 | Et | H | H | H | H | Allyl | —(CH$_2$)$_5$— | |
| E-6 | Pr | H | H | H | H | Allyl | —(CH$_2$)$_5$— | |
| E-7 | Bu | H | H | H | H | Allyl | —(CH$_2$)$_5$— | |
| E-8 | Bu$^i$ | H | H | H | H | Allyl | —(CH$_2$)$_5$— | |
| E-9 | Bu$^t$ | H | H | H | H | Allyl | —(CH$_2$)$_5$— | |
| E-10 | OMe | H | Et | H | H | Allyl | —(CH$_2$)$_5$— | |
| E-11 | OEt | H | H | H | H | Allyl | —(CH$_2$)$_5$— | |
| E-12 | OPr$^i$ | H | H | H | H | Allyl | —(CH$_2$)$_5$— | |
| E-13 | OPr | H | H | H | H | Allyl | —(CH$_2$)$_5$— | |
| E-14 | OCHF$_2$ | H | H | H | H | Allyl | —(CH$_2$)$_5$— | |
| E-15 | OCF$_3$ | H | H | H | H | Allyl | —(CH$_2$)$_5$— | |
| E-16 | CF$_3$ | H | H | H | H | Allyl | —(CH$_2$)$_5$— | |
| E-17 | SMe | H | H | H | H | Allyl | —(CH$_2$)$_5$— | |
| E-18 | SEt | H | H | H | H | Allyl | —(CH$_2$)$_5$— | |
| E-19 | SPr$^i$ | H | H | H | H | Allyl | —(CH$_2$)$_5$— | |
| E-20 | OEt | H | Et | H | H | Allyl | —(CH$_2$)$_5$— | |
| E-21 | NEt$_2$ | H | H | H | H | Allyl | —(CH$_2$)$_5$— | |
| E-22 | H | Cl | H | H | H | Allyl | —(CH$_2$)$_5$— | |
| E-23 | H | Br | H | H | H | Allyl | —(CH$_2$)$_5$— | |
| E-24 | H | Me | H | H | H | Allyl | —(CH$_2$)$_5$— | |
| E-25 | H | Et | H | H | H | Allyl | —(CH$_2$)$_5$— | |

TABLE 38

| | R¹ | R² | R³ | R⁴ | R⁵ | R⁶ | R⁷ | R⁸ |
|---|---|---|---|---|---|---|---|---|
| E-26 | H | Pr | H | H | H | Allyl | —(CH$_2$)$_5$— | |
| E-27 | H | Pr$^i$ | H | H | H | Allyl | —(CH$_2$)$_5$— | |
| E-28 | H | Bu | H | H | H | Allyl | —(CH$_2$)$_5$— | |
| E-29 | H | Bu$^i$ | H | H | H | Allyl | —(CH$_2$)$_5$— | |
| E-30 | H | Bu$^s$ | H | H | H | Allyl | —(CH$_2$)$_5$— | |
| E-31 | H | Bu$^t$ | H | H | H | Allyl | —(CH$_2$)$_5$— | |
| E-32 | H | OMe | H | H | H | Allyl | —(CH$_2$)$_5$— | |
| E-33 | H | OEt | H | H | H | Allyl | —(CH$_2$)$_5$— | |
| E-34 | H | OPr | H | H | H | Allyl | —(CH$_2$)$_5$— | |
| E-35 | H | OPr$^i$ | H | H | H | Allyl | —(CH$_2$)$_5$— | |
| E-36 | H | OCHF$_2$ | H | H | H | Allyl | —(CH$_2$)$_5$— | |
| E-37 | H | OCF$_3$ | H | H | H | Allyl | —(CH$_2$)$_5$— | |
| E-38 | H | CF$_3$ | H | H | H | Allyl | —(CH$_2$)$_5$— | |
| E-39 | OMe | H | Me | H | H | Allyl | —(CH$_2$)$_5$— | |
| E-40 | H | SEt | H | H | H | Allyl | —(CH$_2$)$_5$— | |
| E-41 | H | SPr$^i$ | H | H | H | Allyl | —(CH$_2$)$_5$— | |
| E-42 | H | NMe$_2$ | H | H | H | Allyl | —(CH$_2$)$_5$— | |
| E-43 | H | NEt$_2$ | H | H | H | Allyl | —(CH$_2$)$_5$— | |
| E-44 | H | H | Cl | H | H | Allyl | —(CH$_2$)$_5$— | |
| E-45 | H | H | Br | H | H | Allyl | —(CH$_2$)$_5$— | |
| E-46 | H | H | Me | H | H | Allyl | —(CH$_2$)$_5$— | |
| E-47 | H | OMe | Et | H | H | Allyl | —(CH$_2$)$_5$— | |
| E-48 | H | H | Pr | H | H | Allyl | —(CH$_2$)$_5$— | |
| E-49 | H | H | Pr$^i$ | H | H | Allyl | —(CH$_2$)$_5$— | |
| E-50 | H | H | Bu | H | H | Allyl | —(CH$_2$)$_5$— | |

TABLE 39

| | R¹ | R² | R³ | R⁴ | R⁵ | R⁶ | R⁷ | R⁸ |
|---|---|---|---|---|---|---|---|---|
| E-51 | H | H | Bu$^i$ | H | H | Allyl | —(CH$_2$)$_5$— | |
| E-52 | H | H | Bu$^s$ | H | H | Allyl | —(CH$_2$)$_5$— | |
| E-53 | H | H | Bu$^t$ | H | H | Allyl | —(CH$_2$)$_5$— | |
| E-54 | H | H | OMe | H | H | Allyl | —(CH$_2$)$_5$— | |
| E-55 | H | H | OEt | H | H | Allyl | —(CH$_2$)$_5$— | |
| E-56 | H | H | OPr | H | H | Allyl | —(CH$_2$)$_5$— | |
| E-57 | H | H | OPr$^i$ | H | H | Allyl | —(CH$_2$)$_5$— | |
| E-58 | H | H | OCHF$_2$ | H | H | Allyl | —(CH$_2$)$_5$— | |
| E-59 | Et | NMe$_2$ | H | H | H | Allyl | —(CH$_2$)$_5$— | |
| E-60 | H | H | CF$_3$ | H | H | Allyl | —(CH$_2$)$_5$— | |
| E-61 | MeO | H | Et | H | H | Allyl | —(CH$_2$)$_5$— | |
| E-62 | H | H | SEt | H | H | Allyl | —(CH$_2$)$_5$— | |
| E-63 | H | H | SPr$^i$ | H | H | Allyl | —(CH$_2$)$_5$— | |
| E-64 | H | H | NMe$_2$ | H | H | Allyl | —(CH$_2$)$_5$— | |
| E-65 | H | H | NEt$_2$ | H | H | Allyl | —(CH$_2$)$_5$— | |
| E-66 | Me | NMe$_2$ | H | H | H | Allyl | —(CH$_2$)$_5$— | |
| E-67 | NMe$_2$ | Cl | H | H | H | Allyl | —(CH$_2$)$_5$— | |
| E-68 | Me | NEt$_2$ | H | H | H | Allyl | —(CH$_2$)$_5$— | |
| E-69 | H | NEt$_2$ | Me | H | H | Allyl | —(CH$_2$)$_5$— | |
| E-70 | Bu$^s$ | H | H | H | H | Allyl | —(CH$_2$)$_5$— | |
| E-71 | Et | NEt$_2$ | H | H | H | Allyl | —(CH$_2$)$_5$— | |
| E-72 | H | OMe | OMe | H | H | Allyl | —(CH$_2$)$_5$— | |
| E-73 | H | OMe | OEt | H | H | Allyl | —(CH$_2$)$_5$— | |
| E-74 | H | OEt | OMe | H | H | Allyl | —(CH$_2$)$_5$— | |
| E-75 | H | OEt | OEt | H | H | Allyl | —(CH$_2$)$_5$— | |
| E-76 | —(CH$_2$)$_3$— | | H | H | H | Allyl | —(CH$_2$)$_5$— | |
| E-77 | —(CH$_2$)$_4$— | | H | H | H | Allyl | —(CH$_2$)$_5$— | |

TABLE 40

| | R¹ | R² | R³ | R⁴ | R⁵ | R⁶ | R⁷ | R⁸ |
|---|---|---|---|---|---|---|---|---|
| F-1 | H | H | H | H | H | Allyl | —(CH$_2$)$_2$O(CH$_2$)$_2$— | |
| F-2 | Cl | H | H | H | H | Allyl | —(CH$_2$)$_2$O(CH$_2$)$_2$— | |

TABLE 40-continued

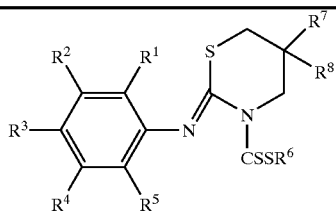

| | $R^1$ | $R^2$ | $R^3$ | $R^4$ | $R^5$ | $R^6$ | $R^7$ | $R^8$ |
|---|---|---|---|---|---|---|---|---|
| F-3 | Br | H | H | H | H | Allyl | —$(CH_2)_2O(CH_2)_2$— | |
| F-4 | Me | H | H | H | H | Allyl | —$(CH_2)_2O(CH_2)_2$— | |
| F-5 | Et | H | H | H | H | Allyl | —$(CH_2)_2O(CH_2)_2$— | |
| F-6 | Pr | H | H | H | H | Allyl | —$(CH_2)_2O(CH_2)_2$— | |
| F-7 | Bu | H | H | H | H | Allyl | —$(CH_2)_2O(CH_2)_2$— | |
| F-8 | $Bu^i$ | H | H | H | H | Allyl | —$(CH_2)_2O(CH_2)_2$— | |
| F-9 | $Bu^t$ | H | H | H | H | Allyl | —$(CH_2)_2O(CH_2)_2$— | |
| F-10 | OMe | H | H | H | H | Allyl | —$(CH_2)_2O(CH_2)_2$— | |
| F-11 | OEt | H | H | H | H | Allyl | —$(CH_2)_2O(CH_2)_2$— | |
| F-12 | $OPr^i$ | H | H | H | H | Allyl | —$(CH_2)_2O(CH_2)_2$— | |
| F-13 | OPr | H | H | H | H | Allyl | —$(CH_2)_2O(CH_2)_2$— | |
| F-14 | $OCHF_2$ | H | H | H | H | Allyl | —$(CH_2)_2O(CH_2)_2$— | |
| F-15 | $OCF_3$ | H | H | H | H | Allyl | —$(CH_2)_2O(CH_2)_2$— | |
| F-16 | $CF_3$ | H | H | H | H | Allyl | —$(CH_2)_2O(CH_2)_2$— | |
| F-17 | SMe | H | H | H | H | Allyl | —$(CH_2)_2O(CH_2)_2$— | |
| F-18 | SEt | H | H | H | H | Allyl | —$(CH_2)_2O(CH_2)_2$— | |
| F-19 | $SPr^i$ | H | H | H | H | Allyl | —$(CH_2)_2O(CH_2)_2$— | |
| F-20 | $NMe_2$ | H | H | H | H | Allyl | —$(CH_2)_2O(CH_2)_2$— | |
| F-21 | $NEt_2$ | H | H | H | H | Allyl | —$(CH_2)_2O(CH_2)_2$— | |
| F-22 | H | Cl | H | H | H | Allyl | —$(CH_2)_2O(CH_2)_2$— | |
| F-23 | H | Br | H | H | H | Allyl | —$(CH_2)_2O(CH_2)_2$— | |
| F-24 | H | Me | H | H | H | Allyl | —$(CH_2)_2O(CH_2)_2$— | |
| F-25 | H | Et | H | H | H | Allyl | —$(CH_2)_2O(CH_2)_2$— | |

TABLE 41

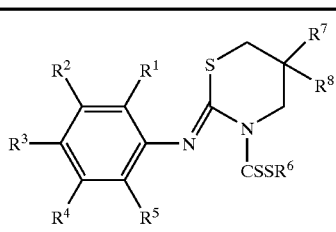

| | $R^1$ | $R^2$ | $R^3$ | $R^4$ | $R^5$ | $R^6$ | $R^7$ | $R^8$ |
|---|---|---|---|---|---|---|---|---|
| F-26 | H | Pr | H | H | H | Allyl | —$(CH_2)_2O(CH_2)_2$— | |
| F-27 | H | $Pr^i$ | H | H | H | Allyl | —$(CH_2)_2O(CH_2)_2$— | |
| F-28 | H | Bu | H | H | H | Allyl | —$(CH_2)_2O(CH_2)_2$— | |
| F-29 | H | $Bu^i$ | H | H | H | Allyl | —$(CH_2)_2O(CH_2)_2$— | |
| F-30 | H | $Bu^s$ | H | H | H | Allyl | —$(CH_2)_2O(CH_2)_2$— | |
| F-31 | H | $Bu^t$ | H | H | H | Allyl | —$(CH_2)_2O(CH_2)_2$— | |
| F-32 | H | OMe | H | H | H | Allyl | —$(CH_2)_2O(CH_2)_2$— | |
| F-33 | H | OEt | H | H | H | Allyl | —$(CH_2)_2O(CH_2)_2$— | |
| F-34 | H | OPr | H | H | H | Allyl | —$(CH_2)_2O(CH_2)_2$— | |
| F-35 | H | $OPr^i$ | H | H | H | Allyl | —$(CH_2)_2O(CH_2)_2$— | |
| F-36 | H | $OCHF_2$ | H | H | H | Allyl | —$(CH_2)_2O(CH_2)_2$— | |
| F-37 | H | $OCF_3$ | H | H | H | Allyl | —$(CH_2)_2O(CH_2)_2$— | |
| F-38 | H | $CF_3$ | H | H | H | Allyl | —$(CH_2)_2O(CH_2)_2$— | |
| F-39 | H | SMe | H | H | H | Allyl | —$(CH_2)_2O(CH_2)_2$— | |
| F-40 | H | SEt | H | H | H | Allyl | —$(CH_2)_2O(CH_2)_2$— | |
| F-41 | H | $SPr^i$ | H | H | H | Allyl | —$(CH_2)_2O(CH_2)_2$— | |
| F-42 | H | $NMe_2$ | H | H | H | Allyl | —$(CH_2)_2O(CH_2)_2$— | |
| F-43 | H | $NEt_2$ | H | H | H | Allyl | —$(CH_2)_2O(CH_2)_2$— | |
| F-44 | H | H | Cl | H | H | Allyl | —$(CH_2)_2O(CH_2)_2$— | |
| F-45 | H | H | Br | H | H | Allyl | —$(CH_2)_2O(CH_2)_2$— | |
| F-46 | H | H | Me | H | H | Allyl | —$(CH_2)_2O(CH_2)_2$— | |
| F-47 | H | H | Et | H | H | Allyl | —$(CH_2)_2O(CH_2)_2$— | |
| F-48 | H | H | Pr | H | H | Allyl | —$(CH_2)_2O(CH_2)_2$— | |

TABLE 41-continued

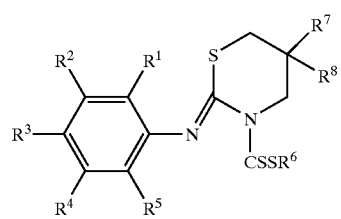

| | $R^1$ | $R^2$ | $R^3$ | $R^4$ | $R^5$ | $R^6$ | $R^7$ | $R^8$ |
|---|---|---|---|---|---|---|---|---|
| F-49 | H | H | $Pr^i$ | H | H | Allyl | —$(CH_2)_2O(CH_2)_2$— | |
| F-50 | H | H | Bu | H | H | Allyl | —$(CH_2)_2O(CH_2)_2$— | |

TABLE 42

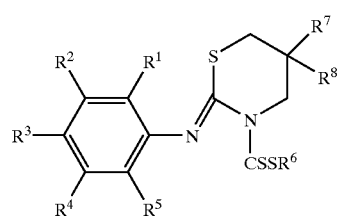

| | $R^1$ | $R^2$ | $R^3$ | $R^4$ | $R^5$ | $R^6$ | $R^7$ | $R^8$ |
|---|---|---|---|---|---|---|---|---|
| F-51 | H | H | $Bu^i$ | H | H | Allyl | —$(CH_2)_2O(CH_2)_2$— | |
| F-52 | H | H | $Bu^s$ | H | H | Allyl | —$(CH_2)_2O(CH_2)_2$— | |
| F-53 | H | H | $Bu^t$ | H | H | Allyl | —$(CH_2)_2O(CH_2)_2$— | |
| F-54 | H | H | OMe | H | H | Allyl | —$(CH_2)_2O(CH_2)_2$— | |
| F-55 | H | H | OEt | H | H | Allyl | —$(CH_2)_2O(CH_2)_2$— | |
| F-56 | H | H | OPr | H | H | Allyl | —$(CH_2)_2O(CH_2)_2$— | |
| F-57 | H | H | $OPr^i$ | H | H | Allyl | —$(CH_2)_2O(CH_2)_2$— | |
| F-58 | H | H | $OCHF_2$ | H | H | Allyl | —$(CH_2)_2O(CH_2)_2$— | |
| F-59 | H | H | $OCF_3$ | H | H | Allyl | —$(CH_2)_2O(CH_2)_2$— | |
| F-60 | H | H | $CF_3$ | H | H | Allyl | —$(CH_2)_2O(CH_2)_2$— | |
| F-61 | H | H | SMe | H | H | Allyl | —$(CH_2)_2O(CH_2)_2$— | |
| F-62 | H | H | SEt | H | H | Allyl | —$(CH_2)_2O(CH_2)_2$— | |
| F-63 | H | H | $SPr^i$ | H | H | Allyl | —$(CH_2)_2O(CH_2)_2$— | |
| F-64 | H | H | $NMe_2$ | H | H | Allyl | —$(CH_2)_2O(CH_2)_2$— | |
| F-65 | H | H | $NEt_2$ | H | H | Allyl | —$(CH_2)_2O(CH_2)_2$— | |
| F-66 | Me | $NMe_2$ | H | H | H | Allyl | —$(CH_2)_2O(CH_2)_2$— | |
| F-67 | $NMe_2$ | Cl | H | H | H | Allyl | —$(CH_2)_2O(CH_2)_2$— | |
| F-68 | Me | $NEt_2$ | H | H | H | Allyl | —$(CH_2)_2O(CH_2)_2$— | |
| F-69 | H | $NEt_2$ | Me | H | H | Allyl | —$(CH_2)_2O(CH_2)_2$— | |
| F-70 | $Bu^s$ | H | H | H | H | Allyl | —$(CH_2)_2O(CH_2)_2$— | |
| F-71 | OMe | H | OMe | H | H | Allyl | —$(CH_2)_2O(CH_2)_2$— | |
| F-72 | H | OMe | OMe | H | H | Allyl | —$(CH_2)_2O(CH_2)_2$— | |
| F-73 | H | OMe | OEt | H | H | Allyl | —$(CH_2)_2O(CH_2)_2$— | |
| F-74 | H | OEt | OMe | H | H | Allyl | —$(CH_2)_2O(CH_2)_2$— | |
| F-75 | H | OEt | OEt | H | H | Allyl | —$(CH_2)_2O(CH_2)_2$— | |
| F-76 | OMe | H | Me | H | H | Allyl | —$(CH_2)_2O(CH_2)_2$— | |
| F-77 | OMe | H | Et | H | H | Allyl | —$(CH_2)_2O(CH_2)_2$— | |
| F-78 | —$(CH_2)_3$— | | H | H | H | Allyl | —$(CH_2)_2O(CH_2)_2$— | |
| F-79 | —$(CH_2)_4$— | | H | H | H | Allyl | —$(CH_2)_2O(CH_2)_2$— | |

TABLE 43

| | R¹ | R² | R³ | R⁴ | R⁵ | R⁶ | R⁷ | R⁸ |
|---|---|---|---|---|---|---|---|---|
| G-1 | H | H | H | H | H | CH₂CH=CHMe | Me | Me |
| G-2 | Cl | H | H | H | H | CH₂CH=CHMe | Me | Me |
| G-3 | Br | H | H | H | H | CH₂CH=CHMe | Me | Me |
| G-4 | Me | H | H | H | H | CH₂CH=CHMe | Me | Me |
| G-5 | Et | H | H | H | H | CH₂CH=CHMe | Me | Me |
| G-6 | Pr | H | H | H | H | CH₂CH=CHMe | Me | Me |
| G-7 | Bu | H | H | H | H | CH₂CH=CHMe | Me | Me |
| G-8 | Buⁱ | H | H | H | H | CH₂CH=CHMe | Me | Me |
| G-9 | Buᵗ | H | H | H | H | CH₂CH=CHMe | Me | Me |
| G-10 | OMe | H | H | H | H | CH₂CH=CHMe | Me | Me |
| G-11 | OEt | H | H | H | H | CH₂CH=CHMe | Me | Me |
| G-12 | OPrⁱ | H | H | H | H | CH₂CH=CHMe | Me | Me |
| G-13 | OPr | H | H | H | H | CH₂CH=CHMe | Me | Me |
| G-14 | OCHF₂ | H | H | H | H | CH₂CH=CHMe | Me | Me |
| G-15 | OCF₃ | H | H | H | H | CH₂CH=CHMe | Me | Me |
| G-16 | CF₃ | H | H | H | H | CH₂CH=CHMe | Me | Me |
| G-17 | SMe | H | H | H | H | CH₂CH=CHMe | Me | Me |
| G-18 | SEt | H | H | H | H | CH₂CH=CHMe | Me | Me |
| G-19 | SPrⁱ | H | H | H | H | CH₂CH=CHMe | Me | Me |
| G-20 | NMe₂ | H | H | H | H | CH₂CH=CHMe | Me | Me |
| G-21 | NEt₂ | H | H | H | H | CH₂CH=CHMe | Me | Me |
| G-22 | H | Cl | H | H | H | CH₂CH=CHMe | Me | Me |
| G-23 | H | Br | H | H | H | CH₂CH=CHMe | Me | Me |
| G-24 | H | Me | H | H | H | CH₂CH=CHMe | Me | Me |
| G-25 | H | Et | H | H | H | CH₂CH=CHMe | Me | Me |

TABLE 44

| | R¹ | R² | R³ | R⁴ | R⁵ | R⁶ | R⁷ | R⁸ |
|---|---|---|---|---|---|---|---|---|
| G-26 | H | Pr | H | H | H | CH₂CH=CHMe | Me | Me |
| G-27 | H | Prⁱ | H | H | H | CH₂CH=CHMe | Me | Me |
| G-28 | H | Bu | H | H | H | CH₂CH=CHMe | Me | Me |
| G-29 | H | Buⁱ | H | H | H | CH₂CH=CHMe | Me | Me |
| G-30 | H | Buˢ | H | H | H | CH₂CH=CHMe | Me | Me |
| G-31 | H | Buᵗ | H | H | H | CH₂CH=CHMe | Me | Me |
| G-32 | H | OMe | H | H | H | CH₂CH=CHMe | Me | Me |
| G-33 | H | OEt | H | H | H | CH₂CH=CHMe | Me | Me |
| G-34 | H | OPr | H | H | H | CH₂CH=CHMe | Me | Me |
| G-35 | H | OPrⁱ | H | H | H | CH₂CH=CHMe | Me | Me |
| G-36 | H | OCHF₂ | H | H | H | CH₂CH=CHMe | Me | Me |
| G-37 | H | OCF₃ | H | H | H | CH₂CH=CHMe | Me | Me |
| G-38 | H | CF₃ | H | H | H | CH₂CH=CHMe | Me | Me |
| G-39 | H | SMe | H | H | H | CH₂CH=CHMe | Me | Me |
| G-40 | H | SEt | H | H | H | CH₂CH=CHMe | Me | Me |
| G-41 | H | SPrⁱ | H | H | H | CH₂CH=CHMe | Me | Me |
| G-42 | H | NMe₂ | H | H | H | CH₂CH=CHMe | Me | Me |
| G-43 | H | NEt₂ | H | H | H | CH₂CH=CHMe | Me | Me |
| G-44 | H | H | Cl | H | H | CH₂CH=CHMe | Me | Me |
| G-45 | H | H | Br | H | H | CH₂CH=CHMe | Me | Me |
| G-46 | H | H | Me | H | H | CH₂CH=CHMe | Me | Me |
| G-47 | H | H | Et | H | H | CH₂CH=CHMe | Me | Me |
| G-48 | H | H | Pr | H | H | CH₂CH=CHMe | Me | Me |
| G-49 | H | H | Prⁱ | H | H | CH₂CH=CHMe | Me | Me |
| G-50 | H | H | Bu | H | H | CH₂CH=CHMe | Me | Me |

TABLE 45

| | R¹ | R² | R³ | R⁴ | R⁵ | R⁶ | R⁷ | R⁸ |
|---|---|---|---|---|---|---|---|---|
| G-51 | H | H | Buⁱ | H | H | CH₂CH=CHMe | Me | Me |
| G-52 | H | H | Buˢ | H | H | CH₂CH=CHMe | Me | Me |
| G-53 | H | H | Buᵗ | H | H | CH₂CH=CHMe | Me | Me |
| G-54 | H | H | OMe | H | H | CH₂CH=CHMe | Me | Me |
| G-55 | H | H | OEt | H | H | CH₂CH=CHMe | Me | Me |
| G-56 | H | H | OPr | H | H | CH₂CH=CHMe | Me | Me |
| G-57 | H | H | OPrⁱ | H | H | CH₂CH=CHMe | Me | Me |
| G-58 | H | H | OCHF₂ | H | H | CH₂CH=CHMe | Me | Me |
| G-59 | H | H | OCF₃ | H | H | CH₂CH=CHMe | Me | Me |
| G-60 | H | H | CF₃ | H | H | CH₂CH=CHMe | Me | Me |
| G-61 | H | H | SMe | H | H | CH₂CH=CHMe | Me | Me |
| G-62 | H | H | SEt | H | H | CH₂CH=CHMe | Me | Me |
| G-63 | H | H | SPrⁱ | H | H | CH₂CH=CHMe | Me | Me |
| G-64 | H | H | NMe₂ | H | H | CH₂CH=CHMe | Me | Me |
| G-65 | H | H | NEt₂ | H | H | CH₂CH=CHMe | Me | Me |
| G-66 | Et | NMe₂ | H | H | H | CH₂CH=CHMe | Me | Me |
| G-67 | NMe₂ | Cl | H | H | H | CH₂CH=CHMe | Me | Me |
| G-68 | Et | NEt₂ | H | H | H | CH₂CH=CHMe | Me | Me |
| G-69 | H | NEt₂ | Me | H | H | CH₂CH=CHMe | Me | Me |
| G-70 | Buˢ | H | H | H | H | CH₂CH=CHMe | Me | Me |
| G-71 | OMe | H | OMe | H | H | CH₂CH=CHMe | Me | Me |
| G-72 | H | OMe | OMe | H | H | CH₂CH=CHMe | Me | Me |
| G-73 | H | OMe | OEt | H | H | CH₂CH=CHMe | Me | Me |
| G-74 | H | OEt | OMe | H | H | CH₂CH=CHMe | Me | Me |
| G-75 | H | OEt | OEt | H | H | CH₂CH=CHMe | Me | Me |
| G-76 | OMe | H | Me | H | H | CH₂CH=CHMe | Me | Me |
| G-77 | OMe | H | Et | H | H | CH₂CH=CHMe | Me | Me |
| G-78 | —(CH₂)₃— | | H | H | CH₂CH=CHMe | Me | Me |
| G-79 | —(CH₂)₄— | | H | H | CH₂CH=CHMe | Me | Me |

TABLE 46

| | $R^1$ | $R^2$ | $R^3$ | $R^4$ | $R^5$ | $R^6$ | $R^7$ | $R^8$ |
|---|---|---|---|---|---|---|---|---|
| H-1 | H | H | H | H | H | CH₂CH=CHMe | Et | Et |
| H-2 | Cl | H | H | H | H | CH₂CH=CHMe | Et | Et |
| H-3 | Br | H | H | H | H | CH₂CH=CHMe | Et | Et |
| H-4 | Me | H | H | H | H | CH₂CH=CHMe | Et | Et |
| H-5 | Et | H | H | H | H | CH₂CH=CHMe | Et | Et |
| H-6 | Pr | H | H | H | H | CH₂CH=CHMe | Et | Et |
| H-7 | Bu | H | H | H | H | CH₂CH=CHMe | Et | Et |
| H-8 | Buⁱ | H | H | H | H | CH₂CH=CHMe | Et | Et |
| H-9 | Buᵗ | H | H | H | H | CH₂CH=CHMe | Et | Et |
| H-10 | OMe | H | H | H | H | CH₂CH=CHMe | Et | Et |
| H-11 | OEt | H | H | H | H | CH₂CH=CHMe | Et | Et |
| H-12 | OPrⁱ | H | H | H | H | CH₂CH=CHMe | Et | Et |
| H-13 | OPr | H | H | H | H | CH₂CH=CHMe | Et | Et |
| H-14 | OCHF₂ | H | H | H | H | CH₂CH=CHMe | Et | Et |
| H-15 | OCF₃ | H | H | H | H | CH₂CH=CHMe | Et | Et |
| H-16 | CF₃ | H | H | H | H | CH₂CH=CHMe | Et | Et |
| H-17 | SMe | H | H | H | H | CH₂CH=CHMe | Et | Et |
| H-18 | SEt | H | H | H | H | CH₂CH=CHMe | Et | Et |
| H-19 | SPrⁱ | H | H | H | H | CH₂CH=CHMe | Et | Et |
| H-20 | NMe₂ | H | H | H | H | CH₂CH=CHMe | Et | Et |
| H-21 | NEt₂ | H | H | H | H | CH₂CH=CHMe | Et | Et |
| H-22 | H | Cl | H | H | H | CH₂CH=CHMe | Et | Et |
| H-23 | H | Br | H | H | H | CH₂CH=CHMe | Et | Et |
| H-24 | H | Me | H | H | H | CH₂CH=CHMe | Et | Et |
| H-25 | H | Et | H | H | H | CH₂CH=CHMe | Et | Et |

TABLE 47

| | $R^1$ | $R^2$ | $R^3$ | $R^4$ | $R^5$ | $R^6$ | $R^7$ | $R^8$ |
|---|---|---|---|---|---|---|---|---|
| H-26 | H | Pr | H | H | H | CH₂CH=CHMe | Et | Et |
| H-27 | H | Prⁱ | H | H | H | CH₂CH=CHMe | Et | Et |
| H-28 | H | Bu | H | H | H | CH₂CH=CHMe | Et | Et |
| H-29 | H | Buⁱ | H | H | H | CH₂CH=CHMe | Et | Et |
| H-30 | H | Buˢ | H | H | H | CH₂CH=CHMe | Et | Et |
| H-31 | H | Buᵗ | H | H | H | CH₂CH=CHMe | Et | Et |
| H-32 | H | OMe | H | H | H | CH₂CH=CHMe | Et | Et |
| H-33 | H | OEt | H | H | H | CH₂CH=CHMe | Et | Et |
| H-34 | H | OPr | H | H | H | CH₂CH=CHMe | Et | Et |
| H-35 | H | OPrⁱ | H | H | H | CH₂CH=CHMe | Et | Et |
| H-36 | H | OCHF₂ | H | H | H | CH₂CH=CHMe | Et | Et |
| H-37 | H | OCF₃ | H | H | H | CH₂CH=CHMe | Et | Et |
| H-38 | H | CF₃ | H | H | H | CH₂CH=CHMe | Et | Et |
| H-39 | H | SMe | H | H | H | CH₂CH=CHMe | Et | Et |
| H-40 | H | SEt | H | H | H | CH₂CH=CHMe | Et | Et |
| H-41 | H | SPrⁱ | H | H | H | CH₂CH=CHMe | Et | Et |
| H-42 | H | NMe₂ | H | H | H | CH₂CH=CHMe | Et | Et |
| H-43 | H | NEt₂ | H | H | H | CH₂CH=CHMe | Et | Et |
| H-44 | H | H | Cl | H | H | CH₂CH=CHMe | Et | Et |
| H-45 | H | H | Br | H | H | CH₂CH=CHMe | Et | Et |
| H-46 | H | H | Me | H | H | CH₂CH=CHMe | Et | Et |
| H-47 | H | H | Et | H | H | CH₂CH=CHMe | Et | Et |
| H-48 | H | H | Pr | H | H | CH₂CH=CHMe | Et | Et |
| H-49 | H | H | Prⁱ | H | H | CH₂CH=CHMe | Et | Et |
| H-50 | H | H | Bu | H | H | CH₂CH=CHMe | Et | Et |

TABLE 48

| | $R^1$ | $R^2$ | $R^3$ | $R^4$ | $R^5$ | $R^6$ | $R^7$ | $R^8$ |
|---|---|---|---|---|---|---|---|---|
| H-51 | H | H | Buⁱ | H | H | CH₂CH=CHMe | Et | Et |
| H-52 | H | H | Buˢ | H | H | CH₂CH=CHMe | Et | Et |
| H-53 | H | H | Buᵗ | H | H | CH₂CH=CHMe | Et | Et |
| H-54 | H | H | OMe | H | H | CH₂CH=CHMe | Et | Et |
| H-55 | H | H | OEt | H | H | CH₂CH=CHMe | Et | Et |
| H-56 | H | H | OPr | H | H | CH₂CH=CHMe | Et | Et |
| H-57 | H | H | OPrⁱ | H | H | CH₂CH=CHMe | Et | Et |
| H-58 | H | H | OCHF₂ | H | H | CH₂CH=CHMe | Et | Et |
| H-59 | H | H | OCF₃ | H | H | CH₂CH=CHMe | Et | Et |
| H-60 | H | H | CF₃ | H | H | CH₂CH=CHMe | Et | Et |
| H-61 | H | H | SMe | H | H | CH₂CH=CHMe | Et | Et |
| H-62 | H | H | SEt | H | H | CH₂CH=CHMe | Et | Et |
| H-63 | H | H | SPrⁱ | H | H | CH₂CH=CHMe | Et | Et |
| H-64 | H | H | NMe₂ | H | H | CH₂CH=CHMe | Et | Et |
| H-65 | H | H | NEt₂ | H | H | CH₂CH=CHMe | Et | Et |
| H-66 | Et | NMe₂ | H | H | H | CH₂CH=CHMe | Et | Et |
| H-67 | NMe₂ | Cl | H | H | H | CH₂CH=CHMe | Et | Et |
| H-68 | Et | NEt₂ | H | H | H | CH₂CH=CHMe | Et | Et |
| H-69 | H | NEt₂ | Me | H | H | CH₂CH=CHMe | Et | Et |
| H-70 | Buˢ | H | H | H | H | CH₂CH=CHMe | Et | Et |
| H-71 | OMe | H | OMe | H | H | CH₂CH=CHMe | Et | Et |
| H-72 | H | OMe | OMe | H | H | CH₂CH=CHMe | Et | Et |
| H-73 | H | OMe | OEt | H | H | CH₂CH=CHMe | Et | Et |
| H-74 | H | OEt | OMe | H | H | CH₂CH=CHMe | Et | Et |
| H-75 | H | OEt | OEt | H | H | CH₂CH=CHMe | Et | Et |
| H-76 | OMe | H | Me | H | H | CH₂CH=CHMe | Et | Et |
| H-77 | OMe | H | Et | H | H | CH₂CH=CHMe | Et | Et |
| H-78 | —(CH₂)₃— | | H | H | H | CH₂CH=CHMe | Et | Et |
| H-79 | —(CH₂)₄— | | H | H | H | CH₂CH=CHMe | Et | Et |

TABLE 49

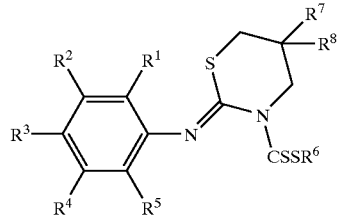

| | R¹ | R² | R³ | R⁴ | R⁵ | R⁶ | R⁷ R⁸ |
|---|---|---|---|---|---|---|---|
| J-1 | H | H | H | H | H | CH$_2$CH=CHMe | —(CH$_2$)$_4$— |
| J-2 | Cl | H | H | H | H | CH$_2$CH=CHMe | —(CH$_2$)$_4$— |
| J-3 | Br | H | H | H | H | CH$_2$CH=CHMe | —(CH$_2$)$_4$— |
| J-4 | Me | H | H | H | H | CH$_2$CH=CHMe | —(CH$_2$)$_4$— |
| J-5 | Et | H | H | H | H | CH$_2$CH=CHMe | —(CH$_2$)$_4$— |
| J-6 | Pr | H | H | H | H | CH$_2$CH=CHMe | —(CH$_2$)$_4$— |
| J-7 | Bu | H | H | H | H | CH$_2$CH=CHMe | —(CH$_2$)$_4$— |
| J-8 | Bu$^i$ | H | H | H | H | CH$_2$CH=CHMe | —(CH$_2$)$_4$— |
| J-9 | Bu$^t$ | H | H | H | H | CH$_2$CH=CHMe | —(CH$_2$)$_4$— |
| J-10 | OMe | H | H | H | H | CH$_2$CH=CHMe | —(CH$_2$)$_4$— |
| J-11 | OEt | H | H | H | H | CH$_2$CH=CHMe | —(CH$_2$)$_4$— |
| J-12 | OPr$^i$ | H | H | H | H | CH$_2$CH=CHMe | —(CH$_2$)$_4$— |
| J-13 | OPr | H | H | H | H | CH$_2$CH=CHMe | —(CH$_2$)$_4$— |
| J-14 | OCHF$_2$ | H | H | H | H | CH$_2$CH=CHMe | —(CH$_2$)$_4$— |
| J-15 | OCF$_3$ | H | H | H | H | CH$_2$CH=CHMe | —(CH$_2$)$_4$— |
| J-16 | CF$_3$ | H | H | H | H | CH$_2$CH=CHMe | —(CH$_2$)$_4$— |
| J-17 | SMe | H | H | H | H | CH$_2$CH=CHMe | —(CH$_2$)$_4$— |
| J-18 | SEt | H | H | H | H | CH$_2$CH=CHMe | —(CH$_2$)$_4$— |
| J-19 | SPr$^i$ | H | H | H | H | CH$_2$CH=CHMe | —(CH$_2$)$_4$— |
| J-20 | NMe$_2$ | H | H | H | H | CH$_2$CH=CHMe | —(CH$_2$)$_4$— |
| J-21 | NEt$_2$ | H | H | H | H | CH$_2$CH=CHMe | —(CH$_2$)$_4$— |
| J-22 | H | Cl | H | H | H | CH$_2$CH=CHMe | —(CH$_2$)$_4$— |
| J-23 | H | Br | H | H | H | CH$_2$CH=CHMe | —(CH$_2$)$_4$— |
| J-24 | H | Me | H | H | H | CH$_2$CH=CHMe | —(CH$_2$)$_4$— |
| J-25 | H | Et | H | H | H | CH$_2$CH=CHMe | —(CH$_2$)$_4$— |

TABLE 50

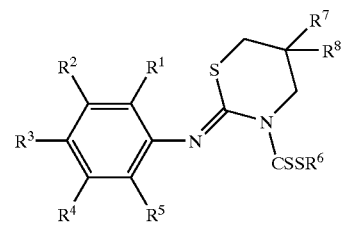

| | R¹ | R² | R³ | R⁴ | R⁵ | R⁶ | R⁷ R⁸ |
|---|---|---|---|---|---|---|---|
| J-26 | H | Pr | H | H | H | CH$_2$CH=CHMe | —(CH$_2$)$_4$— |
| J-27 | H | Pr$^i$ | H | H | H | CH$_2$CH=CHMe | —(CH$_2$)$_4$— |
| J-28 | H | Bu | H | H | H | CH$_2$CH=CHMe | —(CH$_2$)$_4$— |
| J-29 | H | Bu$^i$ | H | H | H | CH$_2$CH=CHMe | —(CH$_2$)$_4$— |
| J-30 | H | Bu$^s$ | H | H | H | CH$_2$CH=CHMe | —(CH$_2$)$_4$— |
| J-31 | H | Bu$^t$ | H | H | H | CH$_2$CH=CHMe | —(CH$_2$)$_4$— |
| J-32 | H | OMe | H | H | H | CH$_2$CH=CHMe | —(CH$_2$)$_4$— |
| J-33 | H | OEt | H | H | H | CH$_2$CH=CHMe | —(CH$_2$)$_4$— |
| J-34 | H | OPr | H | H | H | CH$_2$CH=CHMe | —(CH$_2$)$_4$— |
| J-35 | H | OPr$^i$ | H | H | H | CH$_2$CH=CHMe | —(CH$_2$)$_4$— |
| J-36 | H | OCHF$_2$ | H | H | H | CH$_2$CH=CHMe | —(CH$_2$)$_4$— |
| J-37 | H | OCF$_3$ | H | H | H | CH$_2$CH=CHMe | —(CH$_2$)$_4$— |
| J-38 | H | CF$_3$ | H | H | H | CH$_2$CH=CHMe | —(CH$_2$)$_4$— |
| J-39 | H | SMe | H | H | H | CH$_2$CH=CHMe | —(CH$_2$)$_4$— |
| J-40 | H | SEt | H | H | H | CH$_2$CH=CHMe | —(CH$_2$)$_4$— |
| J-41 | H | SPr$^i$ | H | H | H | CH$_2$CH=CHMe | —(CH$_2$)$_4$— |
| J-42 | H | NMe$_2$ | H | H | H | CH$_2$CH=CHMe | —(CH$_2$)$_4$— |
| J-43 | H | NEt$_2$ | H | H | H | CH$_2$CH=CHMe | —(CH$_2$)$_4$— |
| J-44 | H | H | Cl | H | H | CH$_2$CH=CHMe | —(CH$_2$)$_4$— |
| J-45 | H | H | Br | H | H | CH$_2$CH=CHMe | —(CH$_2$)$_4$— |
| J-46 | H | H | Me | H | H | CH$_2$CH=CHMe | —(CH$_2$)$_4$— |
| J-47 | H | H | Et | H | H | CH$_2$CH=CHMe | —(CH$_2$)$_4$— |
| J-48 | H | H | Pr | H | H | CH$_2$CH=CHMe | —(CH$_2$)$_4$— |
| J-49 | H | H | Pr$^i$ | H | H | CH$_2$CH=CHMe | —(CH$_2$)$_4$— |
| J-50 | H | H | Bu | H | H | CH$_2$CH=CHMe | —(CH$_2$)$_4$— |

TABLE 51

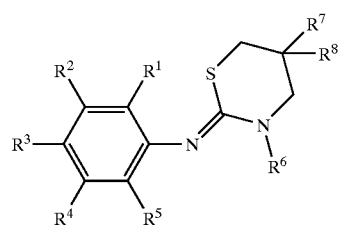

| | R¹ | R² | R³ | R⁴ | R⁵ | R⁶ | R⁷ R⁸ |
|---|---|---|---|---|---|---|---|
| J-51 | H | H | Bu$^i$ | H | H | CH$_2$CH=CHMe | —(CH$_2$)$_4$— |
| J-52 | H | H | Bu$^s$ | H | H | CH$_2$CH=CHMe | —(CH$_2$)$_4$— |
| J-53 | H | H | Bu$^t$ | H | H | CH$_2$CH=CHMe | —(CH$_2$)$_4$— |
| J-54 | H | H | OMe | H | H | CH$_2$CH=CHMe | —(CH$_2$)$_4$— |
| J-55 | H | H | OEt | H | H | CH$_2$CH=CHMe | —(CH$_2$)$_4$— |

TABLE 51-continued

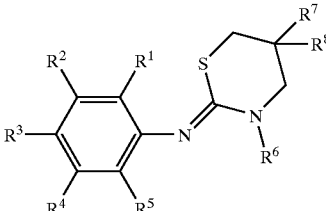

|  | R¹ | R² | R³ | R⁴ | R⁵ | R⁶ | R⁷ R⁸ |
|---|---|---|---|---|---|---|---|
| J-56 | H | H | OPr | H | H | CH₂CH=CHMe | —(CH₂)₄— |
| J-57 | H | H | OPr$^i$ | H | H | CH₂CH=CHMe | —(CH₂)₄— |
| J-58 | H | H | OCHF₂ | H | H | CH₂CH=CHMe | —(CH₂)₄— |
| J-59 | H | H | OCF₃ | H | H | CH₂CH=CHMe | —(CH₂)₄— |
| J-60 | H | H | CF₃ | H | H | CH₂CH=CHMe | —(CH₂)₄— |
| J-61 | H | H | SMe | H | H | CH₂CH=CHMe | —(CH₂)₄— |
| J-62 | H | H | SEt | H | H | CH₂CH=CHMe | —(CH₂)₄— |
| J-63 | H | H | SPr$^i$ | H | H | CH₂CH=CHMe | —(CH₂)₄— |
| J-64 | H | H | NMe₂ | H | H | CH₂CH=CHMe | —(CH₂)₄— |
| J-65 | H | H | NEt₂ | H | H | CH₂CH=CHMe | —(CH₂)₄— |
| J-66 | Me | NMe₂ | H | H | H | CH₂CH=CHMe | —(CH₂)₄— |
| J-67 | NMe₂ | Cl | H | H | H | CH₂CH=CHMe | —(CH₂)₄— |
| J-68 | Me | NEt₂ | H | H | H | CH₂CH=CHMe | —(CH₂)₄— |
| J-69 | H | NEt₂ | Me | H | H | CH₂CH=CHMe | —(CH₂)₄— |
| J-70 | Bu$^s$ | H | H | H | H | CH₂CH=CHMe | —(CH₂)₄— |
| J-71 | Pr$^i$ | H | H | H | H | CH₂CH=CHMe | —(CH₂)₄— |
| J-72 | H | OMe | OMe | H | H | CH₂CH=CHMe | —(CH₂)₄— |
| J-73 | H | OMe | OEt | H | H | CH₂CH=CHMe | —(CH₂)₄— |
| J-74 | H | OEt | OMe | H | H | CH₂CH=CHMe | —(CH₂)₄— |
| J-75 | H | OEt | OEt | H | H | CH₂CH=CHMe | —(CH₂)₄— |
| J-76 | OMe | H | Me | H | H | CH₂CH=CHMe | —(CH₂)₄— |
| J-77 | OMe | H | Et | H | H | CH₂CH=CHMe | —(CH₂)₄— |
| J-78 | —(CH₂)₃— | | H | H | H | CH₂CH=CHMe | —(CH₂)₄— |
| J-79 | —(CH₂)₄— | | H | H | H | CH₂CH=CHMe | —(CH₂)₄— |

TABLE 52

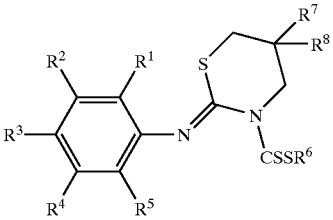

|  | R¹ | R² | R³ | R⁴ | R⁵ | R⁶ | R⁷ R⁸ |
|---|---|---|---|---|---|---|---|
| K-1 | H | H | H | H | H | CH₂CH=CHMe | —(CH₂)₅— |
| K-2 | Cl | H | H | H | H | CH₂CH=CHMe | —(CH₂)₅— |
| K-3 | Br | H | H | H | H | CH₂CH=CHMe | —(CH₂)₅— |
| K-4 | Me | H | H | H | H | CH₂CH=CHMe | —(CH₂)₅— |
| K-5 | Et | H | H | H | H | CH₂CH=CHMe | —(CH₂)₅— |
| K-6 | Pr | H | H | H | H | CH₂CH=CHMe | —(CH₂)₅— |
| K-7 | Bu | H | H | H | H | CH₂CH=CHMe | —(CH₂)₅— |
| K-8 | Bu$^i$ | H | H | H | H | CH₂CH=CHMe | —(CH₂)₅— |
| K-9 | Bu$^t$ | H | H | H | H | CH₂CH=CHMe | —(CH₂)₅— |
| K-10 | OMe | H | H | H | H | CH₂CH=CHMe | —(CH₂)₅— |
| K-11 | OEt | H | H | H | H | CH₂CH=CHMe | —(CH₂)₅— |
| K-12 | OPr$^i$ | H | H | H | H | CH₂CH=CHMe | —(CH₂)₅— |
| K-13 | OPr | H | H | H | H | CH₂CH=CHMe | —(CH₂)₅— |
| K-14 | OCHF₂ | H | H | H | H | CH₂CH=CHMe | —(CH₂)₅— |
| K-15 | OCF₃ | H | H | H | H | CH₂CH=CHMe | —(CH₂)₅— |
| K-16 | CF₃ | H | H | H | H | CH₂CH=CHMe | —(CH₂)₅— |

TABLE 52-continued

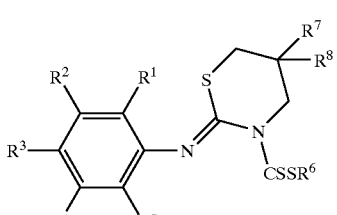

|  | R¹ | R² | R³ | R⁴ | R⁵ | R⁶ | R⁷ R⁸ |
|---|---|---|---|---|---|---|---|
| K-17 | SMe | H | H | H | H | CH₂CH=CHMe | —(CH₂)₅— |
| K-18 | SEt | H | H | H | H | CH₂CH=CHMe | —(CH₂)₅— |
| K-19 | SPr$^i$ | H | H | H | H | CH₂CH=CHMe | —(CH₂)₅— |
| K-20 | NMe₂ | H | H | H | H | CH₂CH=CHMe | —(CH₂)₅— |
| K-21 | NEt₂ | H | H | H | H | CH₂CH=CHMe | —(CH₂)₅— |
| K-22 | H | Cl | H | H | H | CH₂CH=CHMe | —(CH₂)₅— |
| K-23 | H | Br | H | H | H | CH₂CH=CHMe | —(CH₂)₅— |
| K-24 | H | Me | H | H | H | CH₂CH=CHMe | —(CH₂)₅— |
| K-25 | H | Et | H | H | H | CH₂CH=CHMe | —(CH₂)₅— |

TABLE 53

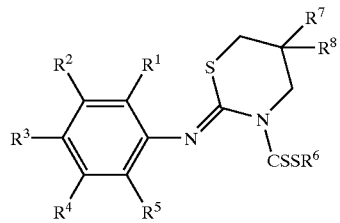

| | R¹ | R² | R³ | R⁴ | R⁵ | R⁶ | R⁷ | R⁸ |
|---|---|---|---|---|---|---|---|---|
| K-26 | H | Pr | H | H | H | CH₂CH=CHMe | —(CH₂)₅— | |
| K-27 | H | Pr$^i$ | H | H | H | CH₂CH=CHMe | —(CH₂)₅— | |
| K-28 | H | Bu | H | H | H | CH₂CH=CHMe | —(CH₂)₅— | |
| K-29 | H | Bu$^i$ | H | H | H | CH₂CH=CHMe | —(CH₂)₅— | |
| K-30 | H | Bu$^s$ | H | H | H | CH₂CH=CHMe | —(CH₂)₅— | |
| K-31 | H | Bu$^t$ | H | H | H | CH₂CH=CHMe | —(CH₂)₅— | |
| K-32 | H | OMe | H | H | H | CH₂CH=CHMe | —(CH₂)₅— | |
| K-33 | H | OEt | H | H | H | CH₂CH=CHMe | —(CH₂)₅— | |
| K-34 | H | OPr | H | H | H | CH₂CH=CHMe | —(CH₂)₅— | |
| K-35 | H | OPr$^i$ | H | H | H | CH₂CH=CHMe | —(CH₂)₅— | |
| K-36 | H | OCHF₂ | H | H | H | CH₂CH=CHMe | —(CH₂)₅— | |
| K-37 | H | OCF₃ | H | H | H | CH₂CH=CHMe | —(CH₂)₅— | |
| K-38 | H | CF₃ | H | H | H | CH₂CH=CHMe | —(CH₂)₅— | |

TABLE 53-continued

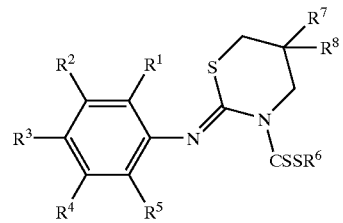

| | R¹ | R² | R³ | R⁴ | R⁵ | R⁶ | R⁷ | R⁸ |
|---|---|---|---|---|---|---|---|---|
| K-39 | H | SMe | H | H | H | CH₂CH=CHMe | —(CH₂)₅— | |
| K-40 | H | SEt | H | H | H | CH₂CH=CHMe | —(CH₂)₅— | |
| K-41 | H | SPr$^i$ | H | H | H | CH₂CH=CHMe | —(CH₂)₅— | |
| K-42 | H | NMe₂ | H | H | H | CH₂CH=CHMe | —(CH₂)₅— | |
| K-43 | H | NEt₂ | H | H | H | CH₂CH=CHMe | —(CH₂)₅— | |
| K-44 | H | H | Cl | H | H | CH₂CH=CHMe | —(CH₂)₅— | |
| K-45 | H | H | Br | H | H | CH₂CH=CHMe | —(CH₂)₅— | |
| K-46 | H | H | Me | H | H | CH₂CH=CHMe | —(CH₂)₅— | |
| K-47 | H | H | Et | H | H | CH₂CH=CHMe | —(CH₂)₅— | |
| K-48 | H | H | Pr | H | H | CH₂CH=CHMe | —(CH₂)₅— | |
| K-49 | H | H | Pr$^i$ | H | H | CH₂CH=CHMe | —(CH₂)₅— | |
| K-50 | H | H | Bu | H | H | CH₂CH=CHMe | —(CH₂)₅— | |

TABLE 54

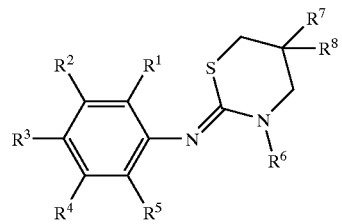

| | R¹ | R² | R³ | R⁴ | R⁵ | R⁶ | R⁷ | R⁸ |
|---|---|---|---|---|---|---|---|---|
| K-51 | H | H | Bu$^i$ | H | H | CH₂CH=CHMe | —(CH₂)₅— | |
| K-52 | H | H | Bu$^s$ | H | H | CH₂CH=CHMe | —(CH₂)₅— | |
| K-53 | H | H | Bu$^t$ | H | H | CH₂CH=CHMe | —(CH₂)₅— | |
| K-54 | H | H | OMe | H | H | CH₂CH=CHMe | —(CH₂)₅— | |
| K-55 | H | H | OEt | H | H | CH₂CH=CHMe | —(CH₂)₅— | |
| K-56 | H | H | OPr | H | H | CH₂CH=CHMe | —(CH₂)₅— | |
| K-57 | H | H | OPr$^i$ | H | H | CH₂CH=CHMe | —(CH₂)₅— | |
| K-58 | H | H | OCHF₂ | H | H | CH₂CH=CHMe | —(CH₂)₅— | |
| K-59 | H | H | OCF₃ | H | H | CH₂CH=CHMe | —(CH₂)₅— | |
| K-60 | H | H | CF₃ | H | H | CH₂CH=CHMe | —(CH₂)₅— | |
| K-61 | H | H | SMe | H | H | CH₂CH=CHMe | —(CH₂)₅— | |
| K-62 | H | H | SEt | H | H | CH₂CH=CHMe | —(CH₂)₅— | |
| K-63 | H | H | SPr$^i$ | H | H | CH₂CH=CHMe | —(CH₂)₅— | |
| K-64 | H | H | NMe₂ | H | H | CH₂CH=CHMe | —(CH₂)₅— | |
| K-65 | H | H | NEt₂ | H | H | CH₂CH=CHMe | —(CH₂)₅— | |
| K-66 | Me | NMe₂ | H | H | H | CH₂CH=CHMe | —(CH₂)₅— | |
| K-67 | NMe₂ | Cl | H | H | H | CH₂CH=CHMe | —(CH₂)₅— | |
| K-68 | Me | NEt₂ | H | H | H | CH₂CH=CHMe | —(CH₂)₅— | |
| K-69 | H | NEt₂ | Me | H | H | CH₂CH=CHMe | —(CH₂)₅— | |
| K-70 | Bu$^s$ | H | H | H | H | CH₂CH=CHMe | —(CH₂)₅— | |
| K-71 | Pr$^i$ | H | H | H | H | CH₂CH=CHMe | —(CH₂)₅— | |
| K-72 | H | OMe | OMe | H | H | CH₂CH=CHMe | —(CH₂)₅— | |
| K-73 | H | OMe | OEt | H | H | CH₂CH=CHMe | —(CH₂)₅— | |
| K-74 | H | OEt | OMe | H | H | CH₂CH=CHMe | —(CH₂)₅— | |
| K-75 | H | OEt | OEt | H | H | CH₂CH=CHMe | —(CH₂)₅— | |

TABLE 54-continued

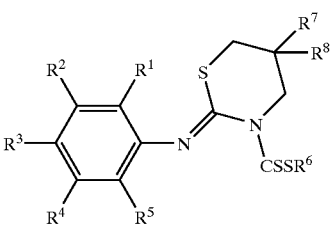

| | R¹ | R² | R³ | R⁴ | R⁵ | R⁶ | R⁷ | R⁸ |
|---|---|---|---|---|---|---|---|---|
| K-76 | OMe | H | Me | H | H | CH₂CH=CHMe | —(CH₂)₅— | |
| K-77 | OMe | H | Et | H | H | CH₂CH=CHMe | —(CH₂)₅— | |
| K-78 | —(CH₂)₃— | | H | H | H | CH₂CH=CHMe | —(CH₂)₅— | |
| K-79 | —(CH₂)₄— | | H | H | H | CH₂CH=CHMe | —(CH₂)₅— | |

TABLE 55

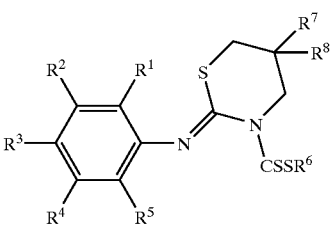

| | R¹ | R² | R³ | R⁴ | R⁵ | R⁶ | R⁷ | R⁸ |
|---|---|---|---|---|---|---|---|---|
| L-1 | H | H | H | H | H | CH₂CO₂Buᵗ | Me | Me |
| L-2 | Cl | H | H | H | H | CH₂CO₂Buᵗ | Me | Me |
| L-3 | Br | H | H | H | H | CH₂CO₂Buᵗ | Me | Me |
| L-4 | Me | H | H | H | H | CH₂CO₂Buᵗ | Me | Me |
| L-5 | Et | H | H | H | H | CH₂CO₂Buᵗ | Me | Me |
| L-6 | Pr | H | H | H | H | CH₂CO₂Buᵗ | Me | Me |
| L-7 | Bu | H | H | H | H | CH₂CO₂Buᵗ | Me | Me |
| L-8 | Buⁱ | H | H | H | H | CH₂CO₂Buᵗ | Me | Me |
| L-9 | Buᵗ | H | H | H | H | CH₂CO₂Buᵗ | Me | Me |
| L-10 | OMe | H | Et | H | H | CH₂CO₂Buᵗ | Me | Me |
| L-11 | OEt | H | H | H | H | CH₂CO₂Buᵗ | Me | Me |
| L-12 | OPrⁱ | H | H | H | H | CH₂CO₂Buᵗ | Me | Me |
| L-13 | OPr | H | H | H | H | CH₂CO₂Buᵗ | Me | Me |
| L-14 | OCHF₂ | H | H | H | H | CH₂CO₂Buᵗ | Me | Me |
| L-15 | OCF₃ | H | H | H | H | CH₂CO₂Buᵗ | Me | Me |
| L-16 | CF₃ | H | H | H | H | CH₂CO₂Buᵗ | Me | Me |
| L-17 | SMe | H | H | H | H | CH₂CO₂Buᵗ | Me | Me |
| L-18 | SEt | H | H | H | H | CH₂CO₂Buᵗ | Me | Me |
| L-19 | SPrⁱ | H | H | H | H | CH₂CO₂Buᵗ | Me | Me |
| L-20 | OEt | H | Et | H | H | CH₂CO₂Buᵗ | Me | Me |
| L-21 | NEt₂ | H | H | H | H | CH₂CO₂Buᵗ | Me | Me |
| L-22 | H | Cl | H | H | H | CH₂CO₂Buᵗ | Me | Me |
| L-23 | H | Br | H | H | H | CH₂CO₂Buᵗ | Me | Me |
| L-24 | H | Me | H | H | H | CH₂CO₂Buᵗ | Me | Me |
| L-25 | H | Et | H | H | H | CH₂CO₂Buᵗ | Me | Me |

TABLE 56

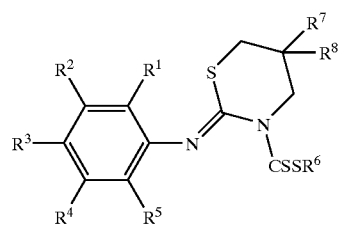

| | R¹ | R² | R³ | R⁴ | R⁵ | R⁶ | R⁷ | R⁸ |
|---|---|---|---|---|---|---|---|---|
| L-26 | H | Pr | H | H | H | CH₂CO₂Buᵗ | Me | Me |
| L-27 | OMe | H | Et | H | H | CH₂CO₂Buᵗ | Me | Me |
| L-28 | H | Bu | H | H | H | CH₂CO₂Buᵗ | Me | Me |
| L-29 | H | Buⁱ | H | H | H | CH₂CO₂Buᵗ | Me | Me |
| L-30 | H | Buˢ | H | H | H | CH₂CO₂Buᵗ | Me | Me |
| L-31 | H | Buᵗ | H | H | H | CH₂CO₂Buᵗ | Me | Me |
| L-32 | H | OMe | H | H | H | CH₂CO₂Buᵗ | Me | Me |
| L-33 | H | OEt | H | H | H | CH₂CO₂Buᵗ | Me | Me |
| L-34 | H | OPr | H | H | H | CH₂CO₂Buᵗ | Me | Me |
| L-35 | H | OPrⁱ | H | H | H | CH₂CO₂Buᵗ | Me | Me |
| L-36 | H | OCHF₂ | H | H | H | CH₂CO₂Buᵗ | Me | Me |
| L-37 | H | OCF₃ | H | H | H | CH₂CO₂Buᵗ | Me | Me |
| L-38 | H | CF₃ | H | H | H | CH₂CO₂Buᵗ | Me | Me |
| L-39 | H | SMe | H | H | H | CH₂CO₂Buᵗ | Me | Me |
| L-40 | H | SEt | H | H | H | CH₂CO₂Buᵗ | Me | Me |
| L-41 | H | SPrⁱ | H | H | H | CH₂CO₂Buᵗ | Me | Me |
| L-42 | OEt | H | Et | H | H | CH₂CO₂Buᵗ | Me | Me |
| L-43 | Prⁱ | H | OMe | H | H | CH₂CO₂Buᵗ | Me | Me |
| L-44 | H | H | Cl | H | H | CH₂CO₂Buᵗ | Me | Me |
| L-45 | H | H | Br | H | H | CH₂CO₂Buᵗ | Me | Me |
| L-46 | H | H | Me | H | H | CH₂CO₂Buᵗ | Me | Me |
| L-47 | H | H | CH₂OMe | H | H | CH₂CO₂Buᵗ | Me | Me |
| L-48 | H | H | Pr | H | H | CH₂CO₂Buᵗ | Me | Me |
| L-49 | H | H | Prⁱ | H | H | CH₂CO₂Buᵗ | Me | Me |
| L-50 | H | H | Bu | H | H | CH₂CO₂Buᵗ | Me | Me |

TABLE 57

| | R¹ | R² | R³ | R⁴ | R⁵ | R⁶ | R⁷ | R⁸ |
|---|---|---|---|---|---|---|---|---|
| L-51 | H | H | Buⁱ | H | H | CH₂CO₂Buᵗ | Me | Me |
| L-52 | H | H | Buˢ | H | H | CH₂CO₂Buᵗ | Me | Me |
| L-53 | H | H | Buᵗ | H | H | CH₂CO₂Buᵗ | Me | Me |
| L-54 | H | H | OMe | H | H | CH₂CO₂Buᵗ | Me | Me |
| L-55 | H | H | OEt | H | H | CH₂CO₂Buᵗ | Me | Me |
| L-56 | H | H | OPr | H | H | CH₂CO₂Buᵗ | Me | Me |
| L-57 | H | H | OPrⁱ | H | H | CH₂CO₂Buᵗ | Me | Me |
| L-58 | H | H | OCHF₂ | H | H | CH₂CO₂Buᵗ | Me | Me |
| L-59 | H | H | OCF₃ | H | H | CH₂CO₂Buᵗ | Me | Me |
| L-60 | H | H | CF₃ | H | H | CH₂CO₂Buᵗ | Me | Me |
| L-61 | H | H | SMe | H | H | CH₂CO₂Buᵗ | Me | Me |
| L-62 | H | H | SEt | H | H | CH₂CO₂Buᵗ | Me | Me |
| L-63 | H | H | SPrⁱ | H | H | CH₂CO₂Buᵗ | Me | Me |
| L-64 | H | H | NMe₂ | H | H | CH₂CO₂Buᵗ | Me | Me |
| L-65 | H | H | NEt₂ | H | H | CH₂CO₂Buᵗ | Me | Me |
| L-66 | Et | NMe₂ | H | H | H | CH₂CO₂Buᵗ | Me | Me |
| L-67 | NMe₂ | Cl | H | H | H | CH₂CO₂Buᵗ | Me | Me |
| L-68 | Et | NEt₂ | H | H | H | CH₂CO₂Buᵗ | Me | Me |
| L-69 | H | NEt₂ | Me | H | H | CH₂CO₂Buᵗ | Me | Me |
| L-70 | Me | NEt₂ | H | H | H | CH₂CO₂Buᵗ | Me | Me |
| L-71 | OMe | H | OMe | H | H | CH₂CO₂Buᵗ | Me | Me |
| L-72 | H | OMe | OMe | H | H | CH₂CO₂Buᵗ | Me | Me |
| L-73 | H | OMe | OEt | H | H | CH₂CO₂Buᵗ | Me | Me |
| L-74 | H | OEt | OMe | H | H | CH₂CO₂Buᵗ | Me | Me |
| L-75 | H | OEt | OEt | H | H | CH₂CO₂Buᵗ | Me | Me |
| L-76 | OMe | H | Me | H | H | CH₂CO₂Buᵗ | Me | Me |
| L-77 | OMe | H | Et | H | H | CH₂CO₂Buᵗ | Me | Me |
| L-78 | —(CH₂)₃— | | H | H | H | CH₂CO₂Buᵗ | Me | Me |
| L-79 | —(CH₂)₄— | | H | H | H | CH₂CO₂Buᵗ | Me | Me |

TABLE 58

| | R¹ | R² | R³ | R⁴ | R⁵ | R⁶ | R⁷ | R⁸ |
|---|---|---|---|---|---|---|---|---|
| M-1 | H | H | H | H | H | CH₂CO₂Buᵗ | Et | Et |
| M-2 | Cl | H | H | H | H | CH₂CO₂Buᵗ | Et | Et |
| M-3 | Br | H | H | H | H | CH₂CO₂Buᵗ | Et | Et |
| M-4 | Me | H | H | H | H | CH₂CO₂Buᵗ | Et | Et |
| M-5 | Et | H | H | H | H | CH₂CO₂Buᵗ | Et | Et |
| M-6 | Pr | H | H | H | H | CH₂CO₂Buᵗ | Et | Et |
| M-7 | Bu | H | H | H | H | CH₂CO₂Buᵗ | Et | Et |
| M-8 | Buⁱ | H | H | H | H | CH₂CO₂Buᵗ | Et | Et |
| M-9 | Buᵗ | H | H | H | H | CH₂CO₂Buᵗ | Et | Et |
| M-10 | OMe | H | Et | H | H | CH₂CO₂Buᵗ | Et | Et |
| M-11 | OEt | H | H | H | H | CH₂CO₂Buᵗ | Et | Et |
| M-12 | OPrⁱ | H | H | H | H | CH₂CO₂Buᵗ | Et | Et |
| M-13 | OPr | H | H | H | H | CH₂CO₂Buᵗ | Et | Et |
| M-14 | OCHF₂ | H | H | H | H | CH₂CO₂Buᵗ | Et | Et |
| M-15 | OCF₃ | H | H | H | H | CH₂CO₂Buᵗ | Et | Et |
| M-16 | CF₃ | H | H | H | H | CH₂CO₂Buᵗ | Et | Et |
| M-17 | SMe | H | H | H | H | CH₂CO₂Buᵗ | Et | Et |
| M-18 | SEt | H | H | H | H | CH₂CO₂Buᵗ | Et | Et |
| M-19 | SPrⁱ | H | H | H | H | CH₂CO₂Buᵗ | Et | Et |
| M-20 | OEt | H | Et | H | H | CH₂CO₂Buᵗ | Et | Et |
| M-21 | NEt₂ | H | H | H | H | CH₂CO₂Buᵗ | Et | Et |
| M-22 | H | Cl | H | H | H | CH₂CO₂Buᵗ | Et | Et |
| M-23 | H | Br | H | H | H | CH₂CO₂Buᵗ | Et | Et |
| M-24 | H | Me | H | H | H | CH₂CO₂Buᵗ | Et | Et |
| M-25 | H | Et | H | H | H | CH₂CO₂Buᵗ | Et | Et |

TABLE 59

| | R¹ | R² | R³ | R⁴ | R⁵ | R⁶ | R⁷ | R⁸ |
|---|---|---|---|---|---|---|---|---|
| M-26 | H | Pr | H | H | H | CH₂CO₂Buᵗ | Et | Et |
| M-27 | H | Prⁱ | H | H | H | CH₂CO₂Buᵗ | Et | Et |
| M-28 | H | Bu | H | H | H | CH₂CO₂Buᵗ | Et | Et |
| M-29 | H | Buⁱ | H | H | H | CH₂CO₂Buᵗ | Et | Et |
| M-30 | H | Buˢ | H | H | H | CH₂CO₂Buᵗ | Et | Et |
| M-31 | H | Buᵗ | H | H | H | CH₂CO₂Buᵗ | Et | Et |
| M-32 | H | OMe | H | H | H | CH₂CO₂Buᵗ | Et | Et |
| M-33 | H | OEt | H | H | H | CH₂CO₂Buᵗ | Et | Et |
| M-34 | H | OPr | H | H | H | CH₂CO₂Buᵗ | Et | Et |
| M-35 | H | OPrⁱ | H | H | H | CH₂CO₂Buᵗ | Et | Et |
| M-36 | H | OCHF₂ | H | H | H | CH₂CO₂Buᵗ | Et | Et |
| M-37 | H | OCF₃ | H | H | H | CH₂CO₂Buᵗ | Et | Et |
| M-38 | H | CF₃ | H | H | H | CH₂CO₂Buᵗ | Et | Et |
| M-39 | H | SMe | H | H | H | CH₂CO₂Buᵗ | Et | Et |
| M-40 | H | SEt | H | H | H | CH₂CO₂Buᵗ | Et | Et |
| M-41 | H | SPrⁱ | H | H | H | CH₂CO₂Buᵗ | Et | Et |
| M-42 | OEt | H | Et | H | H | CH₂CO₂Buᵗ | Et | Et |
| M-43 | Prⁱ | H | OMe | H | H | CH₂CO₂Buᵗ | Et | Et |
| M-44 | H | H | Cl | H | H | CH₂CO₂Buᵗ | Et | Et |
| M-45 | H | H | Br | H | H | CH₂CO₂Buᵗ | Et | Et |
| M-46 | H | H | Me | H | H | CH₂CO₂Buᵗ | Et | Et |
| M-47 | H | H | CH₂OMe | H | H | CH₂CO₂Buᵗ | Et | Et |
| M-48 | H | H | Pr | H | H | CH₂CO₂Buᵗ | Et | Et |
| M-49 | OMe | H | Me | H | H | CH₂CO₂Buᵗ | Et | Et |
| M-50 | H | H | Bu | H | H | CH₂CO₂Buᵗ | Et | Et |

TABLE 60

| | R¹ | R² | R³ | R⁴ | R⁵ | R⁶ | R⁷ | R⁸ |
|---|---|---|---|---|---|---|---|---|
| M-51 | H | H | Buⁱ | H | H | CH₂CO₂Buᵗ | Et | Et |
| M-52 | H | H | Buˢ | H | H | CH₂CO₂Buᵗ | Et | Et |
| M-53 | H | H | Buᵗ | H | H | CH₂CO₂Buᵗ | Et | Et |
| M-54 | H | H | OMe | H | H | CH₂CO₂Buᵗ | Et | Et |
| M-55 | H | H | OEt | H | H | CH₂CO₂Buᵗ | Et | Et |
| M-56 | H | H | OPr | H | H | CH₂CO₂Buᵗ | Et | Et |
| M-57 | H | H | OPrⁱ | H | H | CH₂CO₂Buᵗ | Et | Et |
| M-58 | H | H | OCHF₂ | H | H | CH₂CO₂Buᵗ | Et | Et |
| M-59 | Buⁱ | H | H | H | H | CH₂CO₂Buᵗ | Et | Et |
| M-60 | H | H | CF₃ | H | H | CH₂CO₂Buᵗ | Et | Et |
| M-61 | H | H | SMe | H | H | CH₂CO₂Buᵗ | Et | Et |
| M-62 | H | H | SEt | H | H | CH₂CO₂Buᵗ | Et | Et |
| M-63 | H | H | SPrⁱ | H | H | CH₂CO₂Buᵗ | Et | Et |
| M-64 | H | H | NMe₂ | H | H | CH₂CO₂Buᵗ | Et | Et |
| M-65 | H | H | NEt₂ | H | H | CH₂CO₂Buᵗ | Et | Et |
| M-66 | Et | NMe₂ | H | H | H | CH₂CO₂Buᵗ | Et | Et |
| M-67 | NMe₂ | Cl | H | H | H | CH₂CO₂Buᵗ | Et | Et |
| M-68 | Et | NEt₂ | H | H | H | CH₂CO₂Buᵗ | Et | Et |
| M-69 | H | NEt₂ | Me | H | H | CH₂CO₂Buᵗ | Et | Et |
| M-70 | Me | NEt₂ | H | H | H | CH₂CO₂Buᵗ | Et | Et |
| M-71 | OMe | H | OMe | H | H | CH₂CO₂Buᵗ | Et | Et |
| M-72 | H | OMe | OMe | H | H | CH₂CO₂Buᵗ | Et | Et |
| M-73 | H | OMe | OEt | H | H | CH₂CO₂Buᵗ | Et | Et |
| M-74 | H | OEt | OMe | H | H | CH₂CO₂Buᵗ | Et | Et |
| M-75 | H | OEt | OEt | H | H | CH₂CO₂Buᵗ | Et | Et |
| M-76 | —(CH₂)₃— | | H | H | H | CH₂CO₂Buᵗ | Et | Et |
| M-77 | —(CH₂)₄— | | H | H | H | CH₂CO₂Buᵗ | Et | Et |

TABLE 61

| | R¹ | R² | R³ | R⁴ | R⁵ | R⁶ | R⁷ R⁸ |
|---|---|---|---|---|---|---|---|
| N-1 | H | H | H | H | H | CH₂CO₂Buᵗ | —(CH₂)₄— |
| N-2 | Cl | H | H | H | H | CH₂CO₂Buᵗ | —(CH₂)₄— |
| N-3 | Br | H | H | H | H | CH₂CO₂Buᵗ | —(CH₂)₄— |
| N-4 | Me | H | H | H | H | CH₂CO₂Buᵗ | —(CH₂)₄— |
| N-5 | Et | H | H | H | H | CH₂CO₂Buᵗ | —(CH₂)₄— |
| N-6 | Pr | H | H | H | H | CH₂CO₂Buᵗ | —(CH₂)₄— |
| N-7 | Bu | H | H | H | H | CH₂CO₂Buᵗ | —(CH₂)₄— |
| N-8 | Buⁱ | H | H | H | H | CH₂CO₂Buᵗ | —(CH₂)₄— |
| N-9 | Buᵗ | H | H | H | H | CH₂CO₂Buᵗ | —(CH₂)₄— |
| N-10 | OMe | H | Et | H | H | CH₂CO₂Buᵗ | —(CH₂)₄— |
| N-11 | OEt | H | H | H | H | CH₂CO₂Buᵗ | —(CH₂)₄— |
| N-12 | OPrⁱ | H | H | H | H | CH₂CO₂Buᵗ | —(CH₂)₄— |
| N-13 | OPr | H | H | H | H | CH₂CO₂Buᵗ | —(CH₂)₄— |
| N-14 | OCHF₂ | H | H | H | H | CH₂CO₂Buᵗ | —(CH₂)₄— |
| N-15 | OCF₃ | H | H | H | H | CH₂CO₂Buᵗ | —(CH₂)₄— |
| N-16 | CF₃ | H | H | H | H | CH₂CO₂Buᵗ | —(CH₂)₄— |
| N-17 | SMe | H | H | H | H | CH₂CO₂Buᵗ | —(CH₂)₄— |
| N-18 | SEt | H | H | H | H | CH₂CO₂Buᵗ | —(CH₂)₄— |
| N-19 | SPrⁱ | H | H | H | H | CH₂CO₂Buᵗ | —(CH₂)₄— |
| N-20 | OEt | H | Et | H | H | CH₂CO₂Buᵗ | —(CH₂)₄— |
| N-21 | NEt₂ | H | H | H | H | CH₂CO₂Buᵗ | —(CH₂)₄— |
| N-22 | H | Cl | H | H | H | CH₂CO₂Buᵗ | —(CH₂)₄— |
| N-23 | H | Br | H | H | H | CH₂CO₂Buᵗ | —(CH₂)₄— |
| N-24 | H | Me | H | H | H | CH₂CO₂Buᵗ | —(CH₂)₄— |
| N-25 | H | Et | H | H | H | CH₂CO₂Buᵗ | —(CH₂)₄— |

TABLE 62

| | R¹ | R² | R³ | R⁴ | R⁵ | R⁶ | R⁷ R⁸ |
|---|---|---|---|---|---|---|---|
| N-26 | H | Pr | H | H | H | CH₂CO₂Buᵗ | —(CH₂)₄— |
| N-27 | H | Prⁱ | H | H | H | CH₂CO₂Buᵗ | —(CH₂)₄— |
| N-28 | H | Bu | H | H | H | CH₂CO₂Buᵗ | —(CH₂)₄— |
| N-29 | H | Buⁱ | H | H | H | CH₂CO₂Buᵗ | —(CH₂)₄— |
| N-30 | H | Buˢ | H | H | H | CH₂CO₂Buᵗ | —(CH₂)₄— |
| N-31 | H | Buᵗ | H | H | H | CH₂CO₂Buᵗ | —(CH₂)₄— |
| N-32 | H | OMe | H | H | H | CH₂CO₂Buᵗ | —(CH₂)₄— |
| N-33 | H | OEt | H | H | H | CH₂CO₂Buᵗ | —(CH₂)₄— |
| N-34 | H | OPr | H | H | H | CH₂CO₂Buᵗ | —(CH₂)₄— |
| N-35 | H | OPrⁱ | H | H | H | CH₂CO₂Buᵗ | —(CH₂)₄— |
| N-36 | H | OCHF₂ | H | H | H | CH₂CO₂Buᵗ | —(CH₂)₄— |
| N-37 | H | OCF₃ | H | H | H | CH₂CO₂Buᵗ | —(CH₂)₄— |
| N-38 | H | CF₃ | H | H | H | CH₂CO₂Buᵗ | —(CH₂)₄— |
| N-39 | H | SMe | H | H | H | CH₂CO₂Buᵗ | —(CH₂)₄— |
| N-40 | H | SEt | H | H | H | CH₂CO₂Buᵗ | —(CH₂)₄— |
| N-41 | H | SPrⁱ | H | H | H | CH₂CO₂Buᵗ | —(CH₂)₄— |
| N-42 | H | NMe₂ | H | H | H | CH₂CO₂Buᵗ | —(CH₂)₄— |
| N-43 | H | NEt₂ | H | H | H | CH₂CO₂Buᵗ | —(CH₂)₄— |
| N-44 | H | H | Cl | H | H | CH₂CO₂Buᵗ | —(CH₂)₄— |
| N-45 | H | H | Br | H | H | CH₂CO₂Buᵗ | —(CH₂)₄— |
| N-46 | H | H | Me | H | H | CH₂CO₂Buᵗ | —(CH₂)₄— |
| N-47 | H | OMe | Et | H | H | CH₂CO₂Buᵗ | —(CH₂)₄— |
| N-48 | H | H | Pr | H | H | CH₂CO₂Buᵗ | —(CH₂)₄— |
| N-49 | OMe | H | Me | H | H | CH₂CO₂Buᵗ | —(CH₂)₄— |
| N-50 | H | H | Bu | H | H | CH₂CO₂Buᵗ | —(CH₂)₄— |

TABLE 63

|  | R¹ | R² | R³ | R⁴ | R⁵ | R⁶ | R⁷ R⁸ |
|---|---|---|---|---|---|---|---|
| N-51 | H | H | Buⁱ | H | H | CH₂CO₂Buᵗ | —(CH₂)₄— |
| N-52 | H | H | Buˢ | H | H | CH₂CO₂Buᵗ | —(CH₂)₄— |
| N-53 | H | H | Buᵗ | H | H | CH₂CO₂Buᵗ | —(CH₂)₄— |
| N-54 | H | H | OMe | H | H | CH₂CO₂Buᵗ | —(CH₂)₄— |
| N-55 | H | H | OEt | H | H | CH₂CO₂Buᵗ | —(CH₂)₄— |
| N-56 | H | H | OPr | H | H | CH₂CO₂Buᵗ | —(CH₂)₄— |
| N-57 | H | H | OPrⁱ | H | H | CH₂CO₂Buᵗ | —(CH₂)₄— |
| N-58 | H | H | OCHF₂ | H | H | CH₂CO₂Buᵗ | —(CH₂)₄— |
| N-59 | Et | NMe₂ | H | H | H | CH₂CO₂Buᵗ | —(CH₂)₄— |
| N-60 | H | H | CF₃ | H | H | CH₂CO₂Buᵗ | —(CH₂)₄— |
| N-61 | H | H | SMe | H | H | CH₂CO₂Buᵗ | —(CH₂)₄— |
| N-62 | H | H | SEt | H | H | CH₂CO₂Buᵗ | —(CH₂)₄— |
| N-63 | H | H | SPrⁱ | H | H | CH₂CO₂Buᵗ | —(CH₂)₄— |
| N-64 | H | H | NMe₂ | H | H | CH₂CO₂Buᵗ | —(CH₂)₄— |
| N-65 | H | H | NEt₂ | H | H | CH₂CO₂Buᵗ | —(CH₂)₄— |
| N-66 | Me | NMe₂ | H | H | H | CH₂CO₂Buᵗ | —(CH₂)₄— |
| N-67 | NMe₂ | Cl | H | H | H | CH₂CO₂Buᵗ | —(CH₂)₄— |
| N-68 | Me | NEt₂ | H | H | H | CH₂CO₂Buᵗ | —(CH₂)₄— |
| N-69 | H | NEt₂ | Me | H | H | CH₂CO₂Buᵗ | —(CH₂)₄— |
| N-70 | Buˢ | H | H | H | H | CH₂CO₂Buᵗ | —(CH₂)₄— |
| N-71 | Et | NEt₂ | H | H | H | CH₂CO₂Buᵗ | —(CH₂)₄— |
| N-72 | H | OMe | OMe | H | H | CH₂CO₂Buᵗ | —(CH₂)₄— |
| N-73 | H | OMe | OEt | H | H | CH₂CO₂Buᵗ | —(CH₂)₄— |
| N-74 | H | OEt | OMe | H | H | CH₂CO₂Buᵗ | —(CH₂)₄— |
| N-75 | H | OEt | OEt | H | H | CH₂CO₂Buᵗ | —(CH₂)₄— |
| N-76 | —(CH₂)₃— | | H | H | H | CH₂CO₂Buᵗ | —(CH₂)₄— |
| N-77 | —(CH₂)₄— | | H | H | H | CH₂CO₂Buᵗ | —(CH₂)₄— |

TABLE 64

|  | R¹ | R² | R³ | R⁴ | R⁵ | R⁶ | R⁷ R⁸ |
|---|---|---|---|---|---|---|---|
| O-1 | H | H | H | H | H | CH₂CO₂Buᵗ | —(CH₂)₅— |
| O-2 | Cl | H | H | H | H | CH₂CO₂Buᵗ | —(CH₂)₅— |
| O-3 | Br | H | H | H | H | CH₂CO₂Buᵗ | —(CH₂)₅— |
| O-4 | Me | H | H | H | H | CH₂CO₂Buᵗ | —(CH₂)₅— |
| O-5 | Et | H | H | H | H | CH₂CO₂Buᵗ | —(CH₂)₅— |
| O-6 | Pr | H | H | H | H | CH₂CO₂Buᵗ | —(CH₂)₅— |
| O-7 | Bu | H | H | H | H | CH₂CO₂Buᵗ | —(CH₂)₅— |
| O-8 | Buⁱ | H | H | H | H | CH₂CO₂Buᵗ | —(CH₂)₅— |
| O-9 | Buᵗ | H | H | H | H | CH₂CO₂Buᵗ | —(CH₂)₅— |
| O-10 | OMe | H | Et | H | H | CH₂CO₂Buᵗ | —(CH₂)₅— |
| O-11 | OEt | H | H | H | H | CH₂CO₂Buᵗ | —(CH₂)₅— |
| O-12 | OPrⁱ | H | H | H | H | CH₂CO₂Buᵗ | —(CH₂)₅— |
| O-13 | OPr | H | H | Et | H | CH₂CO₂Buᵗ | —(CH₂)₅— |
| O-14 | OCHF₂ | H | H | H | H | CH₂CO₂Buᵗ | —(CH₂)₅— |
| O-15 | OCF₃ | H | H | H | H | CH₂CO₂Buᵗ | —(CH₂)₅— |
| O-16 | CF₃ | H | H | H | H | CH₂CO₂Buᵗ | —(CH₂)₅— |
| O-17 | SMe | H | H | H | H | CH₂CO₂Buᵗ | —(CH₂)₅— |
| O-18 | SEt | H | H | H | H | CH₂CO₂Buᵗ | —(CH₂)₅— |
| O-19 | SPrⁱ | H | H | H | H | CH₂CO₂Buᵗ | —(CH₂)₅— |
| O-20 | OEt | H | Et | H | H | CH₂CO₂Buᵗ | —(CH₂)₅— |
| O-21 | NEt₂ | H | H | H | H | CH₂CO₂Buᵗ | —(CH₂)₅— |
| O-22 | H | Cl | H | H | H | CH₂CO₂Buᵗ | —(CH₂)₅— |
| O-23 | H | Br | H | H | H | CH₂CO₂Buᵗ | —(CH₂)₅— |
| O-24 | H | Me | H | H | H | CH₂CO₂Buᵗ | —(CH₂)₅— |
| O-25 | H | Et | H | H | H | CH₂CO₂Buᵗ | —(CH₂)₅— |

TABLE 65

|  | R¹ | R² | R³ | R⁴ | R⁵ | R⁶ | R⁷ R⁸ |
|---|---|---|---|---|---|---|---|
| O-26 | H | Pr | H | H | H | CH₂CO₂Buᵗ | —(CH₂)₅— |
| O-27 | H | Prⁱ | H | H | H | CH₂CO₂Buᵗ | —(CH₂)₅— |
| O-28 | H | Bu | H | H | H | CH₂CO₂Buᵗ | —(CH₂)₅— |
| O-29 | H | Buⁱ | H | H | H | CH₂CO₂Buᵗ | —(CH₂)₅— |
| O-30 | H | Buˢ | H | H | H | CH₂CO₂Buᵗ | —(CH₂)₅— |
| O-31 | H | Buᵗ | H | H | H | CH₂CO₂Buᵗ | —(CH₂)₅— |
| O-32 | H | OMe | H | H | H | CH₂CO₂Buᵗ | —(CH₂)₅— |
| O-33 | H | OEt | H | H | H | CH₂CO₂Buᵗ | —(CH₂)₅— |
| O-34 | H | OPr | H | H | H | CH₂CO₂Buᵗ | —(CH₂)₅— |
| O-35 | H | OPrⁱ | H | H | H | CH₂CO₂Buᵗ | —(CH₂)₅— |
| O-36 | H | OCHF₂ | H | H | H | CH₂CO₂Buᵗ | —(CH₂)₅— |
| O-37 | H | OCF₃ | H | H | H | CH₂CO₂Buᵗ | —(CH₂)₅— |
| O-38 | H | CF₃ | H | H | H | CH₂CO₂Buᵗ | —(CH₂)₅— |
| O-39 | H | SMe | H | H | H | CH₂CO₂Buᵗ | —(CH₂)₅— |
| O-40 | H | SEt | H | H | H | CH₂CO₂Buᵗ | —(CH₂)₅— |
| O-41 | H | SPrⁱ | H | H | H | CH₂CO₂Buᵗ | —(CH₂)₅— |
| O-42 | H | NMe₂ | H | H | H | CH₂CO₂Buᵗ | —(CH₂)₅— |
| O-43 | H | NEt₂ | H | H | H | CH₂CO₂Buᵗ | —(CH₂)₅— |
| O-44 | H | H | Cl | H | H | CH₂CO₂Buᵗ | —(CH₂)₅— |
| O-45 | H | H | Br | H | H | CH₂CO₂Buᵗ | —(CH₂)₅— |
| O-46 | H | H | Me | H | H | CH₂CO₂Buᵗ | —(CH₂)₅— |
| O-47 | H | OMe | Et | H | H | CH₂CO₂Buᵗ | —(CH₂)₅— |
| O-48 | H | H | Pr | H | H | CH₂CO₂Buᵗ | —(CH₂)₅— |
| O-49 | H | H | Prⁱ | H | H | CH₂CO₂Buᵗ | —(CH₂)₅— |
| O-50 | H | H | Bu | H | H | CH₂CO₂Buᵗ | —(CH₂)₅— |

TABLE 66

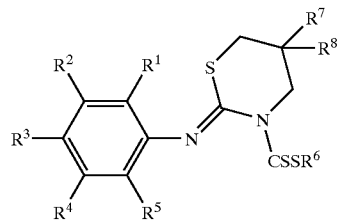

| | R¹ | R² | R³ | R⁴ | R⁵ | R⁶ | R⁷ | R⁸ |
|---|---|---|---|---|---|---|---|---|
| O-51 | H | H | Buⁱ | H | H | CH₂CO₂Buᵗ | —(CH₂)₅— | |
| O-52 | H | H | Buˢ | H | H | CH₂CO₂Buᵗ | —(CH₂)₅— | |
| O-53 | H | H | Buᵗ | H | H | CH₂CO₂Buᵗ | —(CH₂)₅— | |
| O-54 | H | H | OMe | H | H | CH₂CO₂Buᵗ | —(CH₂)₅— | |
| O-55 | H | H | OEt | H | H | CH₂CO₂Buᵗ | —(CH₂)₅— | |
| O-56 | H | H | OPr | H | H | CH₂CO₂Buᵗ | —(CH₂)₅— | |
| O-57 | H | H | OPrⁱ | H | H | CH₂CO₂Buᵗ | —(CH₂)₅— | |
| O-58 | H | H | OCHF₂ | H | H | CH₂CO₂Buᵗ | —(CH₂)₅— | |
| O-59 | Et | NMe₂ | H | H | H | CH₂CO₂Buᵗ | —(CH₂)₅— | |
| O-60 | H | H | CF₃ | H | H | CH₂CO₂Buᵗ | —(CH₂)₅— | |
| O-61 | H | H | SMe | H | H | CH₂CO₂Buᵗ | —(CH₂)₅— | |
| O-62 | H | H | SEt | H | H | CH₂CO₂Buᵗ | —(CH₂)₅— | |
| O-63 | H | H | SPrⁱ | H | H | CH₂CO₂Buᵗ | —(CH₂)₅— | |
| O-64 | H | H | NMe₂ | H | H | CH₂CO₂Buᵗ | —(CH₂)₅— | |
| O-65 | H | H | NEt₂ | H | H | CH₂CO₂Buᵗ | —(CH₂)₅— | |
| O-66 | Me | NMe₂ | H | H | H | CH₂CO₂Buᵗ | —(CH₂)₅— | |
| O-67 | NMe₂ | Cl | H | H | H | CH₂CO₂Buᵗ | —(CH₂)₅— | |
| O-68 | Me | NEt₂ | H | H | H | CH₂CO₂Buᵗ | —(CH₂)₅— | |
| O-69 | H | NEt₂ | Me | H | H | CH₂CO₂Buᵗ | —(CH₂)₅— | |
| O-70 | Buˢ | H | H | H | H | CH₂CO₂Buᵗ | —(CH₂)₅— | |
| O-71 | Et | NEt₂ | H | H | H | CH₂CO₂Buᵗ | —(CH₂)₅— | |
| O-72 | H | OMe | OMe | H | H | CH₂CO₂Buᵗ | —(CH₂)₅— | |
| O-73 | H | OMe | OEt | H | H | CH₂CO₂Buᵗ | —(CH₂)₅— | |
| O-74 | H | OEt | OMe | H | H | CH₂CO₂Buᵗ | —(CH₂)₅— | |
| O-75 | H | OEt | OEt | H | H | CH₂CO₂Buᵗ | —(CH₂)₅— | |
| O-76 | —(CH₂)₃— | | H | H | H | CH₂CO₂Buᵗ | —(CH₂)₅— | |
| O-77 | —(CH₂)₄— | | H | H | H | CH₂CO₂Buᵗ | —(CH₂)₅— | |

TABLE 67

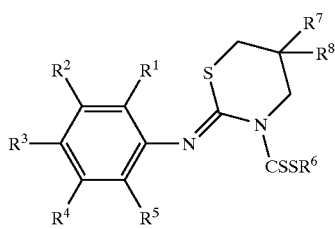

| | R¹ | R² | R³ | R⁴ | R⁵ | R⁶ | R⁷ | R⁸ |
|---|---|---|---|---|---|---|---|---|
| P-1 | H | H | H | H | H | (3-Me-5-isoxazolyl)methyl | Me | Me |
| P-2 | Cl | H | H | H | H | (3-Me-5-isoxazolyl)methyl | Me | Me |
| P-3 | Br | H | H | H | H | (3-Me-5-isoxazolyl)methyl | Me | Me |
| P-4 | Me | H | H | H | H | (3-Me-5-isoxazolyl)methyl | Me | Me |
| P-5 | Et | H | H | H | H | (3-Me-5-isoxazolyl)methyl | Me | Me |
| P-6 | Pr | H | H | H | H | (3-Me-5-isoxazolyl)methyl | Me | Me |
| P-7 | Bu | H | H | H | H | (3-Me-5-isoxazolyl)methyl | Me | Me |
| P-8 | Buⁱ | H | H | H | H | (3-Me-5-isoxazolyl)methyl | Me | Me |
| P-9 | Buᵗ | H | H | H | H | (3-Me-5-isoxazolyl)methyl | Me | Me |
| P-10 | OMe | H | H | H | H | (3-Me-5-isoxazolyl)methyl | Me | Me |
| P-11 | OEt | H | H | H | H | (3-Me-5-isoxazolyl)methyl | Me | Me |
| P-12 | OPrⁱ | H | H | H | H | (3-Me-5-isoxazolyl)methyl | Me | Me |
| P-13 | OPr | H | H | H | H | (3-Me-5-isoxazolyl)methyl | Me | Me |
| P-14 | OCHF₂ | H | H | H | H | (3-Me-5-isoxazolyl)methyl | Me | Me |
| P-15 | OCF₃ | H | H | H | H | (3-Me-5-isoxazolyl)methyl | Me | Me |

TABLE 67-continued

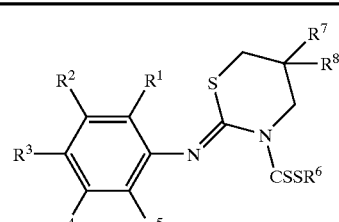

| | R¹ | R² | R³ | R⁴ | R⁵ | R⁶ | R⁷ | R⁸ |
|---|---|---|---|---|---|---|---|---|
| P-16 | CF₃ | H | H | H | H | (3-Me-5-isoxazolyl)methyl | Me | Me |
| P-17 | SMe | H | H | H | H | (3-Me-5-isoxazolyl)methyl | Me | Me |
| P-18 | SEt | H | H | H | H | (3-Me-5-isoxazolyl)methyl | Me | Me |
| P-19 | SPrⁱ | H | H | H | H | (3-Me-5-isoxazolyl)methyl | Me | Me |
| P-20 | NMe₂ | H | H | H | H | (3-Me-5-isoxazolyl)methyl | Me | Me |
| P-21 | NEt₂ | H | H | H | H | (3-Me-5-isoxazolyl)methyl | Me | Me |
| P-22 | H | Cl | H | H | H | (3-Me-5-isoxazolyl)methyl | Me | Me |
| P-23 | H | Br | H | H | H | (3-Me-5-isoxazolyl)methyl | Me | Me |
| P-24 | H | Me | H | H | H | (3-Me-5-isoxazolyl)methyl | Me | Me |
| P-25 | H | Et | H | H | H | (3-Me-5-isoxazolyl)methyl | Me | Me |

TABLE 68

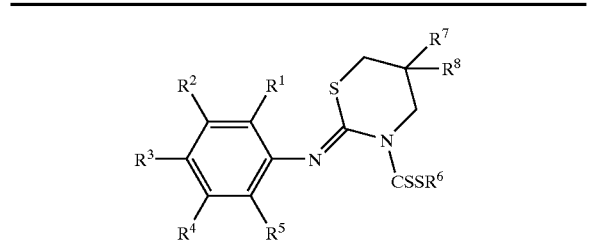

| | R¹ | R² | R³ | R⁴ | R⁵ | R⁶ | R⁷ | R⁸ |
|---|---|---|---|---|---|---|---|---|
| P-26 | H | Pr | H | H | H | (3-Me-5-isoxazolyl)methyl | Me | Me |
| P-27 | H | Pr$^i$ | H | H | H | (3-Me-5-isoxazolyl)methyl | Me | Me |
| P-28 | H | Bu | H | H | H | (3-Me-5-isoxazolyl)methyl | Me | Me |
| P-29 | H | Bu$^i$ | H | H | H | (3-Me-5-isoxazolyl)methyl | Me | Me |
| P-30 | H | Bu$^s$ | H | H | H | (3-Me-5-isoxazolyl)methyl | Me | Me |
| P-31 | H | Bu$^t$ | H | H | H | (3-Me-5-isoxazolyl)methyl | Me | Me |
| P-32 | H | OMe | H | H | H | (3-Me-5-isoxazolyl)methyl | Me | Me |
| P-33 | H | OEt | H | H | H | (3-Me-5-isoxazolyl)methyl | Me | Me |
| P-34 | H | OPr | H | H | H | (3-Me-5-isoxazolyl)methyl | Me | Me |
| P-35 | H | OPr$^i$ | H | H | H | (3-Me-5-isoxazolyl)methyl | Me | Me |
| P-36 | H | OCHF$_2$ | H | H | H | (3-Me-5-isoxazolyl)methyl | Me | Me |
| P-37 | H | OCF$_3$ | H | H | H | (3-Me-5-isoxazolyl)methyl | Me | Me |
| P-38 | H | CF$_3$ | H | H | H | (3-Me-5-isoxazolyl)methyl | Me | Me |
| P-39 | H | SMe | H | H | H | (3-Me-5-isoxazolyl)methyl | Me | Me |
| P-40 | H | SEt | H | H | H | (3-Me-5-isoxazolyl)methyl | Me | Me |
| P-41 | H | SPr$^i$ | H | H | H | (3-Me-5-isoxazolyl)methyl | Me | Me |
| P-42 | H | NMe$_2$ | H | H | H | (3-Me-5-isoxazolyl)methyl | Me | Me |
| P-43 | H | NEt$_2$ | H | H | H | (3-Me-5-isoxazolyl)methyl | Me | Me |
| P-44 | H | H | Cl | H | H | (3-Me-5-isoxazolyl)methyl | Me | Me |
| P-45 | H | H | Br | H | H | (3-Me-5-isoxazolyl)methyl | Me | Me |
| P-46 | H | H | Me | H | H | (3-Me-5-isoxazolyl)methyl | Me | Me |
| P-47 | H | H | Et | H | H | (3-Me-5-isoxazolyl)methyl | Me | Me |
| P-48 | H | H | Pr | H | H | (3-Me-5-isoxazolyl)methyl | Me | Me |
| P-49 | H | H | Pr$^i$ | H | H | (3-Me-5-isoxazolyl)methyl | Me | Me |
| P-50 | H | H | Bu | H | H | (3-Me-5-isoxazolyl)methyl | Me | Me |

TABLE 69

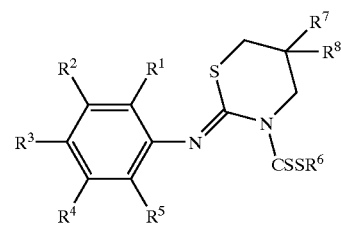

| | R¹ | R² | R³ | R⁴ | R⁵ | R⁶ | R⁷ | R⁸ |
|---|---|---|---|---|---|---|---|---|
| P-51 | H | H | Bu$^i$ | H | H | (3-Me-5-isoxazolyl)methyl | Me | Me |
| P-52 | H | H | Bu$^s$ | H | H | (3-Me-5-isoxazolyl)methyl | Me | Me |
| P-53 | H | H | Bu$^t$ | H | H | (3-Me-5-isoxazolyl)methyl | Me | Me |
| P-54 | H | H | OMe | H | H | (3-Me-5-isoxazolyl)methyl | Me | Me |
| P-55 | H | H | OEt | H | H | (3-Me-5-isoxazolyl)methyl | Me | Me |
| P-56 | H | H | OPr | H | H | (3-Me-5-isoxazolyl)methyl | Me | Me |
| P-57 | H | H | OPr$^i$ | H | H | (3-Me-5-isoxazolyl)methyl | Me | Me |
| P-58 | H | H | OCHF$_2$ | H | H | (3-Me-5-isoxazolyl)methyl | Me | Me |
| P-59 | H | H | OCF$_3$ | H | H | (3-Me-5-isoxazolyl)methyl | Me | Me |
| P-60 | H | H | CF$_3$ | H | H | (3-Me-5-isoxazolyl)methyl | Me | Me |
| P-61 | H | H | SMe | H | H | (3-Me-5-isoxazolyl)methyl | Me | Me |
| P-62 | H | H | SEt | H | H | (3-Me-5-isoxazolyl)methyl | Me | Me |
| P-63 | H | H | SPr$^i$ | H | H | (3-Me-5-isoxazolyl)methyl | Me | Me |
| P-64 | H | H | NMe$_2$ | H | H | (3-Me-5-isoxazolyl)methyl | Me | Me |
| P-65 | H | H | NEt$_2$ | H | H | (3-Me-5-isoxazolyl)methyl | Me | Me |
| P-66 | Et | NMe$_2$ | H | H | H | (3-Me-5-isoxazolyl)methyl | Me | Me |
| P-67 | NMe$_2$ | Cl | H | H | H | (3-Me-5-isoxazolyl)methyl | Me | Me |
| P-68 | Et | NEt$_2$ | H | H | H | (3-Me-5-isoxazolyl)methyl | Me | Me |
| P-69 | H | NEt$_2$ | Me | H | H | (3-Me-5-isoxazolyl)methyl | Me | Me |
| P-70 | Bu$^s$ | H | H | H | H | (3-Me-5-isoxazolyl)methyl | Me | Me |
| P-71 | OMe | H | OMe | H | H | (3-Me-5-isoxazolyl)methyl | Me | Me |
| P-72 | H | OMe | OMe | H | H | (3-Me-5-isoxazolyl)methyl | Me | Me |
| P-73 | H | OMe | OEt | H | H | (3-Me-5-isoxazolyl)methyl | Me | Me |

TABLE 69-continued

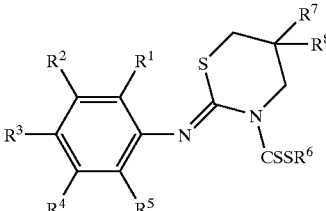

| | R¹ | R² | R³ | R⁴ | R⁵ | R⁶ | R⁷ | R⁸ |
|---|---|---|---|---|---|---|---|---|
| P-74 | H | OEt | OMe | H | H | (3-Me-5-isoxazolyl)methyl | Me | Me |
| P-75 | H | OEt | OEt | H | H | (3-Me-5-isoxazolyl)methyl | Me | Me |

TABLE 70

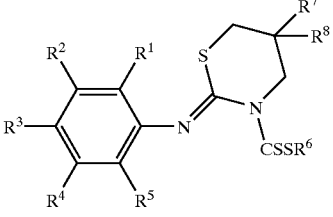

| | R¹ | R² | R³ | R⁴ | R⁵ | R⁶ | R⁷ | R⁸ |
|---|---|---|---|---|---|---|---|---|
| Q-1 | H | H | H | H | H | (3-Me-5-isoxazolyl)methyl | Et | Et |
| Q-2 | Cl | H | H | H | H | (3-Me-5-isoxazolyl)methyl | Et | Et |
| Q-3 | Br | H | H | H | H | (3-Me-5-isoxazolyl)methyl | Et | Et |
| Q-4 | Me | H | H | H | H | (3-Me-5-isoxazolyl)methyl | Et | Et |
| Q-5 | Et | H | H | H | H | (3-Me-5-isoxazolyl)methyl | Et | Et |
| Q-6 | Pr | H | H | H | H | (3-Me-5-isoxazolyl)methyl | Et | Et |
| Q-7 | Bu | H | H | H | H | (3-Me-5-isoxazolyl)methyl | Et | Et |
| Q-8 | Buⁱ | H | H | H | H | (3-Me-5-isoxazolyl)methyl | Et | Et |
| Q-9 | Buᵗ | H | H | H | H | (3-Me-5-isoxazolyl)methyl | Et | Et |
| Q-10 | OMe | H | H | H | H | (3-Me-5-isoxazolyl)methyl | Et | Et |
| Q-11 | OEt | H | H | H | H | (3-Me-5-isoxazolyl)methyl | Et | Et |
| Q-12 | OPrⁱ | H | H | H | H | (3-Me-5-isoxazolyl)methyl | Et | Et |
| Q-13 | OPr | H | H | H | H | (3-Me-5-isoxazolyl)methyl | Et | Et |
| Q-14 | OCHF₂ | H | H | H | H | (3-Me-5-isoxazolyl)methyl | Et | Et |
| Q-15 | OCF₃ | H | H | H | H | (3-Me-5-isoxazolyl)methyl | Et | Et |
| Q-16 | CF₃ | H | H | H | H | (3-Me-5-isoxazolyl)methyl | Et | Et |
| Q-17 | SMe | H | H | H | H | (3-Me-5-isoxazolyl)methyl | Et | Et |
| Q-18 | SEt | H | H | H | H | (3-Me-5-isoxazolyl)methyl | Et | Et |
| Q-19 | SPrⁱ | H | H | H | H | (3-Me-5-isoxazolyl)methyl | Et | Et |
| Q-20 | NMe₂ | H | H | H | H | (3-Me-5-isoxazolyl)methyl | Et | Et |
| Q-21 | NEt₂ | H | H | H | H | (3-Me-5-isoxazolyl)methyl | Et | Et |
| Q-22 | H | Cl | H | H | H | (3-Me-5-isoxazolyl)methyl | Et | Et |
| Q-23 | H | Br | H | H | H | (3-Me-5-isoxazolyl)methyl | Et | Et |
| Q-24 | H | Me | H | H | H | (3-Me-5-isoxazolyl)methyl | Et | Et |
| Q-25 | H | Et | H | H | H | (3-Me-5-isoxazolyl)methyl | Et | Et |

TABLE 71

| | R¹ | R² | R³ | R⁴ | R⁵ | R⁶ | R⁷ | R⁸ |
|---|---|---|---|---|---|---|---|---|
| Q-26 | H | Pr | H | H | H | (3-Me-5-isoxazolyl)methyl | Et | Et |
| Q-27 | H | Prⁱ | H | H | H | (3-Me-5-isoxazolyl)methyl | Et | Et |
| Q-28 | H | Bu | H | H | H | (3-Me-5-isoxazolyl)methyl | Et | Et |
| Q-29 | H | Buⁱ | H | H | H | (3-Me-5-isoxazolyl)methyl | Et | Et |
| Q-30 | H | Buˢ | H | H | H | (3-Me-5-isoxazolyl)methyl | Et | Et |
| Q-31 | H | Buᵗ | H | H | H | (3-Me-5-isoxazolyl)methyl | Et | Et |
| Q-32 | H | OMe | H | H | H | (3-Me-5-isoxazolyl)methyl | Et | Et |
| Q-33 | H | OEt | H | H | H | (3-Me-5-isoxazolyl)methyl | Et | Et |
| Q-34 | H | OPr | H | H | H | (3-Me-5-isoxazolyl)methyl | Et | Et |
| Q-35 | H | OPrⁱ | H | H | H | (3-Me-5-isoxazolyl)methyl | Et | Et |
| Q-36 | H | OCHF₂ | H | H | H | (3-Me-5-isoxazolyl)methyl | Et | Et |
| Q-37 | H | OCF₃ | H | H | H | (3-Me-5-isoxazolyl)methyl | Et | Et |
| Q-38 | H | CF₃ | H | H | H | (3-Me-5-isoxazolyl)methyl | Et | Et |
| Q-39 | H | SMe | H | H | H | (3-Me-5-isoxazolyl)methyl | Et | Et |
| Q-40 | H | SEt | H | H | H | (3-Me-5-isoxazolyl)methyl | Et | Et |
| Q-41 | H | SPrⁱ | H | H | H | (3-Me-5-isoxazolyl)methyl | Et | Et |
| Q-42 | H | NMe₂ | H | H | H | (3-Me-5-isoxazolyl)methyl | Et | Et |
| Q-43 | H | NEt₂ | H | H | H | (3-Me-5-isoxazolyl)methyl | Et | Et |
| Q-44 | H | H | Cl | H | H | (3-Me-5-isoxazolyl)methyl | Et | Et |
| Q-45 | H | H | Br | H | H | (3-Me-5-isoxazolyl)methyl | Et | Et |
| Q-46 | H | H | Me | H | H | (3-Me-5-isoxazolyl)methyl | Et | Et |
| Q-47 | H | H | Et | H | H | (3-Me-5-isoxazolyl)methyl | Et | Et |
| Q-48 | H | H | Pr | H | H | (3-Me-5-isoxazolyl)methyl | Et | Et |
| Q-49 | H | H | Prⁱ | H | H | (3-Me-5-isoxazolyl)methyl | Et | Et |
| Q-50 | H | H | Bu | H | H | (3-Me-5-isoxazolyl)methyl | Et | Et |

TABLE 72

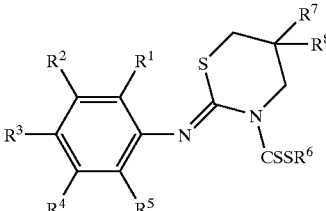

| | $R^1$ | $R^2$ | $R^3$ | $R^4$ | $R^5$ | $R^6$ | $R^7$ | $R^8$ |
|---|---|---|---|---|---|---|---|---|
| Q-51 | H | H | $Bu^i$ | H | H | (3-Me-5-isoxazolyl)methyl | Et | Et |
| Q-52 | H | H | $Bu^s$ | H | H | (3-Me-5-isoxazolyl)methyl | Et | Et |
| Q-53 | H | H | $Bu^t$ | H | H | (3-Me-5-isoxazolyl)methyl | Et | Et |
| Q-54 | H | H | OMe | H | H | (3-Me-5-isoxazolyl)methyl | Et | Et |
| Q-55 | H | H | OEt | H | H | (3-Me-5-isoxazolyl)methyl | Et | Et |
| Q-56 | H | H | OPr | H | H | (3-Me-5-isoxazolyl)methyl | Et | Et |
| Q-57 | H | H | $OPr^i$ | H | H | (3-Me-5-isoxazolyl)methyl | Et | Et |
| Q-58 | H | H | $OCHF_2$ | H | H | (3-Me-5-isoxazolyl)methyl | Et | Et |
| Q-59 | H | H | $OCF_3$ | H | H | (3-Me-5-isoxazolyl)methyl | Et | Et |
| Q-60 | H | H | $CF_3$ | H | H | (3-Me-5-isoxazolyl)methyl | Et | Et |
| Q-61 | H | H | SMe | H | H | (3-Me-5-isoxazolyl)methyl | Et | Et |
| Q-62 | H | H | SEt | H | H | (3-Me-5-isoxazolyl)methyl | Et | Et |
| Q-63 | H | H | $SPr^i$ | H | H | (3-Me-5-isoxazolyl)methyl | Et | Et |
| Q-64 | H | H | $NMe_2$ | H | H | (3-Me-5-isoxazolyl)methyl | Et | Et |
| Q-65 | H | H | $NEt_2$ | H | H | (3-Me-5-isoxazolyl)methyl | Et | Et |
| Q-66 | Et | $NMe_2$ | H | H | H | (3-Me-5-isoxazolyl)methyl | Et | Et |
| Q-67 | $NMe_2$ | Cl | H | H | H | (3-Me-5-isoxazolyl)methyl | Et | Et |
| Q-68 | Et | $NEt_2$ | H | H | H | (3-Me-5-isoxazolyl)methyl | Et | Et |
| Q-69 | H | $NEt_2$ | Me | H | H | (3-Me-5-isoxazolyl)methyl | Et | Et |
| Q-70 | $Bu^s$ | H | H | H | H | (3-Me-5-isoxazolyl)methyl | Et | Et |
| Q-71 | OMe | H | H | H | H | (3-Me-5-isoxazolyl)methyl | Et | Et |
| Q-72 | H | OMe | OMe | H | H | (3-Me-5-isoxazolyl)methyl | Et | Et |
| Q-73 | H | OMe | OEt | H | H | (3-Me-5-isoxazolyl)methyl | Et | Et |
| Q-74 | H | OEt | OMe | H | H | (3-Me-5-isoxazolyl)methyl | Et | Et |
| Q-75 | H | OEt | OEt | H | H | (3-Me-5-isoxazolyl)methyl | Et | Et |
| Q-76 | —$(CH_2)_3$— | | H | H | H | (3-Me-5-isoxazolyl)methyl | Et | Et |
| Q-77 | —$(CH_2)_4$— | | H | H | H | (3-Me-5-isoxazolyl)methyl | Et | Et |

TABLE 73

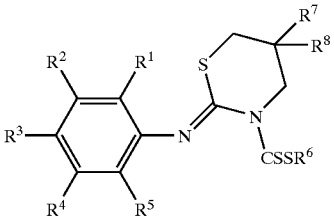

| | $R^1$ | $R^2$ | $R^3$ | $R^4$ | $R^5$ | $R^6$ | $R^7$ $R^8$ |
|---|---|---|---|---|---|---|---|
| R-1 | H | H | H | H | H | (3-Me-5-isoxazolyl)methyl | —$(CH_2)_4$— |
| R-2 | Cl | H | H | H | H | (3-Me-5-isoxazolyl)methyl | —$(CH_2)_4$— |
| R-3 | Br | H | H | H | H | (3-Me-5-isoxazolyl)methyl | —$(CH_2)_4$— |
| R-4 | Me | H | H | H | H | (3-Me-5-isoxazolyl)methyl | —$(CH_2)_4$— |
| R-5 | Et | H | H | H | H | (3-Me-5-isoxazolyl)methyl | —$(CH_2)_4$— |
| R-6 | Pr | H | H | H | H | (3-Me-5-isoxazolyl)methyl | —$(CH_2)_4$— |
| R-7 | Bu | H | H | H | H | (3-Me-5-isoxazolyl)methyl | —$(CH_2)_4$— |
| R-8 | $Bu^i$ | H | H | H | H | (3-Me-5-isoxazolyl)methyl | —$(CH_2)_4$— |
| R-9 | $Bu^t$ | H | H | H | H | (3-Me-5-isoxazolyl)methyl | —$(CH_2)_4$— |
| R-10 | OMe | H | H | H | H | (3-Me-5-isoxazolyl)methyl | —$(CH_2)_4$— |
| R-11 | OEt | H | H | H | H | (3-Me-5-isoxazolyl)methyl | —$(CH_2)_4$— |
| R-12 | $OPr^i$ | H | H | H | H | (3-Me-5-isoxazolyl)methyl | —$(CH_2)_4$— |
| R-13 | OPr | H | H | H | H | (3-Me-5-isoxazolyl)methyl | —$(CH_2)_4$— |
| R-14 | $OCHF_2$ | H | H | H | H | (3-Me-5-isoxazolyl)methyl | —$(CH_2)_4$— |
| R-15 | $OCF_3$ | H | H | H | H | (3-Me-5-isoxazolyl)methyl | —$(CH_2)_4$— |
| R-16 | $CF_3$ | H | H | H | H | (3-Me-5-isoxazolyl)methyl | —$(CH_2)_4$— |
| R-17 | SMe | H | H | H | H | (3-Me-5-isoxazolyl)methyl | —$(CH_2)_4$— |
| R-18 | SEt | H | H | H | H | (3-Me-5-isoxazolyl)methyl | —$(CH_2)_4$— |
| R-19 | $SPr^i$ | H | H | H | H | (3-Me-5-isoxazolyl)methyl | —$(CH_2)_4$— |
| R-20 | $NMe_2$ | H | H | H | H | (3-Me-5-isoxazolyl)methyl | —$(CH_2)_4$— |

TABLE 73-continued

[Structure: phenyl ring with R¹–R⁵ substituents, connected via N=C to a thiazine ring bearing S, N-CSSR⁶, and R⁷, R⁸ substituents]

| | R¹ | R² | R³ | R⁴ | R⁵ | R⁶ | R⁷ | R⁸ |
|---|---|---|---|---|---|---|---|---|
| R-21 | NEt₂ | H | H | H | H | (3-Me-5-isoxazolyl)methyl | —(CH₂)₄— | |
| R-22 | H | Cl | H | H | H | (3-Me-5-isoxazolyl)methyl | —(CH₂)₄— | |
| R-23 | H | Br | H | H | H | (3-Me-5-isoxazolyl)methyl | —(CH₂)₄— | |
| R-24 | H | Me | H | H | H | (3-Me-5-isoxazolyl)methyl | —(CH₂)₄— | |
| R-25 | H | Et | H | H | H | (3-Me-5-isoxazolyl)methyl | —(CH₂)₄— | |

TABLE 74

[Structure: phenyl ring with R¹–R⁵ substituents, connected via N=C to a thiazine ring bearing S, N-CSSR⁶, and R⁷, R⁸ substituents]

| | R¹ | R² | R³ | R⁴ | R⁵ | R⁶ | R⁷ | R⁸ |
|---|---|---|---|---|---|---|---|---|
| R-26 | H | Pr | H | H | H | (3-Me-5-isoxazolyl)methyl | —(CH₂)₄— | |
| R-27 | H | Prⁱ | H | H | H | (3-Me-5-isoxazolyl)methyl | —(CH₂)₄— | |
| R-28 | H | Bu | H | H | H | (3-Me-5-isoxazolyl)methyl | —(CH₂)₄— | |
| R-29 | H | Buⁱ | H | H | H | (3-Me-5-isoxazolyl)methyl | —(CH₂)₄— | |
| R-30 | H | Buˢ | H | H | H | (3-Me-5-isoxazolyl)methyl | —(CH₂)₄— | |
| R-31 | H | Buᵗ | H | H | H | (3-Me-5-isoxazolyl)methyl | —(CH₂)₄— | |
| R-32 | H | OMe | H | H | H | (3-Me-5-isoxazolyl)methyl | —(CH₂)₄— | |
| R-33 | H | OEt | H | H | H | (3-Me-5-isoxazolyl)methyl | —(CH₂)₄— | |
| R-34 | H | OPr | H | H | H | (3-Me-5-isoxazolyl)methyl | —(CH₂)₄— | |
| R-35 | H | OPrⁱ | H | H | H | (3-Me-5-isoxazolyl)methyl | —(CH₂)₄— | |
| R-36 | H | OCHF₂ | H | H | H | (3-Me-5-isoxazolyl)methyl | —(CH₂)₄— | |
| R-37 | H | OCF₃ | H | H | H | (3-Me-5-isoxazolyl)methyl | —(CH₂)₄— | |
| R-38 | H | CF₃ | H | H | H | (3-Me-5-isoxazolyl)methyl | —(CH₂)₄— | |
| R-39 | H | SMe | H | H | H | (3-Me-5-isoxazolyl)methyl | —(CH₂)₄— | |
| R-40 | H | SEt | H | H | H | (3-Me-5-isoxazolyl)methyl | —(CH₂)₄— | |
| R-41 | H | SPrⁱ | H | H | H | (3-Me-5-isoxazolyl)methyl | —(CH₂)₄— | |
| R-42 | H | NMe₂ | H | H | H | (3-Me-5-isoxazolyl)methyl | —(CH₂)₄— | |
| R-43 | H | NEt₂ | H | H | H | (3-Me-5-isoxazolyl)methyl | —(CH₂)₄— | |
| R-44 | H | H | Cl | H | H | (3-Me-5-isoxazolyl)methyl | —(CH₂)₄— | |
| R-45 | H | H | Br | H | H | (3-Me-5-isoxazolyl)methyl | —(CH₂)₄— | |
| R-46 | H | H | Me | H | H | (3-Me-5-isoxazolyl)methyl | —(CH₂)₄— | |
| R-47 | H | H | Et | H | H | (3-Me-5-isoxazolyl)methyl | —(CH₂)₄— | |
| R-48 | H | H | Pr | H | H | (3-Me-5-isoxazolyl)methyl | —(CH₂)₄— | |
| R-49 | H | H | Prⁱ | H | H | (3-Me-5-isoxazolyl)methyl | —(CH₂)₄— | |
| R-50 | H | H | Bu | H | H | (3-Me-5-isoxazolyl)methyl | —(CH₂)₄— | |

TABLE 75

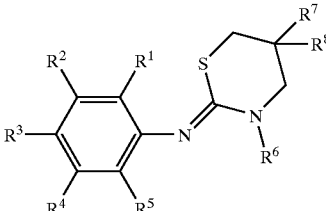

| | $R^1$ | $R^2$ | $R^3$ | $R^4$ | $R^5$ | $R^6$ | $R^7$ | $R^8$ |
|---|---|---|---|---|---|---|---|---|
| R-51 | H | H | $Bu^i$ | H | H | (3-Me-5-isoxazolyl)methyl | —$(CH_2)_4$— | |
| R-52 | H | H | $Bu^s$ | H | H | (3-Me-5-isoxazolyl)methyl | —$(CH_2)_4$— | |
| R-53 | H | H | $Bu^t$ | H | H | (3-Me-5-isoxazolyl)methyl | —$(CH_2)_4$— | |
| R-54 | H | H | OMe | H | H | (3-Me-5-isoxazolyl)methyl | —$(CH_2)_4$— | |
| R-55 | H | H | OEt | H | H | (3-Me-5-isoxazolyl)methyl | —$(CH_2)_4$— | |
| R-56 | H | H | OPr | H | H | (3-Me-5-isoxazolyl)methyl | —$(CH_2)_4$— | |
| R-57 | H | H | $OPr^i$ | H | H | (3-Me-5-isoxazolyl)methyl | —$(CH_2)_4$— | |
| R-58 | H | H | $OCHF_2$ | H | H | (3-Me-5-isoxazolyl)methyl | —$(CH_2)_4$— | |
| R-59 | H | H | $OCF_3$ | H | H | (3-Me-5-isoxazolyl)methyl | —$(CH_2)_4$— | |
| R-60 | H | H | $CF_3$ | H | H | (3-Me-5-isoxazolyl)methyl | —$(CH_2)_4$— | |
| R-61 | H | H | SMe | H | H | (3-Me-5-isoxazolyl)methyl | —$(CH_2)_4$— | |
| R-62 | H | H | SEt | H | H | (3-Me-5-isoxazolyl)methyl | —$(CH_2)_4$— | |
| R-63 | H | H | $SPr^i$ | H | H | (3-Me-5-isoxazolyl)methyl | —$(CH_2)_4$— | |
| R-64 | H | H | $NMe_2$ | H | H | (3-Me-5-isoxazolyl)methyl | —$(CH_2)_4$— | |
| R-65 | H | H | $NEt_2$ | H | H | (3-Me-5-isoxazolyl)methyl | —$(CH_2)_4$— | |
| R-66 | Me | $NMe_2$ | H | H | H | (3-Me-5-isoxazolyl)methyl | —$(CH_2)_4$— | |
| R-67 | $NMe_2$ | Cl | H | H | H | (3-Me-5-isoxazolyl)methyl | —$(CH_2)_4$— | |
| R-68 | Me | $NEt_2$ | H | H | H | (3-Me-5-isoxazolyl)methyl | —$(CH_2)_4$— | |
| R-69 | H | $NEt_2$ | Me | H | H | (3-Me-5-isoxazolyl)methyl | —$(CH_2)_4$— | |
| R-70 | $Bu^s$ | H | H | H | H | (3-Me-5-isoxazolyl)methyl | —$(CH_2)_4$— | |
| R-71 | OMe | H | Et | H | H | (3-Me-5-isoxazolyl)methyl | —$(CH_2)_4$— | |
| R-72 | H | OMe | OMe | H | H | (3-Me-5-isoxazolyl)methyl | —$(CH_2)_4$— | |
| R-73 | H | OMe | OEt | H | H | (3-Me-5-isoxazolyl)methyl | —$(CH_2)_4$— | |
| R-74 | H | OEt | OMe | H | H | (3-Me-5-isoxazolyl)methyl | —$(CH_2)_4$— | |
| R-75 | H | OEt | OEt | H | H | (3-Me-5-isoxazolyl)methyl | —$(CH_2)_4$— | |
| R-76 | —$(CH_2)_3$— | | H | H | H | (3-Me-5-isoxazolyl)methyl | —$(CH_2)_4$— | |
| R-77 | —$(CH_2)_4$— | | H | H | H | (3-Me-5-isoxazolyl)methyl | —$(CH_2)_4$— | |

TABLE 76

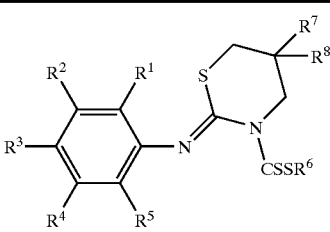

| | $R^1$ | $R^2$ | $R^3$ | $R^4$ | $R^5$ | $R^6$ | $R^7$ | $R^8$ |
|---|---|---|---|---|---|---|---|---|
| S-1 | H | H | H | H | H | (3-Me-5-isoxazolyl)methyl | —$(CH_2)_5$— | |
| S-2 | Cl | H | H | H | H | (3-Me-5-isoxazolyl)methyl | —$(CH_2)_5$— | |
| S-3 | Br | H | H | H | H | (3-Me-5-isoxazolyl)methyl | —$(CH_2)_5$— | |
| S-4 | Me | H | H | H | H | (3-Me-5-isoxazolyl)methyl | —$(CH_2)_5$— | |
| 5-5 | Et | H | H | H | H | (3-Me-5-isoxazolyl)methyl | —$(CH_2)_5$— | |
| S-6 | Pr | H | H | H | H | (3-Me-5-isoxazolyl)methyl | —$(CH_2)_5$— | |
| S-7 | Bu | H | H | H | H | (3-Me-5-isoxazolyl)methyl | —$(CH_2)_5$— | |
| S-8 | $Bu^i$ | H | H | H | H | (3-Me-5-isoxazolyl)methyl | —$(CH_2)_5$— | |
| S-9 | $Bu^t$ | H | H | H | H | (3-Me-5-isoxazolyl)methyl | —$(CH_2)_5$— | |
| S-10 | OMe | H | H | H | H | (3-Me-5-isoxazolyl)methyl | —$(CH_2)_5$— | |
| S-11 | OEt | H | H | H | H | (3-Me-5-isoxazolyl)methyl | —$(CH_2)_5$— | |
| S-12 | $OPr^i$ | H | H | H | H | (3-Me-5-isoxazolyl)methyl | —$(CH_2)_5$— | |
| S-13 | OPr | H | H | H | H | (3-Me-5-isoxazolyl)methyl | —$(CH_2)_5$— | |
| S-14 | $OCHF_2$ | H | H | H | H | (3-Me-5-isoxazolyl)methyl | —$(CH_2)_5$— | |
| S-15 | $OCF_3$ | H | H | H | H | (3-Me-5-isoxazolyl)methyl | —$(CH_2)_5$— | |
| S-16 | $CF_3$ | H | H | H | H | (3-Me-5-isoxazolyl)methyl | —$(CH_2)_5$— | |
| S-17 | SMe | H | H | H | H | (3-Me-5-isoxazolyl)methyl | —$(CH_2)_5$— | |
| S-18 | SEt | H | H | H | H | (3-Me-5-isoxazolyl)methyl | —$(CH_2)_5$— | |
| S-19 | $SPr^i$ | H | H | H | H | (3-Me-5-isoxazolyl)methyl | —$(CH_2)_5$— | |
| S-20 | $NMe_2$ | H | H | H | H | (3-Me-5-isoxazolyl)methyl | —$(CH_2)_5$— | |

TABLE 76-continued

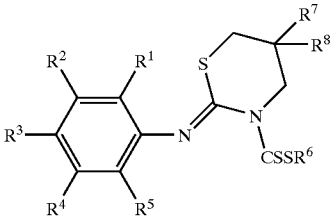

| | $R^1$ | $R^2$ | $R^3$ | $R^4$ | $R^5$ | $R^6$ | $R^7$ | $R^8$ |
|---|---|---|---|---|---|---|---|---|
| S-21 | NEt$_2$ | H | H | H | H | (3-Me-5-isoxazolyl)methyl | —(CH$_2$)$_5$— | |
| S-22 | H | Cl | H | H | H | (3-Me-5-isoxazolyl)methyl | —(CH$_2$)$_5$— | |
| S-23 | H | Br | H | H | H | (3-Me-5-isoxazolyl)methyl | —(CH$_2$)$_5$— | |
| S-24 | H | Me | H | H | H | (3-Me-5-isoxazolyl)methyl | —(CH$_2$)$_5$— | |
| S-25 | H | Et | H | H | H | (3-Me-5-isoxazolyl)methyl | —(CH$_2$)$_5$— | |

TABLE 77

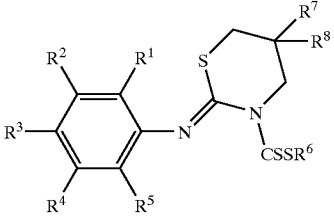

| | $R^1$ | $R^2$ | $R^3$ | $R^4$ | $R^5$ | $R^6$ | $R^7$ | $R^8$ |
|---|---|---|---|---|---|---|---|---|
| S-26 | H | Pr | H | H | H | (3-Me-5-isoxazolyl)methyl | —(CH$_2$)$_5$— | |
| S-27 | H | Pr$^i$ | H | H | H | (3-Me-5-isoxazolyl)methyl | —(CH$_2$)$_5$— | |
| S-28 | H | Bu | H | H | H | (3-Me-5-isoxazolyl)methyl | —(CH$_2$)$_5$— | |
| S-29 | H | Bu$^i$ | H | H | H | (3-Me-5-isoxazolyl)methyl | —(CH$_2$)$_5$— | |
| S-30 | H | Bu$^s$ | H | H | H | (3-Me-5-isoxazolyl)methyl | —(CH$_2$)$_5$— | |
| S-31 | H | Bu$^t$ | H | H | H | (3-Me-5-isoxazolyl)methyl | —(CH$_2$)$_5$— | |
| S-32 | H | OMe | H | H | H | (3-Me-5-isoxazolyl)methyl | —(CH$_2$)$_5$— | |
| S-33 | H | OEt | H | H | H | (3-Me-5-isoxazolyl)methyl | —(CH$_2$)$_5$— | |
| S-34 | H | OPr | H | H | H | (3-Me-5-isoxazolyl)methyl | —(CH$_2$)$_5$— | |
| S-35 | H | OPr$^i$ | H | H | H | (3-Me-5-isoxazolyl)methyl | —(CH$_2$)$_5$— | |
| S-36 | H | OCHF$_2$ | H | H | H | (3-Me-5-isoxazolyl)methyl | —(CH$_2$)$_5$— | |
| S-37 | H | OCF$_3$ | H | H | H | (3-Me-5-isoxazolyl)methyl | —(CH$_2$)$_5$— | |
| S-38 | H | CF$_3$ | H | H | H | (3-Me-5-isoxazolyl)methyl | —(CH$_2$)$_5$— | |
| S-39 | H | SMe | H | H | H | (3-Me-5-isoxazolyl)methyl | —(CH$_2$)$_5$— | |
| S-40 | H | SEt | H | H | H | (3-Me-5-isoxazolyl)methyl | —(CH$_2$)$_5$— | |
| S-41 | H | SPr$^i$ | H | H | H | (3-Me-5-isoxazolyl)methyl | —(CH$_2$)$_5$— | |
| S-42 | H | NMe$_2$ | H | H | H | (3-Me-5-isoxazolyl)methyl | —(CH$_2$)$_5$— | |
| S-43 | H | NEt$_2$ | H | H | H | (3-Me-5-isoxazolyl)methyl | —(CH$_2$)$_5$— | |
| S-44 | H | H | Cl | H | H | (3-Me-5-isoxazolyl)methyl | —(CH$_2$)$_5$— | |
| S-45 | H | H | Br | H | H | (3-Me-5-isoxazolyl)methyl | —(CH$_2$)$_5$— | |
| S-46 | H | H | Me | H | H | (3-Me-5-isoxazolyl)methyl | —(CH$_2$)$_5$— | |
| S-47 | H | H | Et | H | H | (3-Me-5-isoxazolyl)methyl | —(CH$_2$)$_5$— | |
| S-48 | H | H | Pr | H | H | (3-Me-5-isoxazolyl)methyl | —(CH$_2$)$_5$— | |
| S-49 | H | H | Pr$^i$ | H | H | (3-Me-5-isoxazolyl)methyl | —(CH$_2$)$_5$— | |
| S-50 | H | H | Bu | H | H | (3-Me-5-isoxazolyl)methyl | —(CH$_2$)$_5$— | |

TABLE 78

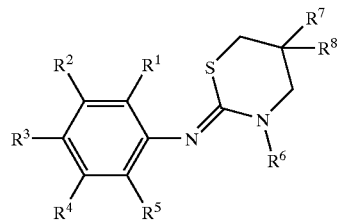

| | R¹ | R² | R³ | R⁴ | R⁵ | R⁶ | R⁷ R⁸ |
|---|---|---|---|---|---|---|---|
| S-51 | H | H | Bu$^i$ | H | H | (3-Me-5-isoxazolyl)methyl | —(CH$_2$)$_5$— |
| S-52 | H | H | Bu$^s$ | H | H | (3-Me-5-isoxazolyl)methyl | —(CH$_2$)$_5$— |
| S-53 | H | H | Bu$^t$ | H | H | (3-Me-5-isoxazolyl)methyl | —(CH$_2$)$_5$— |
| S-54 | H | H | OMe | H | H | (3-Me-5-isoxazolyl)methyl | —(CH$_2$)$_5$— |
| S-55 | H | H | OEt | H | H | (3-Me-5-isoxazolyl)methyl | —(CH$_2$)$_5$— |
| S-56 | H | H | OPr | H | H | (3-Me-5-isoxazolyl)methyl | —(CH$_2$)$_5$— |
| S-57 | H | H | OPr$^i$ | H | H | (3-Me-5-isoxazolyl)methyl | —(CH$_2$)$_5$— |
| S-58 | H | H | OCHF$_2$ | H | H | (3-Me-5-isoxazolyl)methyl | —(CH$_2$)$_5$— |
| S-59 | H | H | OCF$_3$ | H | H | (3-Me-5-isoxazolyl)methyl | —(CH$_2$)$_5$— |
| S-60 | H | H | CF$_3$ | H | H | (3-Me-5-isoxazolyl)methyl | —(CH$_2$)$_5$— |
| S-61 | H | H | SMe | H | H | (3-Me-5-isoxazolyl)methyl | —(CH$_2$)$_5$— |
| S-62 | H | H | SEt | H | H | (3-Me-5-isoxazolyl)methyl | —(CH$_2$)$_5$— |
| S-63 | H | H | SPr$^i$ | H | H | (3-Me-5-isoxazolyl)methyl | —(CH$_2$)$_5$— |
| S-64 | H | H | NMe$_2$ | H | H | (3-Me-5-isoxazolyl)methyl | —(CH$_2$)$_5$— |
| S-65 | H | H | NEt$_2$ | H | H | (3-Me-5-isoxazolyl)methyL | —(CH$_2$)$_5$— |
| S-66 | Me | NMe$_2$ | H | H | H | (3-Me-5-isoxazolyl)methyl | —(CH$_2$)$_5$— |
| S-67 | NMe$_2$ | Cl | H | H | H | (3-Me-5-isoxazolyl)methyl | —(CH$_2$)$_5$— |
| S-68 | Me | NEt$_2$ | H | H | H | (3-Me-5-isoxazolyl)methyl | —(CH$_2$)$_5$— |
| S-69 | H | NEt$_2$ | Me | H | H | (3-Me-5-isoxazolyl)methyl | —(CH$_2$)$_5$— |
| S-70 | Bu$^s$ | H | H | H | H | (3-Me-5-isoxazolyl)methyl | —(CH$_2$)$_5$— |
| S-71 | Pr$^i$ | H | H | H | H | (3-Me-5-isoxazolyl)methyl | —(CH$_2$)$_5$— |
| S-72 | H | OMe | OMe | H | H | (3-Me-5-isoxazolyl)methyl | —(CH$_2$)$_5$— |
| S-73 | H | OMe | OEt | H | H | (3-Me-5-isoxazolyl)methyl | —(CH$_2$)$_5$— |
| S-74 | H | OEt | OMe | H | H | (3-Me-5-isoxazolyl)methyl | —(CH$_2$)$_5$— |
| S-75 | H | OEt | OEt | H | H | (3-Me-5-isoxazolyl)methyl | —(CH$_2$)$_5$— |
| S-76 | —(CH$_2$)$_3$— | | H | H | H | (3-Me-5-isoxazolyl)methyl | —(CH$_2$)$_5$— |
| S-77 | —(CH$_2$)$_4$— | | H | H | H | (3-Me-5-isoxazolyl)methyl | —(CH$_2$)$_5$— |

TABLE 79

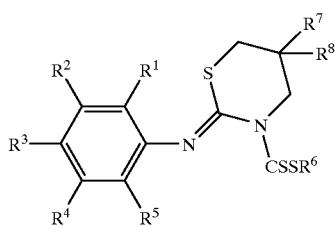

| | R¹ | R² | R³ | R⁴ | R⁵ | R⁶ | R⁷ R⁸ |
|---|---|---|---|---|---|---|---|
| T-1 | H | H | H | H | H | Me | —(CH$_2$)$_2$O(CH$_2$)$_2$— |
| T-2 | Cl | H | H | H | H | Me | —(CH$_2$)$_2$O(CH$_2$)$_2$— |
| T-3 | Br | H | H | H | H | Me | —(CH$_2$)$_2$O(CH$_2$)$_2$— |
| T-4 | Me | H | H | H | H | Me | —(CH$_2$)$_2$O(CH$_2$)$_2$— |
| T-5 | Et | H | H | H | H | Me | —(CH$_2$)$_2$O(CH$_2$)$_2$— |
| T-6 | Pr | H | H | H | H | Me | —(CH$_2$)$_2$O(CH$_2$)$_2$— |
| T-7 | Bu | H | H | H | H | Me | —(CH$_2$)$_2$O(CH$_2$)$_2$— |
| T-8 | Bu$^i$ | H | H | H | H | Me | —(CH$_2$)$_2$O(CH$_2$)$_2$— |
| T-9 | Bu$^t$ | H | H | H | H | Me | —(CH$_2$)$_2$O(CH$_2$)$_2$— |
| T-10 | OMe | H | H | H | H | Me | —(CH$_2$)$_2$O(CH$_2$)$_2$— |
| T-11 | OEt | H | H | H | H | Me | —(CH$_2$)$_2$O(CH$_2$)$_2$— |
| T-12 | OPr$^i$ | H | H | H | H | Me | —(CH$_2$)$_2$O(CH$_2$)$_2$— |
| T-13 | OPr | H | H | H | H | Me | —(CH$_2$)$_2$O(CH$_2$)$_2$— |
| T-14 | OCHF$_2$ | H | H | H | H | Me | —(CH$_2$)$_2$O(CH$_2$)$_2$— |
| T-15 | OCF$_3$ | H | H | H | H | Me | —(CH$_2$)$_2$O(CH$_2$)$_2$— |

TABLE 79-continued

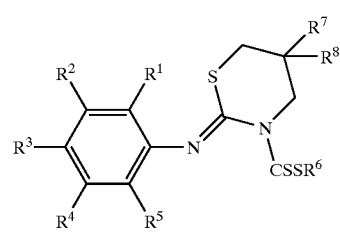

| | R¹ | R² | R³ | R⁴ | R⁵ | R⁶ | R⁷ R⁸ |
|---|---|---|---|---|---|---|---|
| T-16 | CF$_3$ | H | H | H | H | Me | —(CH$_2$)$_2$O(CH$_2$)$_2$— |
| T-17 | SMe | H | H | H | H | Me | —(CH$_2$)$_2$O(CH$_2$)$_2$— |
| T-18 | SEt | H | H | H | H | Me | —(CH$_2$)$_2$O(CH$_2$)$_2$— |
| T-19 | SPr$^i$ | H | H | H | H | Me | —(CH$_2$)$_2$O(CH$_2$)$_2$— |
| T-20 | NMe$_2$ | H | H | H | H | Me | —(CH$_2$)$_2$O(CH$_2$)$_2$— |
| T-21 | NEt$_2$ | H | H | H | H | Me | —(CH$_2$)$_2$O(CH$_2$)$_2$— |
| T-22 | H | Cl | H | H | H | Me | —(CH$_2$)$_2$O(CH$_2$)$_2$— |
| T-23 | H | Br | H | H | H | Me | —(CH$_2$)$_2$O(CH$_2$)$_2$— |
| T-24 | H | Me | H | H | H | Me | —(CH$_2$)$_2$O(CH$_2$)$_2$— |
| T-25 | H | Et | H | H | H | Me | —(CH$_2$)$_2$O(CH$_2$)$_2$— |

TABLE 80

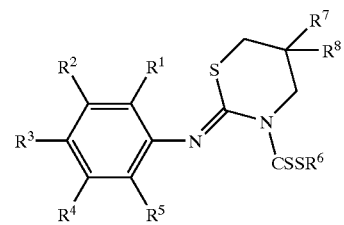

| | R¹ | R² | R³ | R⁴ | R⁵ | R⁶ | R⁷ R⁸ |
|---|---|---|---|---|---|---|---|
| T-26 | H | Pr | H | H | H | Me | —(CH₂)₂O(CH₂)₂— |
| T-27 | H | Prⁱ | H | H | H | Me | —(CH₂)₂O(CH₂)₂— |
| T-28 | H | Bu | H | H | H | Me | —(CH₂)₂O(CH₂)₂— |
| T-29 | H | Buⁱ | H | H | H | Me | —(CH₂)₂O(CH₂)₂— |
| T-30 | H | Buˢ | H | H | H | Me | —(CH₂)₂O(CH₂)₂— |
| T-31 | H | Buᵗ | H | H | H | Me | —(CH₂)₂O(CH₂)₂— |
| T-32 | H | OMe | H | H | H | Me | —(CH₂)₂O(CH₂)₂— |
| T-33 | H | OEt | H | H | H | Me | —(CH₂)₂O(CH₂)₂— |
| T-34 | H | OPr | H | H | H | Me | —(CH₂)₂O(CH₂)₂— |
| T-35 | H | OPrⁱ | H | H | H | Me | —(CH₂)₂O(CH₂)₂— |
| T-36 | H | OCHF₂ | H | H | H | Me | —(CH₂)₂O(CH₂)₂— |
| T-37 | H | OCF₃ | H | H | H | Me | —(CH₂)₂O(CH₂)₂— |
| T-38 | H | CF₃ | H | H | H | Me | —(CH₂)₂O(CH₂)₂— |
| T-39 | H | SMe | H | H | H | Me | —(CH₂)₂O(CH₂)₂— |
| T-40 | H | SEt | H | H | H | Me | —(CH₂)₂O(CH₂)₂— |
| T-41 | H | SPrⁱ | H | H | H | Me | —(CH₂)₂O(CH₂)₂— |
| T-42 | H | NMe₂ | H | H | H | Me | —(CH₂)₂O(CH₂)₂— |
| T-43 | H | NEt₂ | H | H | H | Me | —(CH₂)₂O(CH₂)₂— |
| T-44 | H | H | Cl | H | H | Me | —(CH₂)₂O(CH₂)₂— |
| T-45 | H | H | Br | H | H | Me | —(CH₂)₂O(CH₂)₂— |
| T-46 | H | H | Me | H | H | Me | —(CH₂)₂O(CH₂)₂— |
| T-47 | H | H | Et | H | H | Me | —(CH₂)₂O(CH₂)₂— |
| T-48 | H | H | Pr | H | H | Me | —(CH₂)₂O(CH₂)₂— |
| T-49 | H | H | Prⁱ | H | H | Me | —(CH₂)₂O(CH₂)₂— |
| T-50 | H | H | Bu | H | H | Me | —(CH₂)₂O(CH₂)₂— |

TABLE 81

| | R¹ | R² | R³ | R⁴ | R⁵ | R⁶ | R⁷ R⁸ |
|---|---|---|---|---|---|---|---|
| T-51 | H | H | Buⁱ | H | H | Me | —(CH₂)₂O(CH₂)₂— |
| T-52 | H | H | Buˢ | H | H | Me | —(CH₂)₂O(CH₂)₂— |
| T-53 | H | H | Buᵗ | H | H | Me | —(CH₂)₂O(CH₂)₂— |
| T-54 | H | H | OMe | H | H | Me | —(CH₂)₂O(CH₂)₂— |
| T-55 | H | H | OEt | H | H | Me | —(CH₂)₂O(CH₂)₂— |
| T-56 | H | H | OPr | H | H | Me | —(CH₂)₂O(CH₂)₂— |
| T-57 | H | H | OPrⁱ | H | H | Me | —(CH₂)₂O(CH₂)₂— |
| T-58 | H | H | OCHF₂ | H | H | Me | —(CH₂)₂O(CH₂)₂— |
| T-59 | H | H | OCF₃ | H | H | Me | —(CH₂)₂O(CH₂)₂— |
| T-60 | H | H | CF₃ | H | H | Me | —(CH₂)₂O(CH₂)₂— |
| T-61 | H | H | SMe | H | H | Me | —(CH₂)₂O(CH₂)₂— |
| T-62 | H | H | SEt | H | H | Me | —(CH₂)₂O(CH₂)₂— |
| T-63 | H | H | SPrⁱ | H | H | Me | —(CH₂)₂O(CH₂)₂— |
| T-64 | H | H | NMe₂ | H | H | Me | —(CH₂)₂O(CH₂)₂— |
| T-65 | H | H | NEt₂ | H | H | Me | —(CH₂)₂O(CH₂)₂— |
| T-66 | Me | NMe₂ | H | H | H | Me | —(CH₂)₂O(CH₂)₂— |
| T-67 | NMe₂ | Cl | H | H | H | Me | —(CH₂)₂O(CH₂)₂— |
| T-68 | Me | NEt₂ | H | H | H | Me | —(CH₂)₂O(CH₂)₂— |
| T-69 | H | NEt₂ | Me | H | H | Me | —(CH₂)₂O(CH₂)₂— |
| T-70 | Buˢ | H | H | H | H | Me | —(CH₂)₂O(CH₂)₂— |
| T-71 | OMe | H | OMe | H | H | Me | —(CH₂)₂O(CH₂)₂— |
| T-72 | H | OMe | OMe | H | H | Me | —(CH₂)₂O(CH₂)₂— |

TABLE 81-continued

| | R¹ | R² | R³ | R⁴ | R⁵ | R⁶ | R⁷ R⁸ |
|---|---|---|---|---|---|---|---|
| T-73 | H | OMe | OEt | H | H | Me | —(CH₂)₂O(CH₂)₂— |
| T-74 | H | OEt | OMe | H | H | Me | —(CH₂)₂O(CH₂)₂— |
| T-75 | H | OEt | OEt | H | H | Me | —(CH₂)₂O(CH₂)₂— |
| T-76 | —(CH₂)₃— | | H | H | H | Me | —(CH₂)₂O(CH₂)₂— |
| T-77 | —(CH₂)₄— | | H | H | H | Me | —(CH₂)₂O(CH₂)₂— |

TABLE 82

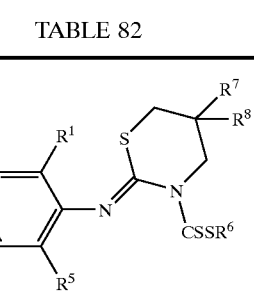

| | R¹ | R² | R³ | R⁴ | R⁵ | R⁶ | R⁷ R⁸ |
|---|---|---|---|---|---|---|---|
| U-1 | H | H | H | H | H | Et | —(CH₂)₂O(CH₂)₂— |
| U-2 | Cl | H | H | H | H | Et | —(CH₂)₂O(CH₂)₂— |
| U-3 | Br | H | H | H | H | Et | —(CH₂)₂O(CH₂)₂— |
| U-4 | Me | H | H | H | H | Et | —(CH₂)₂O(CH₂)₂— |
| U-5 | Et | H | H | H | H | Et | —(CH₂)₂O(CH₂)₂— |
| U-6 | Pr | H | H | H | H | Et | —(CH₂)₂O(CH₂)₂— |
| U-7 | Bu | H | H | H | H | Et | —(CH₂)₂O(CH₂)₂— |
| U-8 | Buⁱ | H | H | H | H | Et | —(CH₂)₂O(CH₂)₂— |
| U-9 | Buᵗ | H | H | H | H | Et | —(CH₂)₂O(CH₂)₂— |
| U-10 | OMe | H | H | H | H | Et | —(CH₂)₂O(CH₂)₂— |
| U-11 | OEt | H | H | H | H | Et | —(CH₂)₂O(CH₂)₂— |
| U-12 | OPrⁱ | H | H | H | H | Et | —(CH₂)₂O(CH₂)₂— |
| U-13 | OPr | H | H | H | H | Et | —(CH₂)₂O(CH₂)₂— |
| U-14 | OCHF₂ | H | H | H | H | Et | —(CH₂)₂O(CH₂)₂— |
| U-15 | OCF₃ | H | H | H | H | Et | —(CH₂)₂O(CH₂)₂— |
| U-16 | CF₃ | H | H | H | H | Et | —(CH₂)₂O(CH₂)₂— |
| U-17 | SMe | H | H | H | H | Et | —(CH₂)₂O(CH₂)₂— |
| U-18 | SEt | H | H | H | H | Et | —(CH₂)₂O(CH₂)₂— |
| U-19 | SPrⁱ | H | H | H | H | Et | —(CH₂)₂O(CH₂)₂— |
| U-20 | NMe₂ | H | H | H | H | Et | —(CH₂)₂O(CH₂)₂— |
| U-21 | NEt₂ | H | H | H | H | Et | —(CH₂)₂O(CH₂)₂— |
| U-22 | H | Cl | H | H | H | Et | —(CH₂)₂O(CH₂)₂— |
| U-23 | H | Br | H | H | H | Et | —(CH₂)₂O(CH₂)₂— |
| U-24 | H | Me | H | H | H | Et | —(CH₂)₂O(CH₂)₂— |
| U-25 | H | Et | H | H | H | Et | —(CH₂)₂O(CH₂)₂— |

TABLE 83

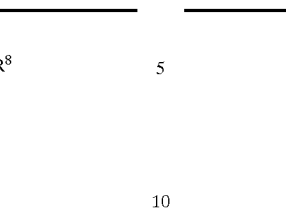

| | R¹ | R² | R³ | R⁴ | R⁵ | R⁶ | R⁷ | R⁸ |
|---|---|---|---|---|---|---|---|---|
| U-26 | H | Pr | H | H | H | Et | —(CH$_2$)$_2$O(CH$_2$)$_2$— | |
| U-27 | H | Pr$^i$ | H | H | H | Et | —(CH$_2$)$_2$O(CH$_2$)$_2$— | |
| U-28 | H | Bu | H | H | H | Et | —(CH$_2$)$_2$O(CH$_2$)$_2$— | |
| U-29 | H | Bu$^i$ | H | H | H | Et | —(CH$_2$)$_2$O(CH$_2$)$_2$— | |
| U-30 | H | Bu$^s$ | H | H | H | Et | —(CH$_2$)$_2$O(CH$_2$)$_2$— | |
| U-31 | H | Bu$^t$ | H | H | H | Et | —(CH$_2$)$_2$O(CH$_2$)$_2$— | |
| U-32 | H | OMe | H | H | H | Et | —(CH$_2$)$_2$O(CH$_2$)$_2$— | |
| U-33 | H | OEt | H | H | H | Et | —(CH$_2$)$_2$O(CH$_2$)$_2$— | |
| U-34 | H | OPr | H | H | H | Et | —(CH$_2$)$_2$O(CH$_2$)$_2$— | |
| U-35 | H | OPr$^i$ | H | H | H | Et | —(CH$_2$)$_2$O(CH$_2$)$_2$— | |
| U-36 | H | OCHF$_2$ | H | H | H | Et | —(CH$_2$)$_2$O(CH$_2$)$_2$— | |
| U-37 | H | OCF$_3$ | H | H | H | Et | —(CH$_2$)$_2$O(CH$_2$)$_2$— | |
| U-38 | H | CF$_3$ | H | H | H | Et | —(CH$_2$)$_2$O(CH$_2$)$_2$— | |
| U-39 | H | SMe | H | H | H | Et | —(CH$_2$)$_2$O(CH$_2$)$_2$— | |
| U-40 | H | SEt | H | H | H | Et | —(CH$_2$)$_2$O(CH$_2$)$_2$— | |
| U-41 | H | SPr$^i$ | H | H | H | Et | —(CH$_2$)$_2$O(CH$_2$)$_2$— | |
| U-42 | H | NMe$_2$ | H | H | H | Et | —(CH$_2$)$_2$O(CH$_2$)$_2$— | |
| U-43 | H | NEt$_2$ | H | H | H | Et | —(CH$_2$)$_2$O(CH$_2$)$_2$— | |
| U-44 | H | H | Cl | H | H | Et | —(CH$_2$)$_2$O(CH$_2$)$_2$— | |
| U-45 | H | H | Br | H | H | Et | —(CH$_2$)$_2$O(CH$_2$)$_2$— | |
| U-46 | H | H | Me | H | H | Et | —(CH$_2$)$_2$O(CH$_2$)$_2$— | |
| U-47 | H | H | Et | H | H | Et | —(CH$_2$)$_2$O(CH$_2$)$_2$— | |
| U-48 | H | H | Pr | H | H | Et | —(CH$_2$)$_2$O(CH$_2$)$_2$— | |
| U-49 | H | H | Pr$^i$ | H | H | Et | —(CH$_2$)$_2$O(CH$_2$)$_2$— | |
| U-50 | H | H | Bu | H | H | Et | —(CH$_2$)$_2$O(CH$_2$)$_2$— | |

TABLE 84

| | R¹ | R² | R³ | R⁴ | R⁵ | R⁶ | R⁷ | R⁸ |
|---|---|---|---|---|---|---|---|---|
| U-51 | H | H | Bu$^i$ | H | H | Et | —(CH$_2$)$_2$O(CH$_2$)$_2$— | |
| U-52 | H | H | Bu$^s$ | H | H | Et | —(CH$_2$)$_2$O(CH$_2$)$_2$— | |
| U-53 | H | H | Bu$^t$ | H | H | Et | —(CH$_2$)$_2$O(CH$_2$)$_2$— | |
| U-54 | H | H | OMe | H | H | Et | —(CH$_2$)$_2$O(CH$_2$)$_2$— | |
| U-55 | H | H | OEt | H | H | Et | —(CH$_2$)$_2$O(CH$_2$)$_2$— | |
| U-56 | H | H | OPr | H | H | Et | —(CH$_2$)$_2$O(CH$_2$)$_2$— | |
| U-57 | H | H | OPr$^i$ | H | H | Et | —(CH$_2$)$_2$O(CH$_2$)$_2$— | |
| U-58 | H | H | OCHF$_2$ | H | H | Et | —(CH$_2$)$_2$O(CH$_2$)$_2$— | |
| U-59 | H | H | OCF$_3$ | H | H | Et | —(CH$_2$)$_2$O(CH$_2$)$_2$— | |
| U-60 | H | H | CF$_3$ | H | H | Et | —(CH$_2$)$_2$O(CH$_2$)$_2$— | |
| U-61 | H | H | SMe | H | H | Et | —(CH$_2$)$_2$O(CH$_2$)$_2$— | |
| U-62 | H | H | SEt | H | H | Et | —(CH$_2$)$_2$O(CH$_2$)$_2$— | |
| U-63 | H | H | SPr$^i$ | H | H | Et | —(CH$_2$)$_2$O(CH$_2$)$_2$— | |
| U-64 | H | H | NMe$_2$ | H | H | Et | —(CH$_2$)$_2$O(CH$_2$)$_2$— | |
| U-65 | H | H | NEt$_2$ | H | H | Et | —(CH$_2$)$_2$O(CH$_2$)$_2$— | |
| U-66 | Me | NMe$_2$ | H | H | H | Et | —(CH$_2$)$_2$O(CH$_2$)$_2$— | |
| U-67 | NMe$_2$ | Cl | H | H | H | Et | —(CH$_2$)$_2$O(CH$_2$)$_2$— | |
| U-68 | Me | NEt$_2$ | H | H | H | Et | —(CH$_2$)$_2$O(CH$_2$)$_2$— | |
| U-69 | H | NEt$_2$ | Me | H | H | Et | —(CH$_2$)$_2$O(CH$_2$)$_2$— | |
| U-70 | Bu$^s$ | H | H | H | H | Et | —(CH$_2$)$_2$O(CH$_2$)$_2$— | |
| U-71 | OMe | H | OMe | H | H | Et | —(CH$_2$)$_2$O(CH$_2$)$_2$— | |
| U-72 | H | OMe | OMe | H | H | Et | —(CH$_2$)$_2$O(CH$_2$)$_2$— | |

TABLE 84-continued

| | R¹ | R² | R³ | R⁴ | R⁵ | R⁶ | R⁷ | R⁸ |
|---|---|---|---|---|---|---|---|---|
| U-73 | H | OMe | OEt | H | H | Et | —(CH$_2$)$_2$O(CH$_2$)$_2$— | |
| U-74 | H | OEt | OMe | H | H | Et | —(CH$_2$)$_2$O(CH$_2$)$_2$— | |
| U-75 | H | OEt | OEt | H | H | Et | —(CH$_2$)$_2$O(CH$_2$)$_2$— | |
| U-76 | —(CH$_2$)$_3$— | | H | H | H | Et | —(CH$_2$)$_2$O(CH$_2$)$_2$— | |
| U-77 | —(CH$_2$)$_4$— | | H | H | H | Et | —(CH$_2$)$_2$O(CH$_2$)$_2$— | |

The above compounds of the present invention were examined as shown below.

Test Example 1

Experiments for Human CB2 Receptor (CB2R) Binding Inhibition

The coding region of human CB2R cDNA (Munro etc, Nature, 1993, 365, 61–65) was inserted into the mammalian expression vector, pSVL SV40 Late Promoter Expression Vector (Amersham Pharmacia Biotech Inc.). The prepared vector was transfected into Chinese Hamster Ovary (CHO) cells with LipofectAMINE reagent (Gibco BRL) according to the manufacture's protocol, and the stable CB2R-expressing clones were selected.

The crude membrane fractions were prepared from the CB2R-expressing CHO cells. Receptor binding assay was performed by incubating the membranes with each test compound and [$^3$H]CP55940 (at a final concentration of 0.5 nM: NEN Life Science Products) in the assay buffer (50 mM Tris-HCl, 1 mM EDTA, 3 mM MgCl$_2$, pH 7.4) containing 0.5% bovine serum albumin (BSA) for 2 h at 25° C. The incubation mixture was filtered through 1% polyethylenimine-treated GF/C glass filter and washed with 50 mM Tris-HCl (pH 7.4) containing 0.1% BSA. The radioactivity was then counted with a liquid scintillation counter. Non-specific binding was determined in the presence of 10 μM WIN55212-2 (a cannabinoid receptor agonist described in the U.S. Pat. No. 508,122, Research Biochemicals International), and the specific binding was calculated by subtracting the non-specific binding from the total binding. The IC$_{50}$ value for each test compound was determined as the concentration at which 50% of the specific binding was inhibited.

For the receptor binding assay of human CB1 receptor (CB1R), the stable CB1R-expressing CHO cells were prepared as described above, and the binding assay was performed using their membrane fractions. As a consequence of these studies, the Ki values of each test compound for both cannabinoid receptors were determined, which were presented in Table. As shown in this table, a series of compounds described in the present invention were found to selectively block the binding of CP55940 (a cannabinoid receptor agonist described in the U.S. Pat. No. 4,371,720) to CB2R.

TABLE 85

| Compound | Ki (nM) | |
| --- | --- | --- |
| | CB1 receptor | CB2 receptor |
| I-13 | n.t. | 6 |
| I-14 | >5000 | 2 |
| I-17 | n.t. | 8 |
| I-39 | 906 | 2 |
| I-40 | n.t. | 0.5 |
| I-41 | n.t. | 1 |
| I-42 | >5000 | 0.3 |
| I-44 | 321 | 1.1 |
| I-45 | 386 | 1.2 |
| I-46 | 3226 | 2 |
| I-49 | 1116 | 2.9 |
| I-74 | 704 | 1.2 |
| I-78 | 1015 | 8 |
| I-80 | >5000 | 2.2 |
| I-88 | n.t. | 8 |
| I-89 | n.t. | 8 |
| I-92 | 1312 | 6 |
| I-93 | 1537 | 3 | n.t.: not tested

Example 2

Inhibition Experiments for CB2R-mediated Suppression of cAMP Synthesis

The CHO cells expressing human CB2R were incubated with test compounds for 15 min. After the incubation, forskolin (final concentration of 4 $\mu$M, Sigma) was added and the cells were incubated for 20 min at 37° C. The reaction was stopped by the addition of 1N HCl and the amount of cAMP in the cell supernatant was measured using an EIA kit (Amersham Pharmacia Biotech) according to the manufacture's protocol. The cAMP amount increased by forskolin compared to that in the absence of forskolin was defined as 100%, and the $IC_{50}$ value of each test compound was determined as the concentration at which 50% of the forskolin-stimulated cAMP synthesis was inhibited. As a consequence of these studies, the $IC_{50}$ value of each test compound was presented in Table. As shown in Table. the compounds described in the present invention were found to possess agonistic activity for CB2R.

The antagonistic activity of each compound was also evaluated in this assay.

TABLE 86

| Compound | $IC_{50}$ (nM) |
| --- | --- |
| I-46 | 5.4 |
| I-39 | 13.7 |
| I-49 | 2.2 |
| I-74 | 1.6 |
| I-92 | <0.2 |
| I-93 | 0.6 |

The compound of the present invention except compounds described above exhibited a binding activity to the cannabinoid type 2 receptor and an agonistic activity to the cannabinoid type 2 receptor as the same as or more than described above.

On the other hand, the compound of the present invention can be evaluated for its anti-inflammatory efficacy by the following in vivo studies.

Example 3

Experiments for Sheep Red Blood Cell (SRBC)-induced Delayed Type Hypersensitive (DTH) Reaction Female ddY mice (7 weeks old) were used for the sheep red blood cell (SRBC)-induced delayed type hypersensitive (DTH) reaction.

Cannabinoid receptor agonist, I-6, I-60, I-77 and I-118 were suspended in 0.6% arabic gum solution. Mice were sensitized by the intradermal injection of $10^7$ cells of SRBC (40 $\mu$l/foot) into the left hind foot pad. After 5 days, DTH reaction was induced by the intradermal injection of $10^8$ cells of SRBC in the right hind foot pad. Test compounds were administerd p.o. (10 ml/kg) 1 h before and 5 h after the induction of DTH reaction. After 24 h of the injection of SRBC, the left and right foot pad volumes were measured by the water displacement method. The foot pad swelling was calculated as the differences in the volumes between the right and left hind foot pad, and used as an index of the DTH reaction.

Data are expressed as the inhibition percentage of each compound. Statistical analysis was performed with Welch's t-test. in which the value of $P<0.05$ is considered as a significant difference.

Furthermore, the compound of the present invention is high stable to metabolism and an excellent pharmaceutical composition.

Formulation Example

It is to be noted that the following Formulation Examples 1 to 9 are mere illustration, but not intended to limit the scope of the invention. The term "active ingredient" means the compounds represented by the formula (I), a tautomer, a prodrug, a pharmaceutically acceptable salt or a solvate thereof.

Formulation Example 1

| Hard gelatin capsules are prepared using of the following ingredients: | |
| --- | --- |
| | Dose (mg/capsule) |
| Active ingredient | 250 |
| Starch, dried | 200 |
| Magnesium stearate | 10 |
| Total | 460 mg |

Formulation Example 2

| A tablet is prepared using of the following ingredients: | |
| --- | --- |
| | Dose (mg/tablet) |
| Active ingredient | 250 |
| Cellulose, microcrystals | 400 |

-continued

| A tablet is prepared using of the following ingredients: | |
|---|---|
| | Dose (mg/tablet) |
| Silicon dioxide, fumed | 10 |
| Stearic acid | 5 |
| Total | 665 mg |

The components are blended and compressed to form tablets each weighing 665 mg.

Formulation Example 3

| An aerosol solution is prepared containing the following components: | |
|---|---|
| | Weight |
| Active ingredient | 0.25 |
| Ethanol | 25.75 |
| Propellant 22 (chlorodifluoromethane) | 74.00 |
| Total | 100.00 |

The active compound is mixed with ethanol and the admixture added to a portion of the propellant 22, cooled to −30° C. and transferred to filling device. The required amount is then fed to stainless steel container and diluted with the reminder of the propellant. The valve units are then fitted to the container.

Formulation Example 4

| Tablets, each containing 60 mg of active ingredient, are made as follows. | |
|---|---|
| Active ingredient | 60 mg |
| Starch | 45 mg |
| Microcrystals cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve, and the mixed thoroughly. The aqueous solution containing polyvinylpyrrolidone is mixed with the resultant powder, and the admixture then is passed through a No. 14 mesh U.S. sieve. The granules so produced are dried at 50° C. and passed through a No. 18 mesh U.S. sieve. The sodium carboxymethyl starch, magnesium stearate, and talc, previously passed through No. 60 mesh U.S. sieve, are then added to the granules which, after mixing, are compressed on a tablet machine to yield tablets each weighing 150 mg.

Formulation Example 5

| Capsules, each containing 80 mg of active ingredient, are made as follows: | |
|---|---|
| Active ingredient | 80 mg |
| Starch | 59 mg |
| Microcrystals cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation Example 6

| Suppository, each containing 225 mg of active ingredient, are made as follows: | |
|---|---|
| Active ingredient | 225 mg |
| Saturated fatty acid glycerides | 2000 mg |
| Total | 2225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation Example 7

| Suspensions, each containing 50 mg of active ingredient per 5 ml dose, are made as follows: | |
|---|---|
| Active ingredient | 50 mg |
| Sodium carboxymethyl cellulose | 50 mg |
| Syrup | 1.25 mL |
| Benzoic acid solution | 0.10 mL |
| Flavor | q.v. |
| Color | q.v. |
| Purified water to total | 5 mL |

The active ingredient is passed through a No. 45 U.S. sieve, and mixed with the sodium carboxymethyl cellulose and syrup to form a smooth paste. The benzoic acid solution, flavor and color are diluted with a portion of the water and added, with stirring. Sufficient water is then added to produce the required volume.

Formulation Example 8

| An intravenous formulation may be prepared as follows: | |
|---|---|
| Active ingredient | 100 mg |
| Isotonic saline | 1000 mL |

The solution of the above ingredients generally is administered intravenously to a subject at a rate of 1 mL per minute.

Industrial Applicability

The compound of the present invention represented by the formula (I) binds to the cannabinoid type 2 receptor (CB2R), and exhibits an antagonistic activity or agonistic activity to CB2R. Therefore, the compound of the present invention can be used for treating or preventing diseases associated with the cannabinoid type 2 receptor (CB2R).

What is claimed is:

1. A compound of the formula (I):

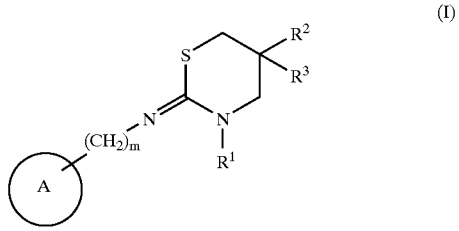

(I)

wherein $R^1$ is optionally substituted heterocyclic group or a group represented by the formula: $-C(=Z)W-R^4$ wherein Z is oxygen atom or sulfur atom; W is oxygen atom or sulfur atom; $R^4$ is optionally substituted alkyl, optionally substituted alkenyl or optionally substituted alkynyl;

$R^2$ and $R^3$ each is independently hydrogen, optionally substituted alkyl, optionally substituted alkoxyalkyl, optionally substituted aminoalkyl, or optionally substituted cycloalkyl; or $R^2$ and $R^3$ taken together form optionally substituted $C_2$–$C_{10}$ straight or branched alkylene which may contain one or three heteroatom(s);

m is an integer of 0 to 2;

A is optionally substituted aromatic carbocyclic group or optionally substituted aromatic heterocyclic group;

provided that when $R^1$ is a group represented by the formula: $-C(=Z)W-R^4$ wherein Z is oxygen atom or sulfur atom; W is oxygen atom or sulfur atom; and $R^4$ is unsubstituted alkyl, $R^2$ and $R^3$ taken together form optionally substituted $C_2$–$C_{10}$ straight or branched alkylene which contains one to three heteroatom(s);

a prodrug, a pharmaceutically acceptable salt or a solvate thereof.

2. The compound according to claim 1 wherein the following formula

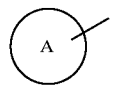

is the formula represented below:

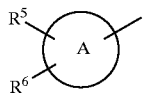

wherein $R^5$ and $R^6$ each is independently hydrogen, alkyl, alkoxy, alkylthio, optionally substituted amino, optionally substituted aryl, optionally substituted aryloxy, cycloalkyl, halogen, hydroxy, nitro, haloalkyl, haloalkoxy, optionally substituted carbamoyl, carboxy, alkoxycarbonyl, alkylsulfinyl, alkylsulfonyl, alkoxyalkyl, alkylthioalkyl, optionally substituted aminoalkyl, alkoxyalkoxy, alkylthioalkoxy, optionally substituted heteroaryl, optionally substituted non-aromatic heterocyclic group, alkoxyiminoalkyl, or a group of the formula: $-C(=O)-R^H$ wherein $R^H$ is hydrogen, alkyl, optionally substituted aryl or optionally substituted non-aromatic heterocyclic group; or $R^5$ and $R^6$ taken together form alkylenedioxy; A is aromatic carbocyclic group or aromatic heterocyclic group;

a prodrug, a pharmaceutically acceptable salt or a solvate thereof.

3. The compound according to claim 2 wherein $R^5$ is hydrogen, methyl, ethyl, n-propyl, isopropyl, n-butyl, isobutyl, sec-butyl, t-butyl, methoxy, ethoxy, n-propoxy, isopropoxy, n-butoxy, methylthio, ethylthio, n-propylthio, isopropylthio, dimethylamino, acetylamino, N-acetylmethylamino, diethylamino, ethylmethylamino, propylmethylamino, phenyl, phenoxy, fluoro, chloro, bromo, nitro, trifluoromethyl, difluoromethoxy, trifluoromethoxy, N-methylcarbamoyl, methoxycarbonyl, methanesulfinyl, ethanesulfinyl, methanesulfonyl, ethanesulfonyl, acetyl, methoxymethyl, 1-methoxyethyl, 3-pyridyl, morpholino, pyrrolidino, piperidino, 2-oxopyrrolidino, 1-methoxyiminoethyl or morpholinocarbonyl;

$R^6$ is hydrogen, methyl, ethyl, fluoro, chloro, nitro, methoxy or ethoxy; or $R^5$ and $R^6$ taken together form $-O-CH_2-O-$;

A is phenyl, naphthyl, pyridyl or quinolyl;

a prodrug, a pharmaceutically acceptable salt or a solvate thereof.

4. The compound according to claim 2 wherein $R^5$ and $R^6$ each is independently hydrogen, alkyl, alkoxy, or alkylthio; A is aromatic carbocyclic group;

a prodrug, a pharmaceutically acceptable salt or a solvate thereof.

5. The compound according to any one of claims 1 to 4 wherein m is 0;

a prodrug, a pharmaceutically acceptable salt or a solvate thereof.

6. The compound according to claim 5 wherein $R^1$ is optionally substituted heterocyclic group;

a prodrug, a pharmaceutically acceptable salt or a solvate thereof.

7. The compound according to claim 6 wherein $R^1$ is optionally substituted pyridyl, optionally substituted benzothiazolyl, optionally substituted benzoxazolyl or optionally substituted thiadiazolyl;

a prodrug, a pharmaceutically acceptable salt or a solvate thereof.

8. The compound according to claim 5 wherein a group represented by the formula: $-C(=Z)W-R^4$ wherein Z is oxygen atom or sulfur atom; W is oxygen atom or sulfur atom; $R^4$ is optionally substituted alkyl, optionally substituted alkenyl or optionally substituted alkynyl;

a prodrug, a pharmaceutically acceptable salt or a solvate thereof.

9. The compound according to claim 8 wherein Z and W are sulfur atom;

a prodrug, a pharmaceutically acceptable salt or a solvate thereof.

10. The compound according to claim 1 wherein $R^2$ and $R^3$ each is independently methyl, ethyl, propyl or methoxymethyl; or $R^2$ and $R^3$ taken together form ethylene, trimethylene, tetramethylene, pentamethylene or ethyleneoxyethylene;

a prodrug, a pharmaceutically acceptable salt or a solvate thereof.

11. The compound according to claim 1 represented by the formula:

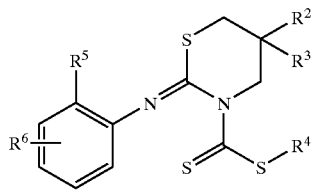

wherein $R^2$ and $R^3$ each is independently optionally substituted alkyl; or $R^2$ and $R^3$ taken together form optionally substituted $C_2$–$C_{10}$ straight or branched alkylene which may contain one or three heteroatom(s);
  $R^4$ is optionally substituted alkyl, optionally substituted alkenyl or optionally substituted alkynyl;
  $R^5$ is alkyl, alkoxy, or optionally substituted amino:
  $R^6$ is hydrogen, alkyl, alkoxy, optionally substituted amino or haloalkoxy;
a prodrug, a pharmaceutically acceptable salt or a solvate thereof.

12. The compound according to claim 11 wherein $R^4$ is optionally substituted alkyl (substituent is cyano, alkoxy, alkylcarbonyl, carboxy, alkoxycarbonyl, alkenyloxycarbonyl, alkoxyalkoxycarbonyl, optionally substituted carbamoyl (substituent is alkyl or alkoxy), halogen, alkylcarbonyloxy, aryloxy, optionally substituted non-aromatic heterocyclic group (substituent is alkyl), optionally substituted aromatic heterocyclic group (substituent is alkyl or aryl), or a group represented by the formula: —O—$R^I$ (wherein $R^I$ is non-aromatic heterocyclic group), alkenyl or alkynyl;
a prodrug of itself, a pharmaceutically acceptable salt thereof or a solvate thereof.

13. The compound according to claim 1 wherein A is optionally substituted phenyl, optionally substituted naphthyl, or optionally substituted quinolyl;
a prodrug, a pharmaceutically acceptable salt or a solvate thereof.

14. A pharmaceutical composition which comprises the compound according to claim 1, a prodrug, a pharmaceutically acceptable salt or a solvate thereof.

15. The pharmaceutical composition according to claim 14 which has an agonistic activity to the cannabinoid type 2 receptor.

* * * * *